US012790390B2

(12) United States Patent
Tsukerman et al.

(10) Patent No.: US 12,790,390 B2
(45) Date of Patent: Nov. 10, 2026

(54) ANTIBODIES AGAINST CD112R AND USES THEREOF

(71) Applicants: NECTIN THERAPEUTICS LTD., Jerusalem (IL); UNIVERSITY OF RIJEKA FACULTY OF MEDICINE, Rijeka (HR); YISSUM RESEARCH DEVELOPMENT COMPANY OF THE HEBREW UNIVERSITY OF JERUSALEM LTD., Jerusalem (IL)

(72) Inventors: Pinchas Tsukerman, Jerusalem (IL); Anas Atieh, Jerusalem (IL); Akram Obiedat, Jerusalem (IL); Guy Cinamon, Tel Aviv (IL); Stipan Jonjić, Rijeka (HR); Tihana Lenac Roviš, Kastav (HR); Paola Kučan Brlić, Rijeka (HR); Ofer Mandelboim, Shoham (IL)

(73) Assignees: NECTIN THERAPEUTICS LTD., Jerusalem (IL); UNIVERSITY OF RIJEKA FACULTY OF MEDICINE, Rijeka (HR); YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 599 days.

(21) Appl. No.: 18/264,279

(22) PCT Filed: Feb. 9, 2022

(86) PCT No.: PCT/IL2022/050162
§ 371 (c)(1),
(2) Date: Aug. 4, 2023

(87) PCT Pub. No.: WO2022/172267
PCT Pub. Date: Aug. 18, 2022

(65) Prior Publication Data
US 2024/0270840 A1 Aug. 15, 2024

Related U.S. Application Data

(60) Provisional application No. 63/148,149, filed on Feb. 11, 2021.

(51) Int. Cl.
*C07K 16/28* (2006.01)
*A61K 39/00* (2006.01)
*A61P 35/00* (2006.01)

(52) U.S. Cl.
CPC .............. *C07K 16/28* (2013.01); *A61P 35/00* (2018.01); *C07K 16/2803* (2013.01); *C07K 16/2818* (2013.01); *C07K 16/2896* (2013.01); *A61K 2039/505* (2013.01); *C07K 2317/24* (2013.01); *C07K 2317/622* (2013.01)

(58) Field of Classification Search
None
See application file for complete search history.

(56) References Cited

U.S. PATENT DOCUMENTS

| | | | | |
|---|---|---|---|---|
| 4,816,567 | A | 3/1989 | Cabilly | |
| 4,946,778 | A | 8/1990 | Ladner | |
| 5,225,539 | A | 7/1993 | Winter | |
| 5,530,101 | A | 6/1996 | Queen | |
| 5,585,089 | A | 12/1996 | Queen | |
| 5,641,870 | A | 6/1997 | Rinderknecht | |
| 5,693,761 | A | 12/1997 | Queen | |
| 5,693,762 | A | 12/1997 | Queen | |
| 9,714,289 | B2 | 7/2017 | White | |
| 10,227,408 | B2 | 3/2019 | White | |
| 10,351,625 | B2 | 7/2019 | White | |
| 11,220,542 | B2 | 1/2022 | White | |
| 11,623,955 | B2 | 4/2023 | White | |
| 2018/0169238 | A1 | 6/2018 | White | |
| 2020/0040092 | A1 * | 2/2020 | Mandelboim | C07K 16/2896 |
| 2021/0188974 | A1 | 6/2021 | White | |

FOREIGN PATENT DOCUMENTS

| | | | |
|---|---|---|---|
| EP | 0404097 | A2 | 12/1990 |
| EP | 3258951 | B1 | 1/2020 |
| IL | 254039 | B1 | 8/2023 |
| WO | 8601533 | A1 | 3/1986 |
| WO | 9007861 | A1 | 7/1990 |
| WO | 9222653 | A1 | 12/1992 |
| WO | 9311161 | A1 | 6/1993 |
| WO | 9315210 | A1 | 8/1993 |
| WO | 9613583 | A2 | 5/1996 |

(Continued)

OTHER PUBLICATIONS

Al-Lazikani et al., (1997) Standard conformations for the canonical structures of immunoglobulins. J Mol Biol 273(4):927-948.
Bird et al., (1988) Single-chain antigen-binding proteins. Science 242(4877): 423-426.
Brennan et al., (1985) Preparation of bispecific antibodies by chemical recombination of monoclonal immunoglobulin G1 fragments. Science 229(4708): 81-83.
Carter et al., (1992) High level *Escherichia coli* expression and production of a bivalent humanized antibody fragment. Biotechnology (N Y) 10(2): 163-167.
Chothia et al., (1989) Conformations of immunoglobulin hypervariable regions. Nature 342(6252): 877-883.

(Continued)

*Primary Examiner* — Juliet C Switzer
*Assistant Examiner* — Katherine Ann Holtzman
(74) *Attorney, Agent, or Firm* — Rothwell, Figg, Ernst & Manbeck, P.C.

(57) ABSTRACT

The present invention provides monoclonal antibodies that recognize human CD112R with high affinity and specificity and inhibit its binding to Nectin-2. The present invention further provides pharmaceutical compositions comprising the antibodies and methods for their use in cancer immunotherapy and in diagnosis.

22 Claims, 13 Drawing Sheets

Specification includes a Sequence Listing.

(56) References Cited

FOREIGN PATENT DOCUMENTS

| | | | | | |
|---|---|---|---|---|---|
| WO | 9637621 | A2 | | 11/1996 | |
| WO | WO-03046204 | A2 | * | 6/2003 | ................ A61P 9/00 |
| WO | 2016134333 | A1 | | 8/2016 | |
| WO | 2017037707 | A1 | | 3/2017 | |
| WO | 2018017864 | A2 | | 1/2018 | |
| WO | 2019232484 | A1 | | 12/2019 | |
| WO | 2020018879 | A1 | | 1/2020 | |
| WO | 2022015853 | A2 | | 1/2022 | |

OTHER PUBLICATIONS

Chowdhury (2003) Engineering hot spots for affinity enhancement of antibodies. Methods Mol Biol 207: 179-196.

Clackson et al., (1991) Making antibody fragments using phage display libraries. Nature 352(6336): 624-628.

Cunningham and Wells (1989) High-resolution epitope mapping of hGH-receptor interactions by alanine-scanning mutagenesis. Science 244(4908): 1081-1085.

Dumbrava et al., (2019) Phase 1 study of COM701 monotherapy and in combination with nivolumab in patients with advanced solid tumors. Journal for ImmunoTherapy of Cancer 7(Suppl 1): 231. Abstract P422.

Holliger et al., (1993) "Diabodies": small bivalent and bispecific antibody fragments. Proc Natl Acad Sci U S A 90(14): 6444-6448.

Honegger and Plückthun (2001) Yet another numbering scheme for immunoglobulin variable domains: an automatic modeling and analysis tool. J Mol Biol 309(3): 657-670.

Huston et al., (1988) Protein engineering of antibody binding sites: recovery of specific activity in an anti-digoxin single-chain Fv analogue produced in *Escherichia coli*. Proc Natl Acad Sci U S A 85(16): 5879-5883.

Köhler and Milstein (1975) Continuous cultures of fused cells secreting antibody of predefined specificity. Nature 256 (5517): 495-497.

Lefranc et al., (2003) IMGT unique numbering for immunoglobulin and T cell receptor variable domains and Ig superfamily V-like domains. Dev Comp Immunol 27(1): 55-77.

MacCallum et al., (1996) Antibody-antigen interactions: contact analysis and binding site topography. J Mol Biol 262(5): 732-745.

Marks et al., (1991) By-passing immunization. Human antibodies from V-gene libraries displayed on phage. J Mol Biol 222(3): 581-597.

Morimoto and Inouye (1992) Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24(1-2): 107-117.

Morrison et al., (1984) Chimeric human antibody molecules: mouse antigen-binding domains with human constant region domains. Proc Natl Acad Sci U S A 81(21): 6851-6855.

Panduro et al., (2020) Abstract 4548: SRF813, a fully human monoclonal antibody targeting the inhibitory receptor CD112R, enhances immune cell activation and demonstrates preclinical in vivo anti-tumor activity. Cancer Res 80 (16_Supplement): 4548. Abstract.

Scarano et al., (2010) Surface plasmon resonance imaging for affinity-based biosensors. Biosens Bioelectron 25(5): 957-966.

Ward et al., (1989) Binding activities of a repertoire of single immunoglobulin variable domains secreted from *Escherichia coli*. Nature 341(6242): 544-546.

Whelan et al., (2019) PVRIG and PVRL2 are Induced in Cancer and Inhibit CD8+ T-cell Function. Cancer Immunol Res 7(2): 257-268.

Whitelegg and Rees (2000) WAM: an improved algorithm for modelling antibodies on the WEB. Protein Eng 13(12): 819-824.

Wu and Kabat (1970) An analysis of the sequences of the variable regions of Bence Jones proteins and myeloma light chains and their implications for antibody complementarity. J Exp Med 132(2): 211-250.

Zapata et al., (1995) Engineering linear F(ab')2 fragments for efficient production in *Escherichia coli* and enhanced antiproliferative activity. Protein Eng 8(10): 1057-1062.

Altshuler et al., (2010) Generation of recombinant antibodies and means for increasing their affinity. Advances in Biological Chemistry 50: 203-258. Machine translation of p. 207, (3 page).

Altshuler et al., (2010) Generation of recombinant antibodies and means for increasing their affinity. Biochemistry (Mosc) 75(13): 1584-1605.

Brown et al., (1996) Tolerance to single, but not multiple, amino acid replacement in antibody Vh CDR2. The Journal of Immunology 156: 3285-3291.

Chen et al., (1995) Enhancement and destruction of antibody function by somatic mutation: unequal occurrence is controlled by V gene combinatorial associations. EMBO J 14(12): 2784-2794.

Coico (2008) Immunology: a textbook. Moscow: publishing center "Academy". pp. 61-62. Machine translation of pp. 61-62, (5 pages).

Colman (1994) Effects of amino acid sequence changes on antibody-antigen interactions. Res Immunol 145(1): 33-36.

Rudikoff (1982) Giusti AM, Cook WD, Scharff MD. Single amino acid substitution altering antigen-binding specificity Proc Natl Acad Sci U S A 79(6): 1979-1983.

* cited by examiner

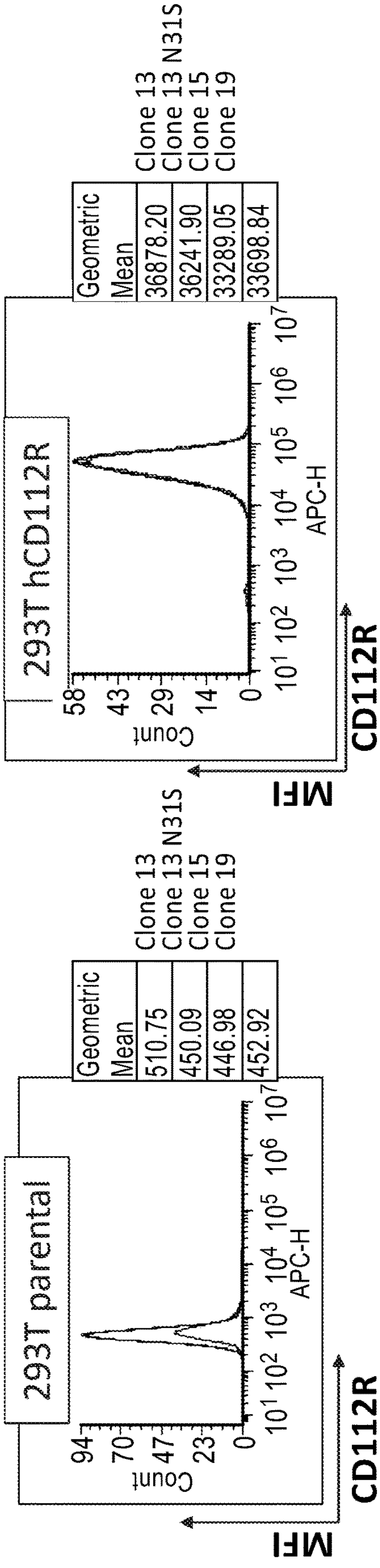
Figure 3A
| | Clone 13 | Clone 13 N31S | Clone 15 |
|---|---|---|---|
| EC50 (nM) | 1.24 | 0.7 | 1.29 |
Figure 3B
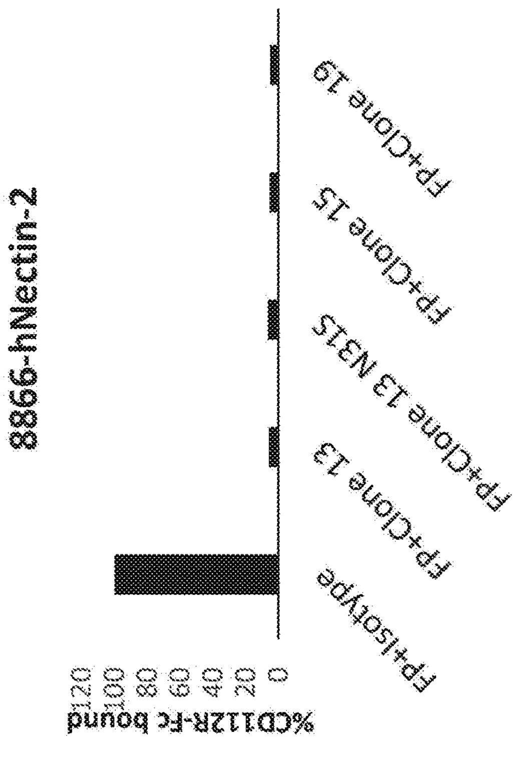
Figure 3C

ANTIBODIES AGAINST CD112R AND USES THEREOF

CROSS REFERENCE TO RELATED APPLICATION(S)

This application is a 35 U.S.C. 371 National Phase Entry Application from PCT/IL2022/050162, filed on Feb. 9, 2022, which claims the benefit of U.S. Provisional Application No. 63/148,149, filed on Feb. 11, 2021, the disclosures of which are incorporated therein in their entirety by reference.

The instant application contains a Sequence Listing which has been submitted via EFS-Web and is hereby incorporated by reference in its entirety. Said Sequence Listing, created on Dec. 26, 2023, is named NECTIN-002 PCT Amended sequence listing 261223_ST25.txt and is 80,950 bytes in size.

FIELD OF THE INVENTION

The present invention is in the field of immunotherapy and relates to antibodies and fragments thereof which bind to the human protein CD112R (PVRIG), to polynucleotide sequences encoding these antibodies and to cells producing them. Pharmaceutical compositions comprising these antibodies and their uses are also included.

BACKGROUND OF THE INVENTION

Cancer immunotherapy is utilized for generating and augmenting anti-tumor immune responses, e.g., by treatment with antibodies specific to antigens on tumor cells, by chimeric antigen receptors T cells (CAR-T), or by specific activation of anti-tumor cells. The ability of recruiting immune cells (e.g., T cells or NK cells) against tumor cells in a patient provides a therapeutic modality of fighting tumors and their metastasis that otherwise were considered incurable.

T cell mediated immune responses include multiple sequential steps regulated by co-stimulatory and co-inhibitory signals leading to a net effect that controls the magnitude of the immune response and its outcome. The inhibitory signals, referred to as immune checkpoints, are crucial for the maintenance of self-tolerance and for the limitation of immune-mediated collateral tissue damage.

The expression of immune checkpoint proteins is altered by tumors. For example, upregulation of programmed death-ligand 1 (PD-L1) on the surface of cancer cells allows them to bind to the checkpoint molecule PD-1, expressed on T cells. This leads to inhibition of T cells, which might otherwise attack the tumor cells, and thus allows the cancer cells to evade the host immune system. Hence, immune checkpoints represent significant barriers for the activation of functional cellular immunity against cancer. Accordingly, antagonistic antibodies specific for inhibitory ligands on T cells (e.g., PD-1) are examples of targeted agents against immune checkpoint inhibitors (ICIs) that are being used in cancer therapy (e.g., Nivolumab, Pembrolizumab). Another example for an immune checkpoint molecule is T cell immunoreceptor with Ig and ITIM domains (TIGIT). TIGIT is a co-inhibitory molecule expressed on various immune cells, including T cells and natural killer cells (NK cells). TIGIT binds with high affinity to polio virus receptor (PVR, CD155) and with low affinity to Nectin-2 (CD112), both expressed by various cancer cells.

CD112R, also called PVRIG, binds with high affinity to Nectin-2. Upon interaction with CD112R, and/or TIGIT, Nectin-2 inhibits T-cell proliferation. Importantly, Nectin-2 can also serve as a costimulator of T-cell functions, upon binding to CD226 (DNAM-1). This interaction stimulates T-cell proliferation and cytokine production, such as IL-2, and IFNγ. These contradictory interactions are competitive, and their net effect impacts the resulting anti-cancer immune response.

WO2019232484 discloses anti-PVRIG, anti-TIGIT, and anti-PVRIG/anti-TIGIT bispecific antibodies, as well as compositions, and methods of using the antibodies for the treatment of cancer.

WO2018017864 discloses agents and bi-specific agents, including antibodies that specifically bind PVRIG. WO2018017864 also discloses methods of using the agents for enhancing the immune response and/or treatment of diseases such as cancer.

WO2016134333 discloses anti-PVRIG antibodies and methods of using same.

There is an unmet need for additional and more effective, specific, safe, and stable agents that alone, or in combination with other agents, may potentiate cells of the immune system to attack tumors or virus infected cells. Monoclonal antibodies (mAbs) inhibiting CD112R binding to Nectin-2, may be such agents.

SUMMARY OF THE INVENTION

The present invention provides antibodies and fragments thereof that recognize CD112R (PVRIG), bind it, prevent its binding to Nectin-2 (CD112) and inhibit the resulting suppressive activity on lymphocytes such as natural killer (NK) cells and T-cells. These antibodies and fragment thereof are characterized by having unique sets of CDR sequences, high affinity, and high specificity to human CD112R, and are useful in cancer immunotherapy for combating tumor immune evasion, as either a stand-alone therapy or in combination with other anti-cancer agents. The antibodies disclosed herein are also useful in treating viral infections and may be used for detection assays and cancer diagnosis.

It is now disclosed that the high affinity anti-CD112R monoclonal antibodies (mAbs) described herein block CD112R-Nectin-2 interactions and subsequently restore T and NK cell activities. These properties make the mAbs of the present invention valuable candidates for use in anti-cancer immune-therapy, enabling administration of lower doses with fewer side effects.

The anti-CD112R mAbs described herein were found to induce T cell activation similarly to that induced by anti-PD-1, anti-TIGIT, and anti-PVR mAbs. Moreover, the combination of some of the anti-CD112R mAbs, described herein, with other immuno-modulating agents, including anti-PD-1, anti-TIGIT or anti-PVR mAbs resulted in a significant increase of anti-cancer activity that exceeded the activity level induced by each of the individual mAbs. CD112R mAbs disclosed herein were able to induce NK cell activation in the presence of target cancer cells and to synergize with anti-TIGIT and anti-PVR mAbs for the activation of NK cells. It is further disclosed that the antibodies described herein were found to be highly specific to human and cynomolgus CD112R, but not to rodent CD112R. It is further disclosed, according to some embodiments, that the anti-CD112R mAbs block CD112R interactions with its ligand Nectin-2 and increase activation of immune cells.

Unexpectedly, the humanized forms of the anti-CD112R mAbs of the present invention were found to possess improved binding and productivity properties in comparison to the parental murine mAbs. Furthermore, the humanized mAb variants have a cross-reactivity with cynomolgus CD112R, which enables further studies in monkeys. The antibodies described herein possess unique properties and improved potency over known anti-CD112R antibodies.

Surprisingly and advantageously, specific mutations in the complementarity determining region 1 (CDR1) of the light chain and in CDR1 of the heavy chain, introduced to remove deamidation and N-glycosylation motifs, respectively, preserved the affinity to human CD112R.

According to one aspect, the present invention provides an antibody, or an antibody fragment thereof comprising at least the antigen binding portion, which specifically binds to human CD112R, said antibody or fragment thereof have an affinity to human CD112R of at least $0.5\times10^{-9}$M.

According to some embodiments, the antibody specifically binds to human CD112R and inhibits its binding to its ligand, human Nectin-2 (CD112).

According to some embodiments, the antibody or antibody fragment comprises a set of six CDR sequences selected from the group consisting of:

i. three CDRs of a heavy-chain (HC) variable region comprising SEQ ID NO: 17 and three CDRs of a light-chain (LC) variable comprising SEQ ID NO: 19, or an analog or derivative thereof having at least 90% sequence identity with said antibody or fragment sequence; and
ii. three CDRs of a heavy-chain variable region comprising SEQ ID NO: 21 and three CDRs of a light-chain variable region comprising SEQ ID NO: 23, or an analog or derivative thereof having at least 90% sequence identity with said antibody or fragment sequence.

There are several methods known in the art for determining the CDR sequences of a given antibody molecule, but there is no standard unequivocal method. Determination of CDR sequences from antibody heavy and light chain variable regions can be made according to any method known in the art, including, but not limited to, the methods known as KABAT, Chothia, and IMGT. A selected set of CDRs may include sequences identified by more than one method, namely, some CDR sequences may be determined using KABAT and some using IMGT, for example. According to some embodiments, the CDR sequences of the mAb variable regions are determined using the KABAT and/or Chothia methods.

According to some embodiments, the antibody or its fragment comprises the CDR sequences of a monoclonal antibody denoted clone 13, namely, the three CDR sequences contained in heavy chain variable region set forth in SEQ ID NO: 17 and the three CDR sequences contained in light chain variable region set forth in SEQ ID NO: 19, or the CDR sequences of a monoclonal antibody denoted clone 15, namely, the three CDR sequences contained in heavy chain variable region set forth in SEQ ID NO: 21 and the three CDR sequences contained in light chain variable region set forth in SEQ ID NO: 23.

The present invention comprises variants and analogs of the antibody denoted clone 13. According to some embodiments, the antibody or antibody fragment comprises a set of three CDR sequences of a heavy-chain variable region comprising SEQ ID NO: 28 and three CDRs of a light-chain variable comprising SEQ ID NO: 26, or an analog or derivative thereof having at least 90% sequence identity with said antibody or fragment sequence.

According to some embodiments, the antibody or the antibody fragment comprises heavy-chain CDR1 comprising the sequence $GYX_1FX_2SY$ (SEQ ID NO: 1), wherein $X_1$ denotes N, D, A, Q, S, or T; and $X_2$ denotes T or A, or the sequence SYWIN (SEQ ID NO: 7). According to some embodiments, the antibody or the antibody fragment comprises heavy-chain CDR2 comprising the sequence YPGSYIP (SEQ ID NO: 2). According to some embodiments, the antibody or the antibody fragment comprises heavy-chain CDR3 comprising the sequence GYFDV (SEQ ID NO: 3).

According to certain embodiments, the antibody or the antibody fragment comprises: (i) heavy-chain CDR1 comprising the sequence $GYX_1FX_2SY$ (SEQ ID NO: 1) wherein $X_1$ denotes N, D, A, Q, S, or T; and $X_2$ denotes T or A, or the sequence SYWIN (SEQ ID NO: 7); (ii) heavy-chain CDR2 comprising the sequence YPGSYIP (SEQ ID NO: 2); and (iii) heavy-chain CDR3 comprising the sequence GYFDV (SEQ ID NO: 3).

According to some embodiments, the antibody or the antibody fragment comprises light-chain CDR1 comprising the sequence KSSQSLLXSGNQKNYLA (SEQ ID NO: 4), wherein X denotes N or S. According to some embodiments, the antibody or the antibody fragment comprises light-chain CDR2 comprising the sequence GASTRES (SEQ ID NO: 5). According to some embodiments, the antibody or the antibody fragment comprises light-chain CDR3 comprising the sequence QNDHSYPYT (SEQ ID NO: 6).

According to certain embodiments, the antibody or the antibody fragment comprises: (i) light-chain CDR1 comprising the sequence KSSQSLLXSGNQKNYLA (SEQ ID NO: 4) wherein X denotes N or S; (ii) light-chain CDR2 comprising the sequence GASTRES (SEQ ID NO: 5); and (iii) heavy-chain CDR3 comprising the sequence QNDHSYPYT (SEQ ID NO: 6).

According to some specific embodiments the antibody or fragment comprises heavy chain CDR1 sequence comprising the sequence $GYX_1FX_2SY$ (SEQ ID NO: 1), wherein $X_1$ denotes N, D, A, Q, S, or T; and $X_2$ denotes T or A or the sequence SYWIN (SEQ ID NO: 7), heavy chain CDR2 comprising the sequence YPGSYIP (SEQ ID NO: 2), heavy chain CDR3 comprising the sequence GYFDV (SEQ ID NO: 3), light chain CDR1 comprising the sequence KSSQSLLXSGNQKNYLA (SEQ ID NO: 4) wherein X denotes N or S, light chain CDR2 comprising the sequence GASTRES (SEQ ID NO: 5), and light chain CDR3 comprising the sequence QNDHSYPYT (SEQ ID NO: 6), or analogs thereof comprising no more than 5% amino acid substitution, deletion and/or insertion in the hypervariable region (HVR) sequence that comprises the six CDRs.

According to some specific embodiments the antibody or fragment comprises a set of six CDR sequences consisting of:

i. heavy chain CDR1 having a sequence set forth in SEQ ID NO: 1 or 7;
ii. heavy chain CDR2 having a sequence set forth in SEQ ID NO: 2;
iii. heavy chain CDR3 having a sequence set forth in SEQ ID NO: 3;
iv. light chain CDR1 having a sequence set forth in SEQ ID NO: 4;
v. light chain CDR2 having a sequence set forth in SEQ ID NO: 5; and
vi. light chain CDR3 having a sequence set forth in SEQ ID NO: 6.

According to some embodiments, the heavy chain CDR1 sequence comprises the sequence $GYX_1FX_2SY$ (SEQ ID NO: 1), wherein $X_1$ denotes N, D, A, Q, S, or T; and $X_2$ is T or A. According to some embodiments, the heavy chain CDR1 sequence comprising the sequence $GYX_1FX_2SY$ (SEQ ID NO: 1), wherein $X_1$ denotes N, D, A, Q, S, or T and $X_2$ is T. According to some embodiments, the heavy chain CDR1 sequence comprising the sequence GYTFTSY (SEQ ID NO: 13). According to additional embodiments, the heavy chain CDR1 sequence comprising the sequence GYNFASY (SEQ ID NO: 14). According to additional embodiments, the heavy chain CDR1 sequence comprising the sequence SYWIN (SEQ ID NO: 7).

According to some embodiments, the heavy chain CDR2 sequence comprising the sequence YPGSYIP (SEQ ID NO: 2) or DIYPGSYIPNYNEKFKN (SEQ ID NO: 8). According to certain embodiments, the heavy chain CDR2 sequence comprising the sequence DIYPGSYIPNYNEKFKN (SEQ ID NO: 8).

According to some embodiments, the light chain CDR1 sequence comprising the sequence KSSQSLLXSGNQKNYLA (SEQ ID NO: 4), wherein X is N. According to specific embodiments, the light chain CDR1 sequence comprising the sequence KSSQSLLSSGNQKNYLA (SEQ ID NO: 15).

According to some embodiments, the antibody or fragment thereof comprises heavy chain variable region set forth in SEQ ID NO: 28, or an analog or derivative thereof having at least 90% sequence identity with the heavy chain variable region sequence.

According to some embodiments, the antibody or fragment thereof comprises light chain variable region set forth in SEQ ID NO: 26, or an analog thereof having at least 90% sequence identity with the light chain variable region sequence.

According to a specific embodiment, the antibody or fragment thereof comprises a heavy chain variable region having a sequence set forth in SEQ ID NO: 28, and a light chain variable region having a sequence set forth in SEQ ID NO: 26, or an analog thereof having at least 90% sequence identity with the light and/or heavy chain sequence.

According to a specific embodiment, the antibody or fragment thereof comprises a heavy chain variable region having a sequence set forth in SEQ ID NO: 17, and a light chain variable region having a sequence set forth in SEQ ID NO: 19, or an analog thereof having at least 90% sequence identity with the light and/or heavy chain sequence.

According to some embodiments, the antibody or fragment comprises the CDR sequences of a monoclonal antibody denoted clone 13, namely, the three CDR sequences contained in heavy chain variable region set forth in SEQ ID NO: 17 and the three CDR sequences contained in light chain variable region set forth in SEQ ID NO: 19.

According to additional embodiments, the antibody or the antibody fragment comprises heavy-chain CDR1 comprising the sequence GYNFTSY (SEQ ID NO: 9) or SYWIN (SEQ ID NO: 7). According to some embodiments, the antibody or the antibody fragment comprises heavy-chain CDR2 comprising the sequence FPGSYS (SEQ ID NO: 10). According to some embodiments, the antibody or the antibody fragment comprises heavy-chain CDR3 comprising the sequence GYFDV (SEQ ID NO: 3).

According to certain embodiments, the antibody or the antibody fragment comprises: (i) heavy-chain CDR1 comprising the sequence GYNFTSY (SEQ ID NO: 9) or SYWIN (SEQ ID NO: 7); (ii) heavy-chain CDR2 comprising the sequence FPGSYS (SEQ ID NO: 10); and (iii) heavy-chain CDR3 comprising the sequence GYFDV (SEQ ID NO: 3).

According to some embodiments, the antibody or the antibody fragment comprises light-chain CDR1 comprising the sequence KSSQSLLNSGSQKNYLA (SEQ ID NO: 11). According to some embodiments, the antibody or the antibody fragment comprises light-chain CDR2 comprising the sequence GASTRES (SEQ ID NO: 5). According to some embodiments, the antibody or the antibody fragment comprises light-chain CDR3 comprising the sequence QNDHSYPYT (SEQ ID NO: 6).

According to certain embodiments, the antibody or the antibody fragment comprises: (i) light-chain CDR1 comprising the sequence KSSQSLLNSGSQKNYLA (SEQ ID NO: 11); (ii) light-chain CDR2 comprising the sequence GASTRES (SEQ ID NO: 5); and (iii) heavy-chain CDR3 comprising the sequence QNDHSYPYT (SEQ ID NO: 6).

According to some specific embodiments, the antibody or fragment comprises heavy chain CDR1 sequence comprising the sequence GYNFTSY (SEQ ID NO: 9) or SYWIN (SEQ ID NO: 7), heavy chain CDR2 comprising the sequence FPGSYS (SEQ ID NO: 10), heavy chain CDR3 comprising the sequence GYFDV (SEQ ID NO: 3), light chain CDR1 comprising the sequence KSSQSLLNSGSQKNYLA (SEQ ID NO: 11), light chain CDR2 comprising the sequence GASTRES (SEQ ID NO: 5), and light chain CDR3 comprising the sequence QNDHSYPYT (SEQ ID NO: 6), or analogs thereof comprising no more than 5% amino acid substitution, deletion and/or insertion in the hypervariable region (HVR) sequence.

According to some specific embodiments the antibody or fragment comprises a set of six CDR sequences consisting of:

i. heavy chain CDR1 having a sequence set forth in SEQ ID NO: 9 or 7;
ii. heavy chain CDR2 having a sequence set forth in SEQ ID NO: 10;
iii. heavy chain CDR3 having a sequence set forth in SEQ ID NO: 3;
iv. light chain CDR1 having a sequence set forth in SEQ ID NO: 11;
v. light chain CDR2 having a sequence set forth in SEQ ID NO: 5; and
vi. light chain CDR3 having a sequence set forth in SEQ ID NO: 6.

According to some embodiments, the light chain CDR1 sequence comprising the sequence GYNFTSY (SEQ ID NO: 9). According to other embodiments, the light chain CDR1 sequence comprising the sequence SYWIN (SEQ ID NO: 7).

According to some embodiments, the heavy chain CDR2 sequence comprising the sequence DIFPGSYSPNYNKKFKR (SEQ ID NO: 12).

According to some embodiments, the CDRs are determined by KABAT and set forth in SEQ ID NOs: 7, 8, 3, 4, 5, and 6. According to some embodiments, the CDRs are determined by KABAT and set forth in SEQ ID NOs: 7, 12, 3, 11, 5, and 6.

According to some embodiments, the CDRs are determined by Chothia and set forth in SEQ ID NOs: 1, 2, 3, 4, 5, and 6. According to some embodiments, the CDRs are determined by Chothia and set forth in SEQ ID NOs: 9, 10, 3, 11, 5, and 6.

According to some embodiments, the antibody or fragment thereof comprises heavy chain variable region set forth in SEQ ID NO: 21, or an analog or derivative thereof having at least 90% sequence identity with the heavy chain variable region sequence.

According to some embodiments, the antibody or fragment thereof comprises light chain variable region set forth in SEQ ID NO: 23, or an analog thereof having at least 90% sequence identity with the light chain variable region sequence.

According to a specific embodiment, the antibody or fragment thereof comprises a heavy chain variable region having a sequence set forth in SEQ ID NO: 21, and a light chain variable region having a sequence set forth in SEQ ID NO: 23, or an analog thereof having at least 90% sequence identity with the light and/or heavy chain sequence.

According to a specific embodiment, the antibody or fragment thereof comprises a heavy chain variable region having a sequence set forth in SEQ ID NO: 21, and a light chain variable region having a sequence set forth in SEQ ID NO: 23.

According to some embodiments, the antibody or fragment thereof recognizes human CD112R with affinity of at least $10^{-10}$M. According to other embodiments, the antibody or antibody fragment binds with affinity of $5\times10^{-11}$M, or even higher, to human CD112R. According to some embodiments, the antibody or antibody fragment binds to human CD112R with affinity at the range of $0.5\times10^{-9}$M to $10^{-11}$M. According to some embodiments, the antibody or antibody fragment binds to human CD112R with affinity at the range of $10^{-10}$M to $10^{-11}$M. Each possibility represents a separate embodiment of the invention.

Analogs and derivatives of the antibody and the fragments described above, are also within the scope of the invention.

According to some embodiments, the antibody or antibody fragment analog have at least 95% sequence identity with the hypervariable region of the reference antibody sequence.

According to certain embodiments, the analog or derivative of the isolated antibody or fragment thereof has at least 91, 92, 93, 94, 95, 96, 97, 98 or 99% sequence identity with a variable region of the reference antibody sequence. Each possibility represents a separate embodiment of the invention.

According to some embodiments, the antibody or antibody fragment according to the invention comprises a heavy chain variable region set forth in SEQ ID NO: 28 or SEQ ID NO: 21, or an analog having at least 95% sequence similarity with said sequence.

According to some embodiments, the antibody or antibody fragment comprises a light chain variable region set forth in SEQ ID NO: 26 or SEQ ID NO: 23, or an analog having at least 95% sequence similarity with said sequence.

According to some embodiments, the antibody or antibody fragment comprises a heavy chain and a light chain, wherein: (i) the heavy chain comprises SEQ ID NO: 28 and the light chain comprises SEQ ID NO: 26; or (ii) the heavy chain comprises SEQ ID NO: 21 and the light chain comprises SEQ ID NO: 23. Analogs of the antibodies or fragments, having at least 95% sequence similarity with said heavy or light chains are also included.

According to some embodiments, the analog has at least 96, 97, 98 or 99% sequence similarity or identity with an antibody light or heavy chain variable regions described above. According to some embodiments, the analog comprises no more than one amino acid substitution, deletion or addition to one or more CDR sequences of the hypervariable region, namely, any one of the CDR sequences set forth in SEQ ID NOs: 1, 2, 3, 4, 5, 6, 7, 8, 9, 10, 11, 12, 13, 14 and 15. Each possibility represents a separate embodiment of the present invention. According to some embodiments, the amino acid substitution is a conservative substitution.

According to some embodiments, the antibody or antibody fragment comprises a hypervariable region (HVR) having light and heavy chain regions defined above, in which 1, 2, 3, 4, or 5 amino acids were substituted, deleted and/or added. Each possibility represents a separate embodiment of the invention.

According to some embodiments, the antibody or antibody fragment comprises a HVR having light and heavy chain regions defined above, in which one amino acid was substituted. According to specific embodiments, the antibody or antibody fragment comprises a CDR as defined above, in which one amino acid was substituted.

According to some embodiments, the antibody or the antibody fragment comprises a CDR set selected from the group consisting of:

i. a set of six CDRs wherein: heavy-chain CDR1 is GY$X_1$F$X_2$SY (SEQ ID NO: 1) wherein $X_1$ denotes N, D, A, Q, S, or T; and $X_2$ denotes T or A; heavy-chain CDR2 is YPGSYIP (SEQ ID NO: 2); heavy-chain CDR3 is GYFDV (SEQ ID NO: 3); light-chain CDR1 is KSSQSLLXSGNQKNYLA (SEQ ID NO: 4) wherein X denotes N or S; light-chain CDR2 is GASTRES (SEQ ID NO: 5); and light-chain CDR3 is QNDHSYPYT (SEQ ID NO: 6);

ii. a set of six CDRs wherein: heavy-chain CDR1 is SYWIN (SEQ ID NO: 7); heavy-chain CDR2 is YPGSYIP (SEQ ID NO: 2); heavy-chain CDR3 is GYFDV (SEQ ID NO: 3); light-chain CDR1 is KSSQSLLXSGNQKNYLA (SEQ ID NO: 4) wherein X denotes N or S; light-chain CDR2 is GASTRES (SEQ ID NO: 5); and light-chain CDR3 is QNDHSYPYT (SEQ ID NO: 6); and iii. a set of six CDRs wherein: heavy-chain CDR1 sequence is GYNFTSY (SEQ ID NO: 9) or SYWIN (SEQ ID NO: 7); heavy-chain CDR2 is FPGSYS (SEQ ID NO: 10); heavy-chain CDR3 is GYFDV (SEQ ID NO: 3); light-chain CDR1 is KSSQSLLNSGSQKNYLA (SEQ ID NO: 11); light-chain CDR2 is GASTRES (SEQ ID NO: 5); and light-chain CDR3 is QNDHSYPYT (SEQ ID NO: 6).

The present invention also provides antibodies and binding fragments thereof, comprising a heavy chain and a light chain, wherein said chains comprise a set of heavy chain variable region sequence and light chain variable region sequence, said set is selected from the group consisting of:

i. SEQ ID NOs: 17 and 19; and ii. SEQ ID NOs: 21 and 23.

The present invention also provides antibodies and binding fragments thereof, comprising a heavy chain and a light chain, wherein said chains comprises a set of heavy chain variable region sequence set forth in SEQ ID NO: 28 and light chain variable region sequence set forth in SEQ ID NO: 26.

According to some embodiments, the antibody is an isolated monoclonal antibody.

According to specific embodiments, the mAb is a chimeric mAb.

According to some embodiments, the mAb or the chimeric mAb comprises a constant region selected from the group consisting of: mouse IgG1, mouse IgG2a, mouse IgG2b, mouse IgG3, human IgG1, human IgG2, human IgG3 and human IgG4. Each possibility represents a separate embodiment of the present invention.

According to yet other embodiments, the chimeric mAb comprised of human-derived constant region.

According to some embodiments the human constant regions of the chimeric mAb are selected from the group consisting of: human IgG1, human IgG2, human IgG3, and human IgG4.

According to some embodiments the human constant region of the chimeric mAb is human IgG1.

According to specific embodiments, the antibody is an antibody fragment. According to a specific embodiment, the antibody fragment is selected from the group consisting of: Fab, Fab', $F(ab')_2$, Fd, Fd', Fv, dAb, isolated CDR region, single chain variable fragment (scFv), single chain antibody (scab), "diabodies", and "linear antibodies". Each possibility represents a separate embodiment of the present invention.

The present invention also provides humanized antibodies comprising a set of six CDRs of any of the mAbs described herein.

According to some embodiments, the humanized antibody or the antibody fragment comprises a set of six CDRs wherein: heavy-chain CDR1 is $GYX_1FX_2SY$ (SEQ ID NO: 1), wherein $X_1$ denotes N, D, A, Q, S, or T; and $X_2$ is T or A, or SYWIN (SEQ ID NO: 7); heavy-chain CDR2 is YPGSYIP (SEQ ID NO: 2); heavy-chain CDR3 is GYFDV (SEQ ID NO: 3); light-chain CDR1 is KSSQSLLXSGNQKNYLA (SEQ ID NO: 4), wherein X is N or S; light-chain CDR2 is GASTRES (SEQ ID NO: 5); and light-chain CDR3 is QNDHSYPYT (SEQ ID NO: 6).

According to some embodiments, the humanized antibody comprises heavy-chain CDR1 GYTFTSY (SEQ ID NO: 13).

According to specific embodiments, the humanized antibody comprises light-chain CDR1 KSSQSLLSSGNQKNYLA (SEQ ID NO: 15).

According to certain embodiments, the humanized antibody or the antibody fragment comprises a set of six CDRs wherein: heavy-chain CDR1 is GYTFTSY (SEQ ID NO: 13); heavy-chain CDR2 is YPGSYIP (SEQ ID NO: 2); heavy-chain CDR3 is GYFDV (SEQ ID NO: 3); light-chain CDR1 is KSSQSLLSSGNQKNYLA (SEQ ID NO: 15); light-chain CDR2 is GASTRES (SEQ ID NO: 5); and light-chain CDR3 is QNDHSYPYT (SEQ ID NO: 6).

According to some embodiments, the humanized antibody comprises a heavy chain variable region sequence selected from the group consisting of: SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO: 39, or an analog or derivative thereof having at least 90% sequence identity with the heavy chain variable region sequence. Each possibility represents a separate embodiment of the invention.

According to some embodiments, the humanized antibody comprises a light chain variable region sequence selected from the group consisting of: SEQ ID NO: 40, SEQ ID NO: 41, and SEQ ID NO: 42, or an analog or derivative thereof having at least 90% sequence identity with the heavy chain variable region sequence. Each possibility represents a separate embodiment of the invention.

According to some embodiments, the humanized antibody comprises a heavy chain variable region sequence selected from the group consisting of: SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO: 39, and a light chain variable region sequence selected from the group consisting of: SEQ ID NO: 40, SEQ ID NO: 41, and SEQ ID NO: 42, or an analog or derivative thereof having at least 95% sequence identity with the variable region sequences.

According to some embodiments, the humanized antibody comprises a heavy chain and a light chain, wherein said chains comprises a set of a heavy chain variable region sequence and a light chain variable region sequence, said set is selected from the group consisting of:

i. SEQ ID NOs: 39 and 40 (denoted antibody H11K1);

ii. SEQ ID NOs: 39 and 41 (denoted antibody H11K2); and iii. SEQ ID NOs: 39 and 42 (denoted antibody H11K3).

According to some embodiments, a conjugate comprising the antibody or fragment thereof as described herein is provided.

A conjugate according to some embodiments of the present invention comprises an antibody or fragment thereof defined above, attached directly or through a spacer or a linker to a moiety including but not limited to, a radioactive moiety, a labeling tag and a cytotoxic moiety.

Polynucleotide sequences encoding antibodies, having high affinity and specificity for human CD112R, as well as vectors and host cells carrying these polynucleotide sequences, are provided according to another aspect of the present invention.

According to some embodiments, polynucleotide sequences encoding the amino acid sequences of heavy chain variable region and light chain variable region described above are provided.

According to some embodiments, the polynucleotide sequence encodes an antibody or antibody fragment comprising the sequence set forth in a sequence selected from the group consisting of: (i) SEQ ID NO: 16 and SEQ ID NO: 18; (ii) SEQ ID NO: 20 and SEQ ID NO: 22; and (iii) SEQ ID NO: 24 and SEQ ID NO: 25, or an analog or derivative thereof having at least 90% sequence identity with the variable region sequences. Each possibility represents a separate embodiment of the present invention.

According to yet some embodiments, the polynucleotide sequence according to the invention encodes an antibody or antibody fragment or chain comprising a set of six CDRs wherein: heavy-chain CDR1 is $GYX_1FX_2SY$ (SEQ ID NO: 1) wherein $X_1$ denotes N, D, A, Q, S, or T; and $X_2$ is T or A or SYWIN (SEQ ID NO: 7); heavy-chain CDR2 is YPGSYIP (SEQ ID NO: 2); heavy-chain CDR3 is GYFDV (SEQ ID NO: 3); light-chain CDR1 is KSSQSLLXSGNQKNYLA (SEQ ID NO: 4) wherein X denotes N or S; light-chain CDR2 is GASTRES (SEQ ID NO: 5); and light-chain CDR3 is QNDHSYPYT (SEQ ID NO: 6).

According to yet some embodiments, the polynucleotide sequence according to the invention encodes an antibody or antibody fragment comprising a set of six CDRs wherein: heavy chain CDR1 sequence comprising the sequence GYTFTSY (SEQ ID NO: 13), heavy chain CDR2 comprising the sequence YPGSYIP (SEQ ID NO: 2), heavy chain CDR3 comprising the sequence GYFDV (SEQ ID NO: 3), light chain CDR1 comprising the sequence KSSQSLLSSGNQKNYLA (SEQ ID NO: 15), light chain CDR2 comprising the sequence GASTRES (SEQ ID NO: 5), and light chain CDR3 comprising the sequence QNDHSYPYT (SEQ ID NO: 6).

According to some embodiments, the polynucleotide sequences defined above encode a molecule selected from the group consisting of: an antibody, an antibody fragment comprising at least an antigen-binding portion, an antibody chain, and an antibody conjugate comprising said antibody or antibody fragment. Each possibility represents a separate embodiment of the present invention.

According to some embodiments, the polynucleotide sequence encodes a monoclonal antibody heavy chain variable region comprising a sequence set forth in SEQ ID NO: 16 or a variant thereof having at least 90% sequence identity.

According to some embodiments, the polynucleotide sequence encodes a monoclonal antibody heavy chain variable region, comprising a sequence set forth in SEQ ID NO: 20, or a variant thereof having at least 90% sequence identity.

According to some embodiments, the polynucleotide sequence encodes a monoclonal antibody heavy chain variable region, comprising a sequence set forth in SEQ ID NO: 24, or a variant thereof having at least 90% sequence identity.

According to some embodiments, the polynucleotide sequence encodes a monoclonal antibody light chain variable region comprising a sequence set forth in SEQ ID NO: 18 or a variant thereof having at least 90% sequence identity.

According to some embodiments, the polynucleotide sequence encodes a monoclonal antibody light chain variable region comprising a sequence set forth in SEQ ID NO: 22, or a variant thereof having at least 90% sequence identity.

According to some embodiments, the polynucleotide sequence encodes a monoclonal antibody light chain variable region comprising a sequence set forth in SEQ ID NO: 25, or a variant thereof having at least 90% sequence identity.

The present invention provides, according to some embodiments, a polypeptide comprising at least one sequence encoded by at least one polynucleotide sequence disclosed above.

In a further aspect, the present invention provides a nucleic acid construct comprising a nucleic acid molecule encoding at least one antibody chain or fragment thereof as described herein. According to some embodiments the nucleic acid construct is a plasmid.

According to some embodiments the plasmid comprises at least one polynucleotide sequence set forth in a sequence selected from the group consisting of SEQ ID NO: 16, SEQ ID NO: 18, SEQ ID NO: 20, SEQ ID NO: 22, SEQ ID NO: 24 and SEQ ID NO: 25. Each possibility represents a separate embodiment of the present invention.

In still another aspect the present invention provides a cell capable of producing an antibody or an antibody fragment comprising the specific CDR sequences and/or specific heavy and light chain variable regions described herein.

According to some embodiments, a cell, or a population of cells is provided comprising at least one polynucleotide sequence disclosed above.

According to some embodiments, the cell producing the monoclonal antibody is a hybridoma cell.

The present invention provides, according to another aspect, a pharmaceutical composition comprising as an active ingredient, at least one antibody, antibody fragment or conjugates thereof, as described herein, and optionally at least one pharmaceutical acceptable excipient, diluent, salt, or carrier.

According to some embodiments, the pharmaceutical composition comprises at least one antibody comprising a set of six CDRs wherein: heavy-chain CDR1 is GY$X_1$F$X_2$SY (SEQ ID NO: 1) wherein $X_1$ denotes N, D, A, Q, S, or T; and $X_2$ is T or A or SYWIN (SEQ ID NO: 7); heavy-chain CDR2 is YPGSYIP (SEQ ID NO: 2); heavy-chain CDR3 is GYFDV (SEQ ID NO: 3); light-chain CDR1 is KSSQSLLXSGNQKNYLA (SEQ ID NO: 4) wherein X denotes N or S; light-chain CDR2 is GASTRES (SEQ ID NO: 5); and light-chain CDR3 is QNDHSYPYT (SEQ ID NO: 6).

According to some embodiments, the pharmaceutical composition comprises an antibody or fragment thereof, comprising a heavy-chain CDR1 sequence GY$X_1$F$X_2$SY (SEQ ID NO: 1), wherein $X_2$ is T. According to some embodiments, the pharmaceutical composition comprises an antibody or fragment thereof, comprising a heavy-chain CDR1 sequence GYTFTSY (SEQ ID NO: 13). According to other embodiments, the pharmaceutical composition comprises an antibody or fragment thereof, comprising a heavy-chain CDR1 sequence GYNFASY (SEQ ID NO: 14). According to certain embodiments, the pharmaceutical composition comprises an antibody or fragment thereof, comprising a heavy-chain CDR1 sequence SYWIN (SEQ ID NO: 7).

According to some embodiments, the pharmaceutical composition comprises an antibody or fragment thereof, comprising a light-chain CDR1 sequence KSSQSLLSSGNQKNYLA (SEQ ID NO: 15).

According to some embodiments, the pharmaceutical composition comprises an antibody or antibody fragment comprising a set of six CDRs wherein: heavy chain CDR1 sequence comprising the sequence GYTFTSY (SEQ ID NO: 13), heavy chain CDR2 comprising the sequence YPGSYIP (SEQ ID NO: 2), heavy chain CDR3 comprising the sequence GYFDV (SEQ ID NO: 3), light chain CDR1 comprising the sequence KSSQSLLSSGNQKNYLA (SEQ ID NO: 15), light chain CDR2 comprising the sequence GASTRES (SEQ ID NO: 5), and light chain CDR3 comprising the sequence QNDHSYPYT (SEQ ID NO: 6).

According to some embodiments, the pharmaceutical composition comprises an antibody or fragment thereof comprising a heavy chain set forth in SEQ ID NO: 39.

According to some embodiments, the pharmaceutical composition comprises an antibody or fragment thereof comprising a light chain variable region having a sequence selected from the group consisting of SEQ ID NO: 40, SEQ ID NO: 41 and SEQ ID NO: 42. Each possibility represents a separate embodiment of the invention.

According to a specific embodiment, the pharmaceutical composition comprises an antibody or fragment thereof comprising a heavy chain variable region having the sequence set forth in SEQ ID NO: 39 and a light chain variable region having the sequence selected from the group consisting of SEQ ID NO: 40, SEQ ID NO: 41 and SEQ ID NO: 42.

Single chain variable fragment (scFv) molecules of the antibodies of the present invention are also provided. The scFv molecules comprise the antigen binding site of the antibody expressed in one polypeptide chain. According to some embodiments, the invention provides scFv molecules comprising a heavy chain and a light chain variable regions of the anti-CD112R antibodies. According to certain embodiments, the scFv comprises a hinge region between the two variable regions. According to specific embodiments, the scFv comprises the heavy and light chains of the humanized antibodies described herein.

According to some embodiments, the scFv comprises a CD112R binding site comprising six CDR sequences selected from the group consisting of:

i. three complementarity determining regions (CDRs) of a heavy-chain variable region comprising SEQ ID NO: 28 and three CDRs of a light-chain variable comprising SEQ ID NO: 26, or an analog or derivative thereof having at least 90% sequence identity with said antibody or fragment sequence; and ii. three CDRs of a heavy-chain variable region comprising SEQ ID NO: 17 and three CDRs of a light-chain variable region comprising SEQ ID NO: 19, or an analog or derivative thereof having at least 90% sequence identity with said antibody or fragment sequence.

According to some embodiments, the scFv comprises a CD112R binding site comprising a set of six CDRs wherein: heavy-chain CDR1 is $GYX_1FX_2SY$ (SEQ ID NO: 1) wherein $X_1$ denotes N, D, A, Q, S, or T; and $X_2$ is T or A or SYWIN (SEQ ID NO: 7); heavy-chain CDR2 is YPGSYIP (SEQ ID NO: 2); heavy-chain CDR3 is GYFDV (SEQ ID NO: 3); light-chain CDR1 is KSSQSLLXSGNQKNYLA (SEQ ID NO: 4) wherein X denotes N or S; light-chain CDR2 is GASTRES (SEQ ID NO: 5); and light-chain CDR3 is QNDHSYPYT (SEQ ID NO: 6).

According to some embodiments, the scFv comprises a heavy-chain CDR1 sequence $GYX_1FX_2SY$ (SEQ ID NO: 1), wherein $X_2$ is T. According to some embodiments, the scFv comprises heavy-chain CDR1 sequence GYTFTSY (SEQ ID NO: 13). According to other embodiments, the scFv comprises a heavy-chain CDR1 sequence GYNFASY (SEQ ID NO: 14). According to certain embodiments, the scFv comprises a heavy-chain CDR1 sequence SYWIN (SEQ ID NO: 7).

According to some embodiments, the scFv comprises a light-chain CDR1 sequence KSSQSLLSSGNQKNYLA (SEQ ID NO: 15).

According to some embodiments, the scFv comprises a set of six CDRs wherein: heavy chain CDR1 sequence comprising the sequence GYTFTSY (SEQ ID NO: 13), heavy chain CDR2 comprising the sequence YPGSYIP (SEQ ID NO: 2), heavy chain CDR3 comprising the sequence GYFDV (SEQ ID NO: 3), light chain CDR1 comprising the sequence KSSQSLLSSGNQKNYLA (SEQ ID NO: 15), light chain CDR2 comprising the sequence GASTRES (SEQ ID NO: 5), and light chain CDR3 comprising the sequence QNDHSYPYT (SEQ ID NO: 6).

According to some embodiments, the scFv comprises a heavy chain variable region sequence selected from the group consisting of SEQ ID NOs: 29-39.

According to some embodiments, the scFv comprises a light chain variable region sequence selected from the group consisting of SEQ ID NOs: 40-42.

According to some embodiments, the scFv comprises a linker connecting the heavy chain and light chain variable regions. According to some embodiments, the linker is a glycine-serine (GlySer) linker. According to some embodiments, the linker comprises $(GS)_n$, $(GSGGS)_n$, $(GGGS)_n$ or $(GGGGS)_n$, where n is an integer selected from 1, 2, 3, 4, 5, 6, 7, 8, 9 or 10. According to some embodiments, the linker comprises 2-6 repeats of the sequence GGGS According to certain exemplary embodiments, a linker comprising three or four repeats of the sequence GGGS connects the two variable regions within the scFv. According to some embodiments, the heavy chain variable region is on the N-terminal side of the scFv and is connected by the linker $(GGGS)_3$ to the light chain variable region. According to some embodiments, the light chain variable region is on the N-terminal side of the scFv and is connected by the linker $(GGGS)_4$ to the heavy chain variable region.

According to some embodiments, the scFv comprises a sequence selected from the group consisting of SEQ ID NOs: 43 to 54, or an analog or derivative thereof having at least 90% sequence identity with said antibody. Each possibility represents a separate embodiment of the invention.

According to some embodiments, the scFv comprises a sequence selected from the group consisting of SEQ ID NOs: 43 to 54. According to certain embodiments, the scFv consist of a sequence selected from the group consisting of SEQ ID NOs: 43 to 54.

According to some embodiments, the scFv is connected to a human Fc region to form scFv-Fc. According to some embodiments, the Fc is of human IgG1.

Also provided are pharmaceutical compositions, comprising at least one antibody, antibody fragment, or antibody conjugate according to the invention, for use in restoring NK cytotoxicity by inhibiting binding of CD112R, expressed on NK cells, to Nectin-2 (CD112).

According to other embodiments, the antibody or antibody fragment is capable of inhibiting binding of human CD112R, expressed on T-cells, to Nectin-2.

According to some embodiments, the pharmaceutical composition comprises at least one antibody, antibody fragment, or antibody conjugate according to the invention and an antibody against PD-1. According to some embodiments, the pharmaceutical composition comprises at least one antibody, antibody fragment, or antibody conjugate according to the invention and an antibody against TIGIT. According to some embodiments, the pharmaceutical composition comprises at least one antibody, antibody fragment, or antibody conjugate according to the invention and an antibody against PVR. According to some embodiments, the pharmaceutical composition comprises at least one antibody, antibody fragment, or antibody conjugate according to the invention and an antibody against CTLA-4.

According to some embodiments, the pharmaceutical composition according to the present invention is for use in cancer immunotherapy or in enhancing immune responses.

According to some embodiments of the invention, the cancer is selected from the group consisting of a lung cancer, a breast cancer, a colorectal cancer, a melanoma, an ovarian cancer, a pancreatic cancer, a colon cancer, a cervical cancer, a kidney cancer, a thyroid cancer, a prostate cancer, a brain cancer, a renal cancer, a throat cancer, a laryngeal carcinoma, a bladder cancer, a hepatic cancer, a fibrosarcoma, an endometrial cells cancer, a glioblastoma, sarcoma, a myeloid, a leukemia and a lymphoma. Each possibility represents a separate embodiment of the invention.

According to some embodiments, the cancer is a solid cancer. According to some specific embodiments, the solid cancer is selected from the group consisting of breast cancer, lung cancer, bladder cancer, pancreatic cancer and ovarian cancer.

According to some embodiments, the cancer is lung adenocarcinoma. According to some embodiments, the cancer is breast adenocarcinoma. According to some embodiments, the cancer is a colorectal cancer.

According to certain embodiments, the cancer is selected from the group consisting of: breast cancer, colorectal cancer, lung cancer, kidney cancer, melanoma, prostate cancer, and brain cancer. Each possibility represents a separate embodiment of the invention.

According to other embodiments, the cancer is hematologic cancer. According to some embodiments, the hematological cancer is selected from leukemia, lymphoma and multiple myeloma. Each possibility represents a separate embodiment of the invention.

According to some embodiments, the pharmaceutical composition is for use of treating cancer, together with human lymphocytes.

According to some embodiments, the human lymphocytes are killer cells selected from the group consisting of: T cells, NK cells and NKT cells. Each possibility represents a separate embodiment of the invention.

According to some embodiments, the killer cells are autologous or allogenic.

According to some embodiments, the pharmaceutical composition is for use in treating a viral infection.

According to certain embodiments, the pharmaceutical composition is for use in treating chronic infections. According to exemplary embodiments, the pharmaceutical composition is for use in treating a viral infection selected from the group consisting of hepatitis C viral infection (HCV), polyomavirus (JCV) infection and BK-virus (BKV) infection.

According to yet another aspect, the present invention provides a method of inhibiting binding of human CD112R to Nectin-2 by using a monoclonal antibody or antibody fragment defined herein.

According to an additional aspect, the present invention provides a method for enhancing immune response in a subject in need thereof comprising administering to said subject a therapeutically effective amount of an antibody or antibody fragment or as described herein.

According to yet another aspect, the present invention provides a method of treating cancer comprising administering to a subject in need thereof, a pharmaceutical composition comprising a therapeutically effective amount of the antibody or antibody fragment thereof described herein.

According to yet another aspect, the present invention provides a method of treating cancer comprising administering to a subject in need thereof, a therapeutically effective amount of the antibody or antibody fragment thereof against CD112R as described herein; and a therapeutically effective amount of an antibody against PD-1, TIGIT, or PVR. Each possibility represents a separate embodiment of the invention. The administration of the anti-CD112R antibody and the anti PD-1, TIGIT or PVR may be combined administration or sequential administration in any order of administration.

According to some embodiments of the invention, the therapeutically effective amount results in a decrease in tumor size or in the number of metastases in the subject.

According to some embodiments, the method of treating cancer comprises administering or performing at least one additional anti-cancer therapy. According to certain embodiments, the additional anticancer therapy is surgery, chemotherapy, radiotherapy, or immunotherapy.

According to some embodiments, the method of treating cancer comprises administration of the antibody and an additional anti-cancer agent. According to some embodiments, the additional anti-cancer agent is selected from the group consisting of: immune-modulator, agent that inhibits immune co-inhibitory receptor, activated lymphocyte cells, kinase inhibitor, and chemotherapeutic agent.

According to other embodiments, the additional immune-modulator is an antibody, antibody fragment or antibody conjugate that binds to human Nectin-2.

According to some embodiments, the additional immune-modulator is an antibody against an immune checkpoint molecule. According to some embodiments, the additional immune modulator is an antibody against an immune checkpoint molecule selected from the group consisting of human programmed cell death protein 1 (PD-1), PD-L1 and PD-L2, carcinoembryonic antigen-related cell adhesion molecule 1 (CEACAM1), lymphocyte activation gene 3 (LAG3), CD137, OX40 (also referred to as CD134), killer cell immunoglobulin-like receptors (KIR), TIGIT, PVR, CTLA-4, NKG2A, GITR, and any other checkpoint molecule or a combination thereof. Each possibility represents a separate embodiment of the invention.

According to certain embodiments, the additional immune modulator is an antibody against PD-1. According to certain embodiments, the additional immune modulator is an antibody against TIGIT. According to certain embodiments, the additional immune modulator is an antibody against PVR. According to some embodiments, the additional immune modulator is an antibody against CTLA-4.

According to some embodiments of the invention, the immune co-inhibitory receptor is selected from the group consisting of PD-1, TIGIT, PVR, CTLA-4, LAG3, TIM3, BTLA, VISTA, B7H4, CD96, BY55 (CD 160), LAIR1, SIGLEC10, and 2B4. Each possibility represents a separate embodiment of the invention.

According to some embodiments, the anti-cancer agent is selected from the group consisting of: erbitux, cytarabine, fludarabine, fluorouracil, mercaptopurine, methotrexate, thioguanine, gemcitabine, vincristine, vinblastine, vinorelbine, carmustine, lomustine, chlorambucil, cyclophosphamide, cisplatin, carboplatin, ifosfamide, mechlorethamine, melphalan, thiotepa, dacarbazine, bleomycin, dactinomycin, daunorubicin, doxorubicin, idarubicin, mitomycin, mitoxantrone, plicamycin, etoposide, teniposide and any combination thereof. Each possibility represents a separate embodiment of the invention.

According to some embodiments, the anti-cancer agent is epidermal growth factor receptor (EGFR) inhibitor. According to some embodiments, the EGFR inhibitor is selected from the group consisting of: Cetuximab (Erbitux®), Panitumumab (Vectibix®), and necitumumab (Portrazza®). Each possibility represents a separate embodiment of the invention.

According to some embodiments of the invention, the subject is a human subject.

According to some embodiments of the invention, the immune cell is a T cell.

According to an aspect, the present invention provides a method for modulating immune system function and/or activity comprising modulating the binding of CD112R to Nectin-2 using an antibody according to the invention.

According to some embodiments, the method of treating cancer involves preventing or reducing formation, growth or spread of metastases in a subject.

According to some embodiments, the method of treating cancer comprises administering to a subject in need thereof a pharmaceutical composition comprising an antibody or antibody fragment thereof, capable of inhibiting the binding of human CD112R to human Nectin-2, and further administrating to said subject human lymphocytes.

According to some embodiments, the human lymphocytes are killer cells selected from the group consisting of: T cells, NK cells and NKT cells.

According to some embodiments, the killer cells are autologous or allogenic.

The present invention also provides a method of preventing or treating a viral infection comprising administering to a subject the antibody or a fragment thereof comprising at least the antigen binding domain described herein, wherein said mAb or fragment thereof is capable of inhibiting binding of CD112R to Nectin-2.

The present invention further comprises, according to another aspect, a method of determining or quantifying CD112R in a sample, the method comprising contacting a biological sample with an antibody or antibody fragment, and measuring the level of complex formation, wherein the antibody or antibody fragment comprises:

i. a set of six CDRs wherein: heavy-chain CDR1 is $GYX_1FX_2SY$ (SEQ ID NO: 1) wherein $X_1$ denotes N, D, A, Q, S, or T; and $X_2$ denotes T or A or SYWIN (SEQ ID NO: 7); heavy-chain CDR2 is YPGSYIP (SEQ ID NO: 2); heavy-chain CDR3 is GYFDV (SEQ ID NO: 3); light-chain CDR1 is KSSQSLLXSGNQK-NYLA (SEQ ID NO: 4) wherein X denotes N or S; light-chain CDR2 is GASTRES (SEQ ID NO: 5); and light-chain CDR3 is QNDHSYPYT (SEQ ID NO: 6); or ii. a set of six CDRs wherein: heavy-chain CDR1 sequence is GYNFTSY (SEQ ID NO: 9) or SYWIN (SEQ ID NO: 7); heavy-chain CDR2 is FPGSYS (SEQ ID NO: 10); heavy-chain CDR3 is GYFDV (SEQ ID NO: 3); light-chain CDR1 is KSSQSLLNSGSQK-NYLA (SEQ ID NO: 11); light-chain CDR2 is GAS-TRES (SEQ ID NO: 5); and light-chain CDR3 is QNDHSYPYT (SEQ ID NO: 6).

According to some embodiments, the method comprising contacting a biological sample with an antibody or antibody fragment comprising a set of six CDRs wherein: heavy chain CDR1 sequence comprising the sequence GYTFTSY (SEQ ID NO: 13), heavy chain CDR2 comprising the sequence YPGSYIP (SEQ ID NO: 2), heavy chain CDR3 comprising the sequence GYFDV (SEQ ID NO: 3), light chain CDR1 comprising the sequence KSSQSLLSSGNQKNYLA (SEQ ID NO: 15), light chain CDR2 comprising the sequence GASTRES (SEQ ID NO: 5), and light chain CDR3 comprising the sequence QNDHSYPYT (SEQ ID NO: 6).

According to some embodiments, the method for detecting or quantifying the expression of CD112R comprises the steps of:

i. incubating a sample with an antibody specific to CD112R or an antibody fragment thereof comprising at least an antigen-binding portion; and ii. detecting the bound CD112R using a detectable probe.

According to some embodiments, the method further comprises the steps of:

iii. comparing the amount of (ii) to a standard curve obtained from a reference sample containing a known amount of CD112R; and iv. calculating the amount of the CD112R in the sample from the standard curve.

The antibodies according to the present invention may also be used to configure screening methods. For example, an enzyme-linked immunosorbent assay (ELISA), or a radioimmunoassay (RIA), as well as methods such as immunohistochemistry (IHC) or fluorescence-activated cell sorting (FACS), can be constructed for measuring levels of secreted or cell-associated CD112R in a biological sample, using the antibodies and methods known in the art.

According to some embodiments, the biological sample is a body fluid or tissue. According to additional embodiment, the sample is body tissue sample.

According to some embodiments, the method is performed in-vitro or ex-vivo.

According to an aspect, the present invention provides a method of diagnosing or prognosing cancer in a subject, the method comprising determining the expression level of CD112R in a biological sample of said subject using at least one antibody as described herein.

A kit for measuring the expression or presence of CD112R in biological sample is also provided comprising at least one antibody or antibody fragment according to the present invention. According to some embodiments, the kit comprises an antibody or antibody fragment comprising:

i. a set of six CDRs wherein: heavy-chain CDR1 is $GYX_1FX_2SY$ (SEQ ID NO: 1) wherein $X_1$ denotes N, D, A, Q, S, or T; and $X_2$ denotes T or A or SYWIN (SEQ ID NO: 7); heavy-chain CDR2 is YPGSYIP (SEQ ID NO: 2); heavy-chain CDR3 is GYFDV (SEQ ID NO: 3); light-chain CDR1 is KSSQSLLXSGNQK-NYLA (SEQ ID NO: 4) wherein X denotes N or S; light-chain CDR2 is GASTRES (SEQ ID NO: 5); and light-chain CDR3 is QNDHSYPYT (SEQ ID NO: 6); or ii. a set of six CDRs wherein: heavy-chain CDR1 sequence is GYNFTSY (SEQ ID NO: 9) or SYWIN (SEQ ID NO: 7); heavy-chain CDR2 is FPGSYS (SEQ ID NO: 10); heavy-chain CDR3 is GYFDV (SEQ ID NO: 3); light-chain CDR1 is KSSQSLLNSGSQK-NYLA (SEQ ID NO: 11); light-chain CDR2 is GAS-TRES (SEQ ID NO: 5); and light-chain CDR3 is QNDHSYPYT (SEQ ID NO: 6).

According to some embodiments, the kit comprises an antibody or antibody fragment comprising a set of six CDRs wherein: heavy chain CDR1 sequence comprising the sequence GYTFTSY (SEQ ID NO: 13), heavy chain CDR2 comprising the sequence YPGSYIP (SEQ ID NO: 2), heavy chain CDR3 comprising the sequence GYFDV (SEQ ID NO: 3), light chain CDR1 comprising the sequence KSSQSLLSSGNQKNYLA (SEQ ID NO: 15), light chain CDR2 comprising the sequence GASTRES (SEQ ID NO: 5), and light chain CDR3 comprising the sequence QNDHSYPYT (SEQ ID NO: 6).

Any embodiment disclosed herein above can optionally be combined with the subject matter of one or any combination of another embodiment disclosed herein. Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A—PVRIG transcript levels from Database of Immune Cell Expression (DICE). FIG. 1B—resting PBMCs had no detectable levels of CD112R; FIG. 1C—robust expression of CD112R was seen on T cells following 96 hours activation of PBMCs; FIG. 1D—robust expression of CD112R by activated NK cells. Filled histograms depict background staining. The two empty histograms, at each graph, represent staining by two anti-CD112R mAb clones (#13 and #15). Shown are results obtained for two independent healthy donors.

FIGS. 3A-3C provide analysis of binding and blocking of some of the anti CD112R mAbs of the present invention. FIG. 3A illustrates specific binding, determined by FACS analysis, of anti-CD112R mAb clones to 293T cells that overexpress CD112R and not to parental cells. FIG. 3B—Calculated EC-50 values: CD112R chimeric mAbs were used in concentration from 99-0.4 nM in series of three-fold dilutions and incubated with HEK 293T cells (Human embryonic kidney 293 cells) that overexpress CD112R. For detection, anti-human-APC antibody (Ab) was used at 1:200 dilution, and cell binding was analyzed by FACS. FIG. 3C—8866 cells (chronic myelogenous leukemia cells) overexpressing human Nectin-2 were incubated with 10 μg/ml of CD112R-Fc in the presence of isotype control Ab, or with the indicated clones at 4 μg/ml. Bound CD112R-Fc was detected by anti-mouse-Dy-647 1:250 dilution and analyzed by FACS. The blocking of CD112R binding exceeded 95% by all the variants.

FIGS. 4A and 4B) and MDA-MB-231 (breast adenocarcinoma; FIG. 4C). FIG. 4A—The activity of anti-CD112R with murine IgG1 Fc (mIgG1, inert Fc with no detectable binding to human CD16) was compared to a chimeric clone with the same Fabs, and to the chimeric clone VH0K0 comprising N31S (also denoted herein N27dS according to the Kabat numbering), both having human IgG1 Fc (hIgG1, effector Fc capable of activating human CD16). FIG. 4B-4C—The anti-CD112R mAbs activity was compared to that of a combination of the antibody with anti-immune check point inhibitor (ICI) antibodies, namely, anti-TIGIT (VSIG #9, described in WO2017037707) and anti-PVR (named NTX-1088) mAbs, as indicated. * $p<0.03$,  $p<0.001$, * $p<0.0001$ by two tailed student t-test. Representative data for two out of five donors is shown.

FIG. 7A—treatment of NK cells, cultured with MDA-MB-231 (breast adenocarcinoma) cells with selected humanized anti-CD112R antibodies. FIG. 7B—a comparison of treatment of the above cell culture with various humanized anti-CD112R mAb and with anti-PVR mAb (NTX-1088) as standalone or in combination ($p<0.03$; black bars).

FIG. 8A—Dose response assay of all the humanized variants and a reference anti-CD112R Ab (Ref) from 4-0.0625 ug/ml. FIG. 8B—Selected humanized variants were tested in a range of concentrations from 26.4-0.1 nM and the reference anti-CD112R Ab was added only at the highest 24.6 nM concentration. Comparison was done to the highest concentration of hIgG1.

DETAILED DESCRIPTION OF THE INVENTION

Figure 1A:
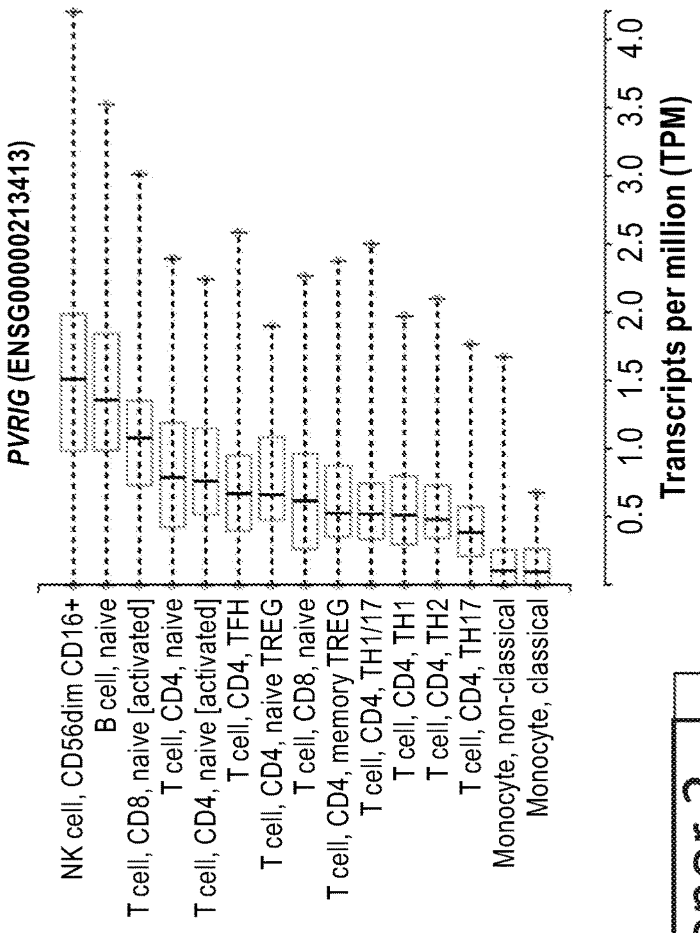
FIGS. 1A-ID depict the expression levels of CD112R on various immune cells.

The present invention provides effective antibodies, including chimeric and humanized mAbs and fragments thereof, specific to the human protein CD112R. The invention also provides production and use of the antibodies as therapeutic agents. In some embodiments, the invention provides antibodies specific to CD112R for efficient restoration of immune activity against cancer cells overexpressing Nectin-2, and for treatment of cancer as a stand-alone treatment or in combination with other therapies, e.g., with additional immune checkpoint inhibitors. In some embodiments, the antibodies described herein are for use in treating viral infections.

The present invention further provides humanized antibodies specific to the human CD112R. Advantageously, the antibodies of the invention are humanized, thus avoiding the risk of adverse immune response towards the antibodies and are therefore safe for in-vivo use in humans.

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments. As used herein the term "about" refers to an amount that is near the stated amount by 10% or less.

The term "CD112R" or "PVRIG" as used herein refers to a human cell surface receptor for Nectin-2, also known as C7orf15. PVRIG stands for Poliovirus receptor-related immunoglobulin domain-containing protein. The protein, following interaction with Nectin-2, inhibits T-cell proliferation. An exemplary CD112R protein or gene encoding to the protein according to the invention is set forth in Swiss-Port, UniPort and GenBank symbols or accession numbers: Gene ID: 79037, Q6DKI7, D6W5U9, Q9BVK3.

The antibodies or a fragment thereof according to the invention bind to an epitope in CD112R. Specifically, the antibodies bind to an epitope within the ectodomain (extracellular part) of the CD112R protein.

To generate the parent mAbs of the present invention, a recombinant fusion protein, comprising the extracellular part of human CD112R and a murine Fc region of an IgG protein as a carrier, was produced and purified. The resulted fusion protein hCD112R-Fc was used as an immunogen. BALB/c mice were injected with 50 μg of the immunogen in complete Freund's adjuvant, and 2 weeks later a boost injection was given using incomplete Freund's adjuvant. After 2 weeks, mice sera were screened for the antibody titer using ELISA. The best responders were further boosted with the immunogen in PBS. Three days later, spleen cells were collected, and after lysis of red blood cells, fused with SP2/0 myeloma cells. The cells were seeded in 20% RPMI 1640 medium containing hypoxanthine, aminopterine, and thymidine for hybridoma selection and screened for mAbs secretion using ELISA. Positive cell lines, i.e., cells secreting mAbs that recognize hCD112R-Fc, were further selected to develop a product that will have the following differentiating characteristics: a) lack of cross-reactivity to other ligands of related immune cell receptors (e.g., DNAM1 and TIGIT); b) strong binding to the native, mature human CD112R molecule expressed on the surface of living cells.

For the humanization of selected Ab clones, IGHV1-69*10 germline framework was selected for the heavy chain, and IGKV4-1*01 was selected for the light chain framework. Both are very well represented at the human germline, which is further supported by the high expression titer of the resulting humanized variants.

The CD112R serves as an antigen to the antibodies described herein. The term "antigen" as used herein refers to a molecule or a portion of a molecule capable of eliciting antibody formation and being specifically bound by an antibody. An antigen may have one or more than one epitope. The specific binding referred to above is meant to indicate that the antigen will react, in a highly selective manner, with its corresponding antibody and not with the multitude of other antibodies which may be evoked by other antigens. An antigen according to some embodiments of the present invention is a CD112R protein or an immunogenic portion thereof.

A binding affinity can be quantified using known methods such as, Surface Plasmon Resonance (SPR) (described in Scarano S, Mascini M, Turner A P, Minunni M. Surface plasmon resonance imaging for affinity-based biosensors. Biosens Bioelectron. 2010, 25: 957-66), and can be calculated using, e.g., a dissociation constant, Kd, such that a lower Kd reflects higher affinity.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (Fragment crystallizable) domains. The antigen binding domains, Fab, include regions where the polypeptide sequence varies. The term $F(ab')_2$ represents two Fab' arms linked together by disulfide bonds. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hyper-variable domains known as complementarity determining regions (CDRs 1-3). These domains contribute specificity and affinity of the antigen-binding site.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ). Both isotopes are found in all antibody classes.

The term "antibody" is used in the broadest sense and includes monoclonal antibodies (including full length or intact monoclonal antibodies), polyclonal antibodies, multivalent antibodies, chimeric antibodies, humanized antibodies and antibody fragments long enough to exhibit the desired biological activity, namely binding to human CD112R.

Antibody or antibodies according to the invention includes intact antibodies, such as polyclonal antibodies or monoclonal antibodies (mAbs), as well as proteolytic fragments thereof, such as the Fab or $F(ab')_2$ fragments. Single chain antibodies (e.g. scFv) also fall within the scope of the present invention.

Antibody Fragments

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) $F(ab')_2$ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., Proc. Natl. Acad. Sci. (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv).

Single chain antibodies can be single chain composite polypeptides having antigen binding capabilities and comprising amino acid sequences homologous or analogous to the variable regions of an immunoglobulin light and heavy chain i.e., linked $V_H$-$V_L$ or single chain Fv (scFv). Techniques for the production of single-chain antibodies (U.S. Pat. No. 4,946,778) can be adapted to produce single-chain antibodies to CD112R.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). Monoclonal antibodies may also be isolated from phage antibody libraries using the techniques described, for example, in Clackson et al., Nature 1991, 352, 624-628 or Marks et al., J. Mol. Biol., 1991, 222:581-597.

The mAbs of the present invention may be of any immunoglobulin class including IgG, IgM, IgE, IgA, and IgD.

Anti-idiotype antibodies specifically immunoreactive with the hypervariable regions of an antibody of the invention are also comprehended.

According to an aspect, the present invention provides an antibody or antibody fragment thereof comprising a set of six CDR sequences selected from the group consisting of:

i. three complementarity determining regions (CDRs) of a heavy-chain variable region comprising SEQ ID NO: 28 and three CDRs of a light-chain variable comprising SEQ ID NO: 26, or an analog or derivative thereof having at least 90% sequence identity with said antibody or fragment sequence; and
ii. three CDRs of a heavy-chain variable region comprising SEQ ID NO: 21 and three CDRs of a light-chain variable region comprising SEQ ID NO: 23, or an analog or derivative thereof having at least 90% sequence identity with said antibody or fragment sequence.

Sequence identity is the percentage of amino acids or nucleotides which match exactly between two different sequences. Sequence similarity permits conservative substitution of amino acids to be determined as identical amino acids. The polynucleotide sequences described herein may be codon-optimized for expression in specific cells, such as human cells. Codon optimization does not change the encoded amino acid sequences of the antibody's chain but may, for example, increase the expression in cells.

The invention also provides conservative amino acid variants of the antibody molecules according to the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved. The term "antibody analog" as used herein refers to an antibody derived from another antibody by one or more conservative amino acid substitutions.

The term "antibody variant" as used herein refers to any molecule comprising the antibody of the present invention. For example, fusion proteins in which the antibody or an antigen-binding-fragment thereof is linked to another chemical entity is considered an antibody variant.

Analogs and variants of the antibody sequences are also within the scope of the present application. These include, but are not limited to, conservative and non-conservative substitution, insertion and deletion of amino acids within the sequence. Such modification and the resultant antibody analog or variant are within the scope of the present invention as long as they confer, or even improve the binding of the antibody to the human CD112R.

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. These substitutions may enhance oral bioavailability, penetration, and targeting to specific cell populations, immunogenicity, and the like. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, according to one table known in the art, the following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

It should be emphasized that the variant chain sequences are determined by sequencing methods using specific primers. Different sequencing methods employed on the same sequence may result in slightly different sequences due to technical issues and different primers, particularly in the sequence terminals.

CDR identification or determination from a given heavy or light chain variable sequence, is typically made using one of few methods known in the art. For example, such determination is made according to the Kabat (Wu T. T and Kabat E. A., *J Exp Med,* 1970; 132:211-50), chothia and IMGT (Lefranc M-P, et al., *Dev Comp Immunol,* 2003, 27:55-77).

When the term "CDR having a sequence", or a similar term is used, it includes options wherein the CDR comprises the specified sequences and also options wherein the CDR consists of the specified sequence.

The antigen specificity of an antibody is based on the hyper variable region (HVR), namely the unique CDR sequences of both light and heavy chains that together form the antigen-binding site.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273, 927-948 ("Chothia" numbering scheme); MacCallum et al., *J. Mol. Biol.* 262:732-745 (1996), "Antibody-antigen interactions: Contact analysis and binding site topography," *J. Mol. Biol.* 262, 732-745." ("Contact" numbering scheme); Lefranc M P et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Whitelegg N R and Rees A R, "WAM: an improved algorithm for modelling antibodies on the WEB," Protein Eng. 2000 December; 13(12):819-24 ("AbM" numbering scheme. In certain embodiments the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Alterations (e.g., substitutions) may be made in CDRs, e.g., to improve antibody affinity. Such alterations may be made in CDR encoding codons with a high mutation rate during somatic maturation (See e.g., Chowdhury, Methods Mol. Biol. 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (See e.g., Hoogenboom et al. in Methods in Molecular Biology 178:1-37 (2001)). CDR residues involved in antigen binding may be specifically identified, e.g., using alanine scanning mutagenesis or modeling (See e.g., Cunningham and Wells Science, 244:1081-1085 (1989)). CDR-H3 and CDR-L3 in particular are often targeted. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

The terms "molecule having the antigen-binding portion of an antibody" and "antigen-binding-fragments" as used herein are intended to include not only intact immunoglobulin molecules of any isotype and generated by any animal cell line or microorganism, but also the antigen-binding reactive fraction thereof, including, but not limited to, the Fab fragment, the Fab' fragment, the $F(ab')_2$ fragment, the variable portion of the heavy and/or light chains thereof, Fab mini-antibodies (see e.g., WO 93/15210, U.S. patent application Ser. No. 08/256,790, WO 96/13583, U.S. patent application Ser. No. 08/817,788, WO 96/37621, U.S. patent application Ser. No. 08/999,554), and single-chain antibodies incorporating such reactive fraction, as well as any other type of molecule in which such antibody reactive fraction has been physically inserted. Such molecules may be provided by any known technique, including, but not limited to, enzymatic cleavage, peptide synthesis or recombinant techniques.

The antibodies herein specifically include "chimeric" antibodies in which a portion of the heavy and/or light chain is identical with or homologous to corresponding sequences in antibodies derived from a particular species, or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). In addition, complementarity determining region (CDR) grafting may be performed to alter certain properties of the antibody molecule including affinity or specificity. Antibodies that have variable region framework residues substantially from human antibody (termed an acceptor antibody) and CDRs substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 90/07861, WO 92/22653 and U.S. Pat. Nos. 5,693,762, 5,693,761, 5,585,089, 5,530,101 and 5,225,539).

According to some embodiments, the antibody is a monoclonal antibody.

According to some specific embodiments, the monoclonal antibody is a chimeric monoclonal antibody.

According to some embodiments, the chimeric antibody comprises human-derived constant regions.

According to some embodiments the human constant regions of the chimeric antibody are selected from the group consisting of: human IgG1, human IgG2, human IgG3, and human IgG4.

According to some embodiments the human constant regions of the chimeric antibody are selected from the group consisting of: human IgG1.

According to a particular embodiment, a chimeric monoclonal antibody which recognizes human CD112R is provided comprising:

i. a set of six CDRs wherein: heavy-chain CDR1 sequence is SEQ ID NO: 1 or SEQ ID NO: 7; heavy-chain CDR2 sequence is SEQ ID NO: 2 or SEQ ID NO: 8; heavy-chain CDR3 sequence is SEQ ID NO: 3; light-chain CDR1 sequence is SEQ ID NO: 4; light-chain CDR2 sequence is SEQ ID NO: 5; and light-chain CDR3 sequence is SEQ ID NO: 6; or ii. a set of six CDRs wherein: heavy-chain CDR1 sequence is SEQ ID NO: 9 or SEQ ID NO: 7; heavy-chain CDR2 sequence is SEQ ID NO: 10 or SEQ ID NO: 12; heavy-chain CDR3 sequence is SEQ ID NO: 3; light-chain CDR1 sequence is SEQ ID NO: 11; light-chain CDR2 sequence is SEQ ID NO: 5; and light-chain CDR3 sequence is SEQ ID NO: 6.

In some embodiments, an antibody provided herein may be further modified to contain additional nonproteinaceous moieties that are known and available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n vinyl pyrrolidone)polyethylene glycol, polypropylene glycol homopolymers, polypropylen oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if two or more polymers are attached, they can be the same or different molecules.

The antibodies described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors". Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

The nucleic acids encoding the antibodies described herein can be used to infect, transfect, transform, or otherwise render a suitable cell transgenic for the nucleic acid, thus enabling the production of antibodies for commercial or therapeutic uses. Standard cell lines and methods for the production of antibodies from a large-scale cell culture are known in the art. In certain embodiments, the cell is a Eukaryotic cell. In certain embodiments, the Eukaryotic cell is a mammalian cell. In certain embodiments, the mammalian cell is a cell line useful for producing antibodies is a Chines Hamster Ovary cell (CHO) cell, an NS0 murine myeloma cell, or a PER.C6® cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

Also described herein are methods of making the mAbs and fragments specific to CD112R of the present invention. Such methods comprise incubating a cell or cell-line comprising a nucleic acid encoding the antibody in a cell culture medium under conditions sufficient to allow for expression and secretion of the antibody, and further harvesting the antibody from the cell culture medium. The harvesting can further comprise one or more purification steps to remove live cells, cellular debris, non-antibody proteins or polypeptides, undesired salts, buffers, and medium components. In certain embodiments, the additional purification step(s) include centrifugation, ultracentrifugation, protein A, protein G, protein A/G, or protein L purification, and/or ion exchange chromatography.

According to one aspect, the present invention provides a mAb, or a fragment thereof comprising at least the antigen binding portion, which specifically binds to human CD112R, said antibody or fragment thereof have an affinity to human CD112R of at least $0.5\times10^{-9}$M.

In certain embodiments, the EC50 of a humanized mAb or antigen binding fragment thereof for binding human CD112R is less than about 0.5 nM, 0.1 nM, 0.05 nM, or 0.01 nM.

Half maximal effective concentration (EC50) refers to the concentration of the antibody that induces a response halfway between the baseline and maximum after a specified exposure time.

According to some embodiments, the mAb or mAb fragment comprises a set of six CDR sequences selected from the group consisting of:

i. three complementarity determining regions (CDRs) of a heavy-chain variable region comprising SEQ ID NO: 28 and three CDRs of a light-chain variable comprising SEQ ID NO: 26, or an analog or derivative thereof having at least 90% sequence identity with said antibody or fragment sequence; and
ii. three CDRs of a heavy-chain variable region comprising SEQ ID NO: 21 and three CDRs of a light-chain variable region comprising SEQ ID NO: 23, or an analog or derivative thereof having at least 90% sequence identity with said antibody or fragment sequence.

According to some specific embodiments the mAb or fragment comprises heavy chain CDR1 sequence comprising the amino acid sequence SY, heavy chain CDR2 comprising the sequence YPGSYIP (SEQ ID NO: 2), heavy chain CDR3 comprising the sequence GYFDV (SEQ ID NO: 3), light chain CDR1 comprising the sequence KSSQSLLXSGNQKNYLA (SEQ ID NO: 4) wherein X denotes N or S, light chain CDR2 comprising the sequence GASTRES (SEQ ID NO: 5), and light chain CDR3 comprising the sequence QNDHSYPYT (SEQ ID NO: 6), or analogs thereof comprising no more than 5% amino acid substitution, deletion and/or insertion in the hypervariable region (HVR) sequence.

According to some specific embodiments the mAb or fragment comprises heavy chain CDR1 sequence consists of the sequence $GYX_1FX_2SY$ (SEQ ID NO: 1) wherein $X_1$ denotes N, D, A, Q, S, or T; and $X_2$ denotes T or A or SYWIN (SEQ ID NO: 7), heavy chain CDR2 consists of the sequence YPGSYIP (SEQ ID NO: 2), heavy chain CDR3 consists of the sequence GYFDV (SEQ ID NO: 3), light chain CDR1 consists of the sequence KSSQSLLXSGNQKNYLA (SEQ ID NO: 4) wherein X denotes N or S, light chain CDR2 consists of the sequence GASTRES (SEQ ID NO: 5), and light chain CDR3 consists of the sequence QNDHSYPYT (SEQ ID NO: 6).

According to some embodiments, the antibodies are humanized antibodies.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. According to some embodiments, some FR residues in a humanized antibody are substituted with corresponding residues from a non-human antibody (e.g., the antibody from which the CDR residues are derived), e.g., to restore or improve antibody specificity or affinity.

A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Pharmacology and Methods of Treatments

In pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired exposure.

Typically, the antibodies and fragments and conjugates thereof of the present invention comprising the antigen binding portion of an antibody or comprising another polypeptide including a peptide-mimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as intravenously, orally, topically, intranasally, subcutaneously, intramuscularly, intra-arterially, intraarticulary, intralesionally, intratumorally or parenterally. Ordinarily, intravenous (i.v.) administration is used for delivering antibodies.

According to an aspect, the present invention provides a method of treating cancer comprising administering to a subject in need thereof, a therapeutically effective amount of a pharmaceutical composition comprising the antibody or antibody fragment thereof described herein.

As used herein the term "subject", "individual", or "patient" refers to individuals diagnosed with, suspected of being afflicted with, or at-risk of developing at least one disease for which the described compositions and method are useful for treating. According to some embodiments the individual is a mammal. According to some embodiments, the mammal is a mouse, rat, rabbit, dog, cat, horse, cow, sheep, pig, goat, llama, alpaca, or yak. According to some embodiments, the individual is a human.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered, its persistence in the blood circulation, and the judgment of the treating physician.

As used herein the term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The cancer amendable for treatment by the present invention includes, but is not limited to: carcinoma, lymphoma, blastoma, sarcoma, and leukemia or lymphoid malignancies. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high-grade immunoblastic NHL; high-grade lymphoblastic NHL; high-grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amendable for treatment of the invention include metastatic cancers.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The pharmaceutical composition according to the present invention may be administered together or with combination with an anti-neoplastic composition.

As used herein the term "combination" or "combination treatment" can refer either to concurrent administration of the articles to be combined or sequential administration of the articles to be combined. As described herein, when the combination refers to sequential administration of the articles, the articles can be administered in any temporal order.

The term "treatment" as used herein refers to both therapeutic treatment and prophylactic or preventative measures. Those in need of treatment include those already with the disorder as well as those in which the disorder is to be prevented.

The term "cancer" refers to or describes the physiological condition in mammals that is typically characterized by unregulated cell growth. Examples of cancer include but are not limited to, carcinoma, lymphoma, blastoma, sarcoma, and leukemia. More particular examples of such cancers include melanoma, lung, thyroid, breast, colon, prostate, hepatic, bladder, renal, cervical, pancreatic, leukemia, lymphoma, myeloid, ovarian, uterus, sarcoma, biliary, or endometrial cancer.

According to some embodiments, the method of treating cancer comprises administering the pharmaceutical composition as part of a treatment regimen comprising administration of at least one additional anti-cancer agent.

According to some embodiments, the anti-cancer agent is selected from the group consisting of an antimetabolite, a mitotic inhibitor, a taxane, a topoisomerase inhibitor, a topoisomerase II inhibitor, an asparaginase, an alkylating agent, an antitumor antibiotic, and combinations thereof. Each possibility represents a separate embodiment of the invention.

According to some embodiments, the antimetabolite is selected from the group consisting of cytarabine, fludarabine, fluorouracil, mercaptopurine, methotrexate, thioguanine, gemcitabine, and hydroxyurea. According to some embodiments, the mitotic inhibitor is selected from the group consisting of vincristine, vinblastine, and vinorelbine. According to some embodiments, the topoisomerase inhibitor is selected from the group consisting of topotecan and irinotecan. According to some embodiments, the alkylating agent is selected from the group consisting of busulfan, carmustine, lomustine, chlorambucil, cyclophosphamide, cisplatin, carboplatin, ifosfamide, mechlorethamine, melphalan, thiotepa, dacarbazine, and procarbazine. According to some embodiments, the antitumor antibiotic is selected from the group consisting of bleomycin, dactinomycin, daunorubicin, doxorubicin, idarubicin, mitomycin, mitoxantrone, and plicamycin. According to some embodiments, the topoisomerase II is selected from the group consisting of etoposide and teniposide. Each possibility represents a separate embodiment of the present invention.

According to some particular embodiments, the additional anti-cancer agent is selected from the group consisting of bevacizumab, carboplatin, cyclophosphamide, doxorubicin hydrochloride, gemcitabine hydrochloride, topotecan hydrochloride, thiotepa, and combinations thereof. Each possibility represents a separate embodiment of the present invention.

Monoclonal antibodies according to the present invention may be used as part of combined therapy with at least one anti-cancer agent. According to some embodiments, the additional anti-cancer agent is an immuno-modulator, an activated lymphocyte cell, a kinase inhibitor or a chemotherapeutic agent.

According to some embodiments, the anti-cancer agent is an immuno-modulator, whether agonist or antagonist, such as antibody against an immune checkpoint molecule.

Checkpoint immunotherapy blockade has proven to be an exciting new venue of cancer treatment. Immune checkpoint pathways consist of a range of co-stimulatory and inhibitory molecules which work in concert in order to maintain self-tolerance and protect tissues from damage by the immune system under physiological conditions. Tumors take advantage of certain checkpoint pathways in order to evade the immune system. Therefore, the inhibition of such pathways has emerged as a promising anti-cancer treatment strategy.

The anti-cytotoxic T lymphocyte 4 (CTLA-4) antibody ipilimumab (approved in 2011) was the first immunotherapeutic agent that showed a benefit for the treatment of cancer patients. The antibody interferes with inhibitory signals during antigen presentation to T cells. Anti-programmed cell death 1 (PD-1) antibody pembrolizumab (approved in 2014) blocks negative immune regulatory signaling of the PD-1 receptor expressed by T cells. An additional anti-PD-1 agent was filed for regulatory approval in 2014 for the treatment of non-small cell lung cancer (NSCLC). Active research is currently exploring many other immune checkpoints, among them: CEACAM1, NKG2A, B7-H3, B7-H4, VISTA, lymphocyte activation gene 3 (LAG3), CD137, OX40 (also referred to as CD134), and killer cell immunoglobulin-like receptors (KIR).

According to some specific embodiments, the immuno-modulator is selected from the group consisting of: an antibody inhibiting CTLA-4, an anti-human programmed cell death protein 1 (PD-1), PD-L1 and PD-L2 antibody, an activated cytotoxic lymphocyte cell, a lymphocyte activating agent, an antibody against CEACAM, an antibody against TIGIT, and a RAF/MEK pathway inhibitor. Each possibility represents a separate embodiment of the present invention. According to some specific embodiments, the additional immuno-modulator is selected from mAb to PD-1, mAb to PD-L1, mAb to PD-L2, mAb to CEACAM1, mAb to CTLA-4, mAb to TIGIT, mAb to PVR, Interleukin 2 (IL-2) or lymphokine-activated killer (LAK) cell.

In certain embodiments, the inhibitor of PD-1 signaling is an antibody or fragment thereof that binds to PD-1. In certain embodiments, the antibody or fragment thereof that binds to PD-1 is Pembrolizumab, Nivolumab, AMP-514, Tislelizumab, Spartalizumab, or a PD-1 binding fragment thereof. In certain embodiments, the inhibitor of PD-1 signaling is an antibody that specifically binds PD-L-1 or PD-L-2. In certain embodiments, the antibody that specifically binds PD-L1 or PD-L2 comprises Durvalumab, Atezolizumab, Avelumab, BMS-936559, or FAZ053, or a PD-L1 or PD-L2 binding fragment thereof. In certain embodiments, the inhibitor of PD-1 signaling comprises an Fc-fusion protein that binds PD-1, PD-L1, or PD-L2. In certain embodiments, the Fc-fusion protein comprises AMP-224 or a PD-1 binding fragment thereof. In certain embodiments, the inhibitor of PD-1 signaling comprises a small molecule inhibitor of PD-1, PD-L1, or PD-L2. In certain embodiments, the small molecule inhibitor of PD-1, PD-L1, or PD-L2 signaling comprises on or more of: N-{2-[({2-methoxy-6-[(2-methyl[1,1'-biphenyl]-3-yl)methoxy]pyridin-3-yl}methyl)amino]ethyl}acetamide (BMS 202); (2-((3-cyanobenzyl)oxy)-4-((3-(2,3-dihydrobenzo[b][1,4]dioxin-6-yl)-2-methylbenzyl)oxy)-5-methylbenzyl)-D-serine hydrochloride; (2R,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid; 3-(4,6-dichloro-1,3,5-triazin-2-yl)-1-phenylindole; 3-(4,6-dichloro-1,3,5-triazin-2-yl)-1-phenyl-1h-indole; L-α-Glutamine, N2,N6-bis(L-seryl-L-asparaginyl-L-threonyl-L-seryl-L-α-glutamyl-L-seryl-L-phenylalanyl)-L-lysyl-L-phenylalanyl-L-arginyl-L-valyl-L-threonyl-L-glutaminyl-L-leucyl-L-alanyl-L-prolyl-L-lysyl-L-alanyl-L-glutaminyl-L-isoleucyl-L-lysyl; (2S)-1-[[2,6-dimethoxy-4-[(2-methyl[1,1'-biphenyl]-3-yl)methoxy]phenyl]methyl]-2-piperidinecarboxylic acid; Glycinamide, N-(2-mercaptoacetyl)-L-phenylalanyl-N-methyl-L-alanyl-L-asparaginyl-L-prolyl-L-histidyl-L-leucyl-N-methylglycyl-L-tryptophyl-L-seryl-L-tryptophyl-N-methyl-L-norleucyl-N-methyl-L-norleucyl-L-arginyl-L-cysteinyl-, cyclic (1→14)-thioether; or a derivative or analog thereof.

According to other embodiments the additional anti-cancer agent is a chemotherapeutic agent. The chemotherapy agent, which could be administered together with the antibody according to the present invention, or separately, may comprise any such agent known in the art exhibiting anticancer activity, including but not limited to: mitoxantrone, topoisomerase inhibitors, spindle poison from vinca: vinblastine, vincristine, vinorelbine (taxol), paclitaxel, docetaxel; alkylating agents: mechlorethamine, chlorambucil, cyclophosphamide, melphalan, ifosfamide; methotrexate; 6-mercaptopurine; 5-fluorouracil, cytarabine, gemcitabine; podophyllotoxins: etoposide, irinotecan, topotecan, dacarbazine; antibiotics: doxorubicin (adriamycin), bleomycin, mitomycin; nitrosoureas: carmustine (BCNU), lomustine, epirubicin, idarubicin, daunorubicin; inorganic ions: cisplatin, carboplatin; interferon, asparaginase; hormones: tamoxifen, leuprolide, flutamide, and megestrol acetate.

According to some embodiments, the chemotherapeutic agent is selected from alkylating agents, antimetabolites, folic acid analogs, pyrimidine analogs, purine analogs and related inhibitors, vinca alkaloids, epipodophyllotoxins, antibiotics, L-asparaginase, topoisomerase inhibitor, interferons, platinum coordination complexes, anthracenedione substituted urea, methyl hydrazine derivatives, adrenocortical suppressant, adrenocorticosteroids, progestins, estrogens, antiestrogen, androgens, antiandrogen, and gonadotropin-releasing hormone analog. According to another embodiment, the chemotherapeutic agent is selected from the group consisting of 5-fluorouracil (5-FU), leucovorin (LV), irinotecan, oxaliplatin, capecitabine, paclitaxel and docetaxel. One or more chemotherapeutic agents can be used.

In some embodiments, the pharmaceutical composition according to the present invention is for use in treating cancer or for use in enhancing the immune response.

The term "enhancing immune response" refers to increasing the responsiveness of the immune system and inducing or prolonging its memory. The pharmaceutical composition according to the present invention may be used to stimulate immune system upon vaccination. Thus, in one embodiment the pharmaceutical composition can be used for improving vaccination.

In certain embodiments, the cancer is selected from lung, thyroid, breast, colon, melanoma, prostate, hepatic, bladder, renal, cervical, pancreatic, leukemia, lymphoma, myeloid, ovarian, uterus, sarcoma, biliary, and endometrial cells cancer. Each possibility represents a separate embodiment of the invention.

According to some embodiments, a pharmaceutical composition, comprising at least one antibody or fragment thereof according to the present invention, and a pharmaceutical composition, comprising an additional immunomodulator or a kinase inhibitor, are used in treatment of cancer by separate administration.

According to still another aspect the present invention provides a method of treating cancer in a subject in need thereof comprising administering to said subject a therapeutically effective amount of an antibody or antibody fragment according to the present invention.

Toxicity and therapeutic efficacy of the compositions described herein can be determined by standard pharmaceutical procedures in cell cultures or experimental animals, e.g., by determining the IC50 (the concentration which provides 50% inhibition) and the maximal tolerated dose for a subject compound. The data obtained from these cell culture assays, and animal studies can be used in formulating a range of dosages for use in humans. The dosage may vary depending inter alia upon the dosage form employed, the dosing regimen chosen, the composition of the agents used for the treatment and the route of administration utilized, among other relevant factors. The exact formulation, route of administration and dosage can be chosen by the individual physician in view of the patient's condition. Depending on the severity and responsiveness of the condition to be treated, dosing can also be a single administration of a slow-release composition, with course of treatment lasting from several days to several weeks or until cure is affected or diminution of the disease state is achieved. The amount of a composition to be administered will, of course, be dependent on the subject being treated, the severity of the affliction, the manner of administration, the judgment of the prescribing physician, and all other relevant factors.

The term "administering" or "administration of" a substance, a compound or an agent to a subject can be carried out using one of a variety of methods known to those skilled in the art. For example, a compound or an agent can be administered enterally or parenterally. Enterally refers to administration via the gastrointestinal tract including per os, sublingually or rectally. Parenteral administration includes administration intravenously, intradermally, intramuscularly, intraperitoneally, subcutaneously, ocularly, sublingually, intranasally, by inhalation, intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Antibodies are generally administered in the range of about 0.1 to about 20 mg/kg of patient weight, commonly about 0.5 to about 10 mg/kg, and often about 1 to about 5 mg/kg. In this regard, it is preferred to use antibodies having a circulating half-life of at least 12 hours, preferably at least 4 days, more preferably up to 21 days. Chimeric antibodies are expected to have circulatory half-lives of up to 14-21 days. In some cases, it may be advantageous to administer a large loading dose followed by periodic (e.g., weekly) maintenance doses over the treatment period. Antibodies can also be delivered by slow-release delivery systems, pumps, and other known delivery systems for continuous infusion.

The term "about" means that an acceptable error range, e.g., up to 5% or 10%, for the particular value should be assumed.

The present invention further comprises, according to another aspect, a method of determining or quantifying CD112R in a sample, the method comprising contacting a biological sample with an antibody or antibody fragment according to the invention, and measuring the level of complex formation The present invention further discloses methods for diagnosing and prognosing cancer.

According to an aspect, the present invention provides a diagnostic and/or prognostic method of cancer or infectious disease in a subject, the method comprises the step of determining the expression level of CD112R in a biological sample of said subject using at least one antibody as described herein.

The term "biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived there from and the progeny thereof. Additionally, the term may encompass circulating tumor or other cells. The term specifically encompasses a clinical sample, and further includes cells in cell culture, cell supernatants, cell lysates, serum, plasma, urine, amniotic fluid, biological fluids including aqueous humour and vitreous for eyes samples, and tissue samples. The term also encompasses samples that have been manipulated in any way after procurement, such as treatment with reagents, solubilization, or enrichment for certain components.

Determining the expression level of CD112R can be performed by a labeled anti-CD112R antibody as described herein. Determining the expression can be performed, for example, by ELISA.

The method of the invention can further comprise the step of comparing said level of expression to a control level.

The following examples are presented in order to more fully illustrate some embodiments of the invention. They should, in no way be construed as limiting the scope of the invention.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological, immunological and recombinant DNA techniques. Such techniques are well known in the art. Other general references referring to well-known procedures are provided throughout this document for the convenience of the reader.

Example 1. Expression of CD112R is Increased after Immune Cells Activation

Figure 1B:
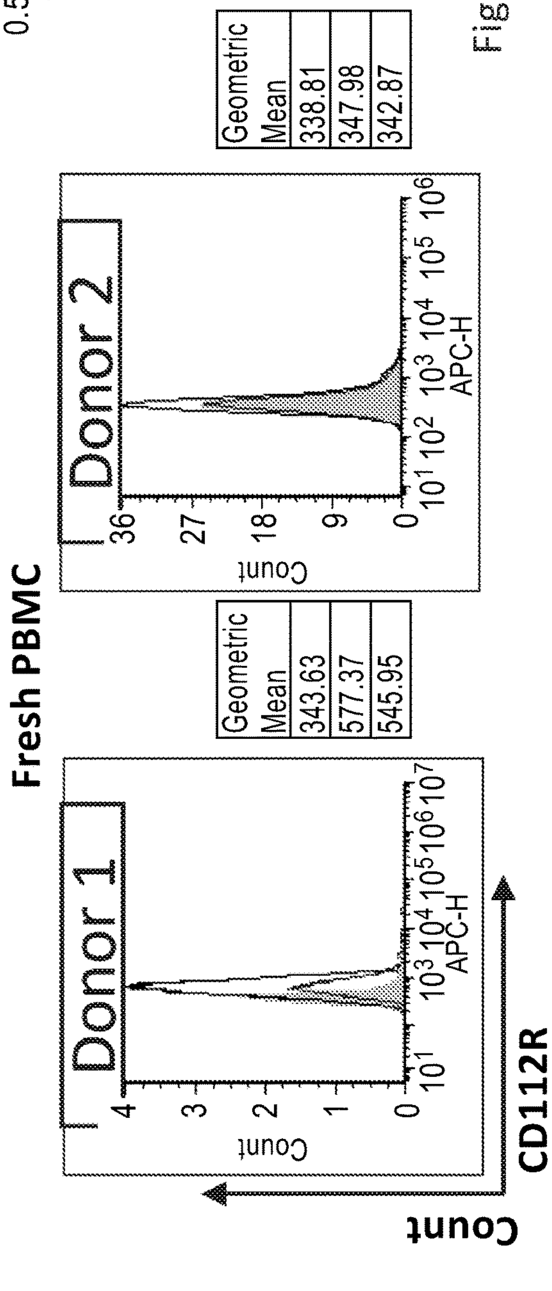
FIGS. 1B-1D show FACS analysis of staining of various immune cells by anti-CD112R mAbs of the present invention (hybridoma supernatants).
Figure 1C:
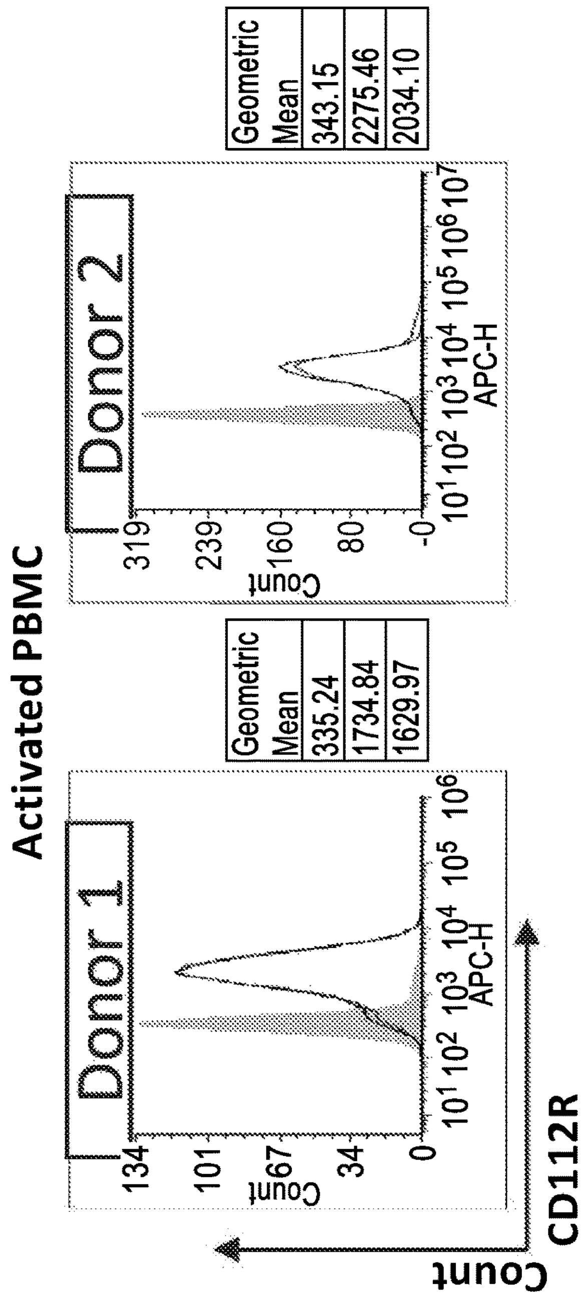
Figure 1D:
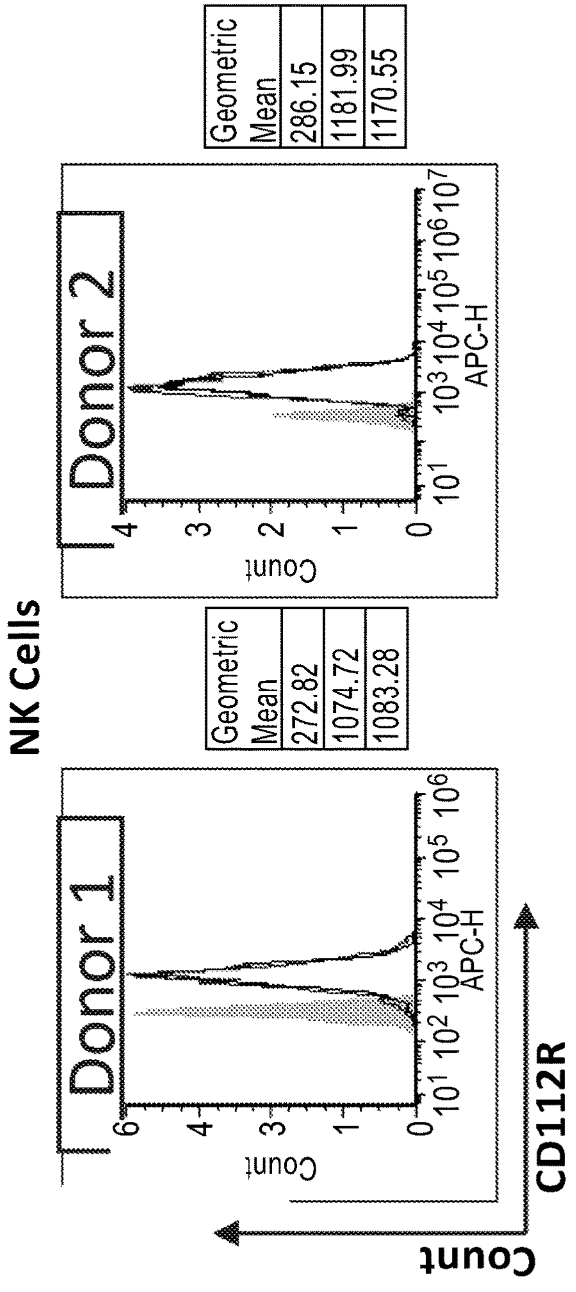

CD112R mRNA expression in human immune cells as found at the Database of Immune Cell Expression (DICE, dice-database.org/) is depicted in FIG. 1A. It is shown that CD112R is expressed mainly on NK cells, B cells and T cells. For CD112R detection on human immune cells (FIGS. 1B-1D), 50K cells were stained using 30 l/well of supernatants from hybridoma of clone 13 and 15. For detection, Goat anti-mouse-647 Ab (Jackson immunoresearch cat. 315-605-006) was used at 1:250 dilution. Peripheral blood mononuclear cells (PBMCs) from two healthy donors were used. While no detectable staining was depicted on the surface of resting PBMCs (FIG. 1B), After 96 hours in NK medium (400 u/ml hIL-2) with 2 μg/ml PHA-L activation, significant and uniform expression of CD112R was observed (FIG. 1C). Both NK cell population's tested expressed CD112R, regardless of the activation status (FIG. 1D).

Figure 2:
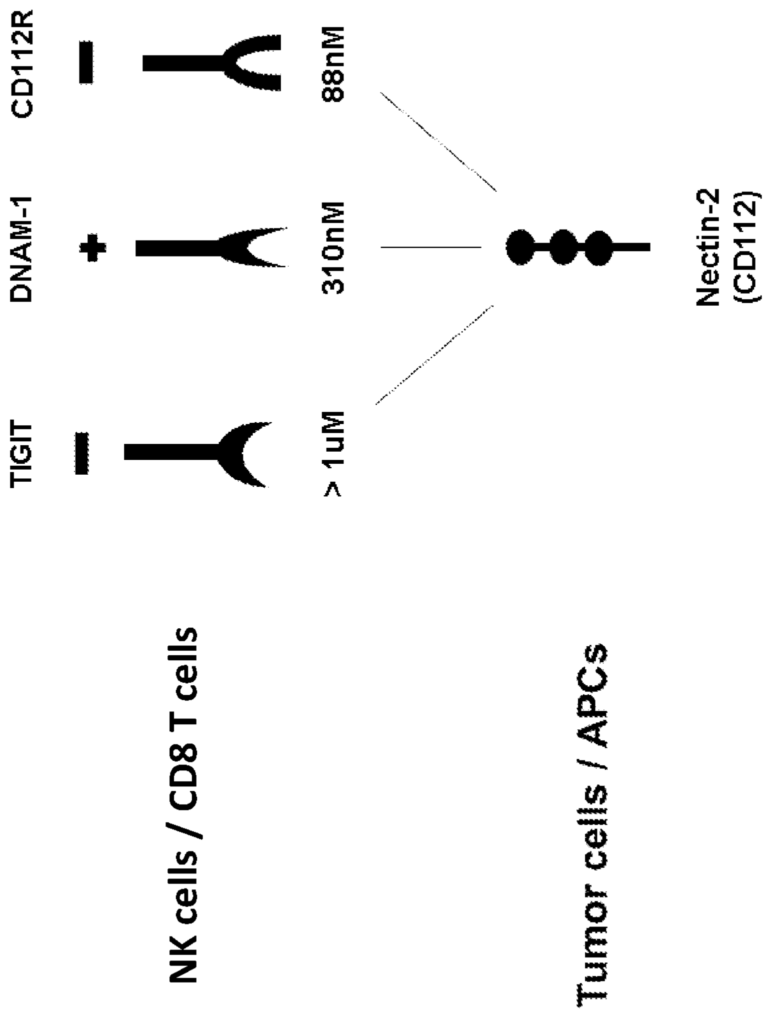
FIG. 2 is a schematic illustration of receptors expressed on NK/CD8 T cells (TIGIT, DNAM-1, CD112R) and their respective affinities to Nectin-2 expressed by tumors or by antigen presenting cells (APCs).

Example 2. CD112R is an Inhibitory Receptor Predominantly Engaged by Nectin-2 Binding A schematic illustration of receptors expressed on immune cells and their respective affinities to Nectin-2 (CD112), an inhibitory ligand for immune cells, which is expressed by tumors or on antigen presenting cells (APCs), is shown in FIG. 2. TIGIT is a co-inhibitory receptor on immune cells such as T and NK cells; DNAM-1 (also termed CD226) is an activating receptor on immune cells (e.g., T cells), and CD112R (also termed PVRIG) is a co-inhibitory receptor on cytotoxic immune cells (e.g., CD8+T and NK cells); According to some embodiments of the present invention, anti-CD112R mAbs block CD112R interactions with its ligand Nectin-2 and increase activation of immune cells, without interfering with DNAM-1 signaling.

Example 3. Analysis of Binding and Blocking Characteristics of the Anti-CD112R mAbs FIG. 3A illustrates specific binding of anti-CD112R clones to 293T cells (highly transfectable derivative of human embryonic kidney 293 cells) engineered to overexpress CD112R. CD112R mAbs were used in a saturating dose (66 nM) on either parental or on CD112R overexpressing 293T cells. Only the overexpressing cells showed a positive staining signal (with no significant difference between the clones tested), pointing to the high specificity of the mAbs to CD112R. EC-50 values are summarized in FIG. 3B. CD112R chimeric mAbs comprising human IgG1 with or without N31S substitution were used in concentration of 0.4-99 nM in series of three-fold dilutions and incubated with 293T cells that overexpress CD112R. For detection, goat anti-human labeled with allophycocyanin (APC) (Jackson immunoresearch 109-136-170) Ab was used at 1:200 dilution. Binding was analyzed by FACS and used for calculation of EC-50 values. These results suggest that all tested mAbs bind cell surface expressed CD112R at sub-nM or at nM affinities. The N31S variant, engineered to remove an N-Linked glycosylation motif at the CDR1 of the heavy chain, had improved (sub-nM) binding to human CD112R in this cell-based assay. In addition, 8866 cells (chronic myelogenous leukemia cells) overexpressing human Nectin-2 were incubated with 10 μg/ml (156 nM) of CD112R-Fc in the presence of isotype control or with the indicated mAbs at 4 μg/ml (26.4 nM, meaning 6-fold excess of the CD112R-Fc). As can be seen in FIG. 3C, the blocking of CD112R-Fc binding exceeded 95% by all tested variants.

Figure 4C:
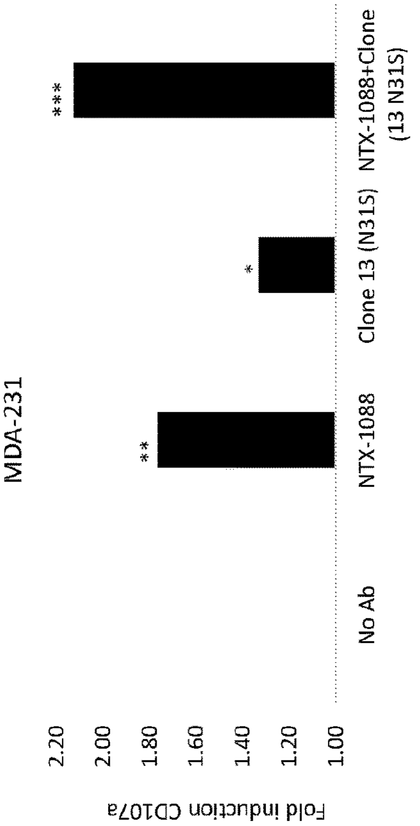
FIGS. 4A-4C illustrate blocking of CD112R by the anti-CD112R mAbs and its effect on NK cell activation. NK activation was measured by the induction of surface expression of CD107a, which is expressed as fold change over control IgG (Y axis). Results are shown for the human cancer cell lines A549 (lung adenocarcinoma.
Figure 4A:
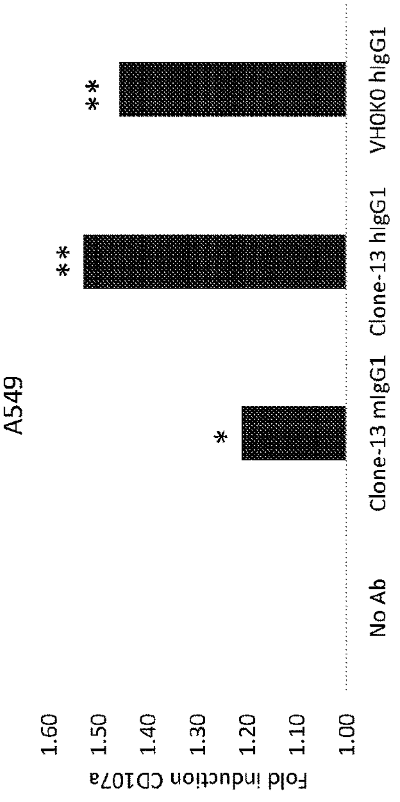
Figure 4B:
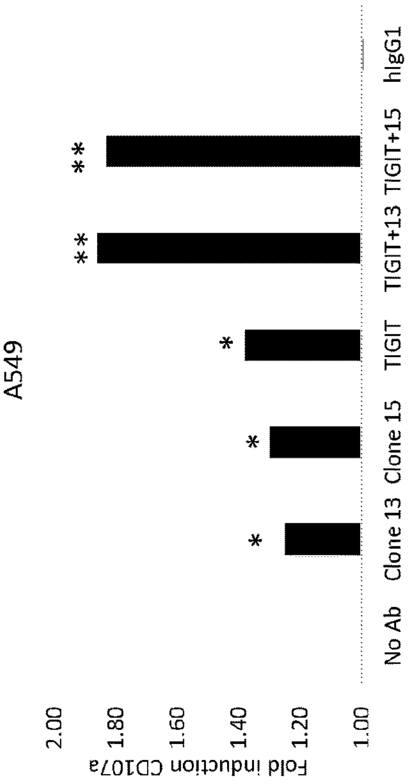

Example 4. Blocking of CD112R by the hIgG1 Anti-CD112R mAbs Enhances NK Cell Activation NK cells from healthy donors were incubated in the presence of different mAbs and target cell lines at 2:1 E:T ratio for 2 hours at 37° C. degrees. NK cell activation was measured by the induction of surface expression of CD107a, and is depicted in FIG. 4 as fold change over control IgG (Y axis). To assess whether Fc type affects the function of the CD112R mAbs, the activity of an anti-CD112R mAb (clone 13) comprising mouse IgG1 (inert Fc with no detectable binding to hCD16) was compared to two other anti-CD112R mAbs: the chimeric Clone-13-hIgG1, and chimeric clone-13(N31S)-hIgG1 (VH0K0) both having hIgG1 Fc (effector Fc capable of activating hCD16). All Ab variants were tested at 2 nM (0.3 μg/ml). As seen in FIG. 4A, both hIgG-Fc mAbs exhibited significant superiority over the inert Fc Ab. Thus, further development was done using anti-CD112R mAbs with human IgG1. For assessment of additive and synergistic effects, CD112R blockade was combined with additional ICIs and results are shown in FIGS. 4B and 4C. Blockade of CD112R by the two mAb clones tested induced NK activation (CD107a cell surface expression), and also synergized with other immune checkpoint blockade, including blocking of TIGIT and PVR (NTX-1088). All were statistically significant ($p<0.05$) over control IgG. This data suggests that blocking of CD112R by specific mAbs may increase NK cell activity against cancer targets and may have a synergistic effect on NK activations when combined with other immune checkpoint inhibitor (ICI) mAbs. All mAbs were used at 3 μg/ml (3+3 μg/ml for the combos). Results are shown for the human cancer cell lines A549 (FIG. 4A, 4B lung adenocarcinoma) and MDA-MB-231 (FIG. 4C, breast adenocarcinoma).

Figure 5B:
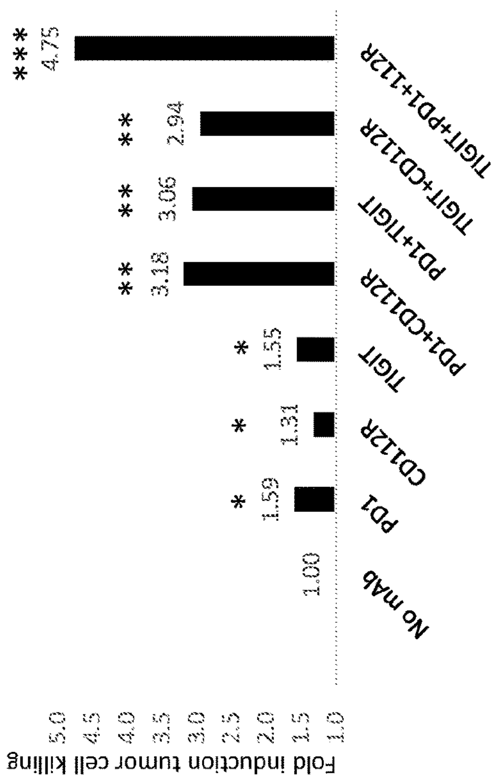
FIGS. 5A-5B illustrate effect of blocking of CD112R by the anti-CD112R mAbs (Clone 13 N31S) on T cell-mediated target cell killing. The effect of blocking of CD112R was further examined in the presence of additional ICIs, such as TIGIT and PD-1. Target cell killing was normalized to that observed when no Ab was added (Y axis). Results are shown for the human cancer cell lines A549 (lung adenocarcinoma, FIG. 5A) and RKO (colorectal cancer, FIG. 5B). * $p<0.05$,  $p<0.01$, * $p<0.0005$ by two tailed student t-test.
Figure 5A:
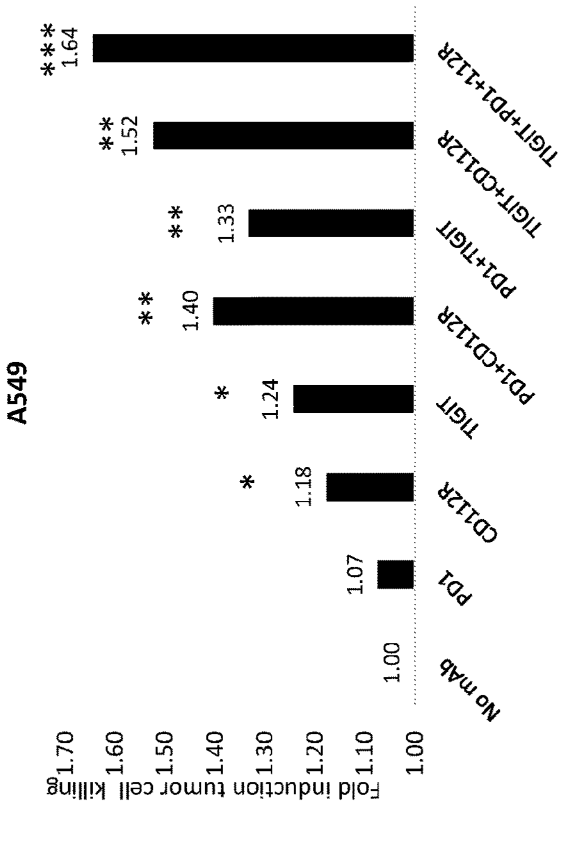

Example 5. Blocking of CD112R by the Anti-CD112R mAbs Enhances T Cell Mediated Tumor Cell Killing PBMCs from healthy donors were used for T cell killing assay using human cancer cell lines A549 (lung adenocarcinoma, FIG. 5A) and RKO (colorectal cancer, FIG. 5B). All mAbs were used at 3 μg/ml (3+3 μg/ml were used for the combos, and 3+3+3 μg/ml for the triple). The anti-CD112R clone 13 was used in the assay. Target cell killing was normalized to effector cells only (Y axis). The target cell killing was evaluated by the CellTiter-Glo® 2.0 Cell Viability Assay kit by Promega (Cat G9242) according to the manufacturer protocol. Results show that CD112R mAbs lead to significant target cells killing, synergies with anti-TIGIT and anti-PD-1 mAbs. Moreover, blocking all three receptors significantly increased target cells killing over the effect of the individual mAbs and of double mAb combination.

Example 6. Humanization of CD112R Antibodies Improved Binding and Developability Properties of the mAbs The heavy chain variable region sequence of anti-CD112R clone 13, contained several limitations, which were addressed during the humanization process.

A deamidation motif in the CDR1 of the light chain was addressed by replacing Asn (N) by Ser (S) (named N31S).

Both the Clone-13-hIgG1 and the N31S (deamidation site abrogated) chimeric variants (hIgG1) exhibited exceptional high affinity and were significantly more potent (3-30 folds) in binding CD112R (PVRIG), than a reference (control) Ab that binds to the same antigen (an Ab disclosed in WO2016134333), (Table 1).

TABLE 1 affinities of the chimeric clone (clone 13) and clone N31S (in which the deamidation motif at amino acid No. 31 was deleted), and a reference Ab that is based on a sequence from WO2016134333 for binding of human CD112R (PVRIG).

| Ligand | Analyte | $K_a$ (1/Ms) | $K_d$ (1/s) | $K_D$(M) |
|---|---|---|---|---|
| Human | Clone 13 | 3.4E+05 | 2.96E−06 | 8.71-12* |
| CD112R | Clone 13 (N31S) | 3.4E+05 | 3.26E−07 | 9.6-13* |
| (PVRIG) | control | 8.95E+04 | 2.19E−06 | 2.44-11* |

*Limit of Biacore instrument

Next, variants were made to remove an N-linked glycosylation motif found at the CDR1 of the heavy chain (Chothia CDR definition). The variants contained substitution of the amino acid residue Asparagine (N) at position 28 with a residue selected from Aspartic acid (D), Alanine (A), Glutamine (Q), Serine (S), and Threonine (T), and substitution of the amino acid residue Threonine (T) at position 30 by Alanine (A). All variants were tested for productivity (based on titer concentrations) and affinity as summarized in Table 2.

TABLE 2 productivity and affinity of the variants in which N-Linked glycosylation motif was removed

| Antibody | Variant | Titer (ug/ml) | Kd (M) | Relative Kd |
|---|---|---|---|---|
| VH0Vk0 | WT | 47.6 | 1.67E−10 | 1.00 |
| VH0 N28D Vk0 | N28D | 4.7 | 1.22E−10 | 0.73 |
| VH0 N28A Vk0 | N28A | 3.9 | 1.5E−10 | 0.9 |
| VH0 N28Q Vk0 | VH0 N28Q Vk0 | 3.0 | 1.16E−10 | 0.69 |
| VH0 N28S Vk0 | N28S | 4.0 | 1.16E−10 | 0.66 |
| VH0 N28T Vk0 | VH0 N28T Vk0 | 3.2 | 1.02E−10 | 0.61 |
| VH0 T30A Vk0 | T30A | 6.0 | 1.06E−10 | 0.63 |

Based on the relative affinity results, the variant N28T was selected. Removal of the N-linked glycosylation did not affect affinity, but significantly reduced productivity. To address this, 11 variants of humanized heavy chains, deleting the N-linked glycosylation motif, were designed as scFv molecules, on human IgG1 Fc, and tested for productivity (Table 3). The top three productive humanized scFv variants (#9-11) were tested for binding to the human CD112R (Table 4). Majority of the humanized scFv variants had significantly improved binding compared to the scFv of VH0K0 (Clone 13 N31S).

TABLE 3 shows productivity in 293EBNA cells of ten humanized variants that were designed based on N28T mutation, and that are co-expressed with the unmodified light chain as scFv. The scFv molecules were connected to an Fc as a technical solution for a rapid production and screening of the variants.

| ScFv-Fc | HEK Titer (μg/ml) |
|---|---|
| Variant 0 | 0.559 |
| Variant 1 | <0.4 |
| Variant 2 | 0.5353 |
| Variant 3 | <0.4 |
| Variant 4 | Not received |
| Variant 5 | <0.4 |
| Variant 6 | 0.524 |
| Variant 7 | <0.4 |
| Variant 8 | <0.4 |
| Variant 9 | 6.61 |
| Variant 10 | 1.26 |
| Variant 11 | 8.23 |

TABLE 4 binding affinities to human CD112R of heavy chain variants (#9-11) and the non-humanized version (VH0), co-expressed with the non-modified light chain (VK0) and with three humanized variants of the light chain as indicated

| Antibody | $K_a$ (1/Ms) | $K_d$ (1/s) | $K_d$ (M) | Relative $K_d$ |
|---|---|---|---|---|
| VH0K0 | 2.90E+5 | 8.89E−5 | 3.07E−10 | 1.00 |
| VH10K2 | 6.23E+5 | 1.33E−4 | 2.14E−10 | 0.7 |
| VH10K3 | 5.45E+5 | 1.07E−4 | 1.97E−10 | 0.64 |
| VH11K1 | 6.3E+5 | 1.01E−4 | 1.65E−10 | 0.54 |
| VH11K2 | 5.52E+5 | 1.05E−4 | 1.91E−10 | 0.62 |
| VH11K3 | 5.30E+5 | 1.01E−4 | 1.90E−10 | 0.62 |

Based on proximity to human germline Abs and lack of potential MHC-2 binding motifs (predicted by iTope™), five variants were selected for further analysis. The affinity of selected variants is shown in Table 5. All variants had improved binding to human CD112R compared to the chimeric (clone N31S) Ab.

TABLE 5 properties of selected full antibody variants after purification

| Antibody | $K_a$ (1/Ms) | $K_d$ (1/s) | $K_d$ (M) | Relative $K_d$ |
|---|---|---|---|---|
| VH0K0 | 2.10E+05 | 3.05E−05 | 1.45E−10 | 1.16 |
| VH0K0 N28T | 4.00E+05 | 5.02E−05 | 1.26E−10 | 1 |
| VH0K1 N28T * | 3.20E+05 | 8.30E−06 | 2.59E−11 | 0.21 |
| VH0K2 N28T | 3.98E+05 | 4.34E−05 | 1.09E−10 | 0.87 |
| VH0K3 N28T * | 3.30E+05 | 1.06E−05 | 3.21E−11 | 0.25 |
| VH9K0 * | 3.00E+05 | 3.09E−06 | 1.03E−11 | 0.08 |
| VH9K1 | 3.50E+05 | 3.87E−05 | 1.11E−10 | 0.87 |
| VH9K2 * | 3.01E+05 | 1.30E−05 | 4.32E−11 | 0.34 |
| VH9K3 | 3.30E+05 | 1.06E−05 | 3.21E−11 | 1.22 |
| VH10K0 | 3.45E+05 | 4.66E−05 | 1.35E−10 | 1.07 |
| VH10K1 | 3.51E+05 | 4.18E−05 | 1.19E−10 | 0.94 |
| VH10K2 | 3.59E+05 | 4.27E−05 | 1.19E−10 | 0.94 |
| VH10K3 | 3.61E+05 | 4.36E−05 | 1.21E−10 | 0.96 |
| VH11K0 | 3.16E+05 | 3.19E−05 | 1.01E−10 | 0.8 |
| VH11K1 * | 2.87E+05 | 4.79E−06 | 1.67E−11 | 0.13 |
| VH11K2 | 3.36E+05 | 3.77E−05 | 1.12E−10 | 0.89 |
| VH11K3 * | 3.07E+05 | 2.42E−05 | 7.88E−11 | 0.63 |

* Limit of the Biacore instrument sensitivity

Example 7. Similar Binding of Anti-CD112R mAbs to CD112R of Human and Cynomolgus Monkey The humanized mAbs were tested for binding of endogenous and overexpressed human and cynomolgus CD112R.

The results show that the affinity of the humanized mAbs to the human and monkey CD112R is similar. Table 6 summarizes EC50 values calculated based on binding curves of selected humanized (Hu) mAbs, which were used at concentration of 99-0.05 nM in a series of three-fold dilutions to 293T cells expressing either human (protein id NP_076975.2) or cynomolgus (Cyno) monkey (*Macaca fascicularis*) CD112R (protein id: XP_005549281.1). For detection, donkey anti-human-647 (Jackson immunoresearch cat-109-605-006) Ab was used at 1:250 dilution.

Table 7 summarizes EC50 values calculated based on the binding curves of selected humanized mAbs to cynomolgus CD8 T cells and human NK cells, both cells expressing endogenous CD112R of the relevant species. Assay was performed as in Table 6. An anti-CD112R mAb disclosed in WO2016134333 was used for comparison. The relative EC-50 values are also summarized in Tables 6 and 7. Max binding was assessed as well (human max binding—background/cyno max binding—background) and is summarized in Table 8. All the humanized variants have a complete cross-reactivity between the human and cynomolgus targets. Additionally, the superior binding of all the humanized variants to the antigen, compared to a control Ab is seen, with three of the five humanized variants having over two-fold improved binding compared to the reference Ab and the remaining two variants display about 50% improvement.

TABLE 6 assessment of binding characteristics (EC50 and max binding) of selected humanized anti-CD112R mAbs to cell surface CD112R

| Clone name | H0K0 | H10K2 | H10K3 | H11K1 | H11K2 | H11K3 |
|---|---|---|---|---|---|---|
| EC50 nM HuCD112R | 0.55 | 0.40 | 0.30 | 0.30 | 0.28 | 0.31 |
| EC50 nM CynoCD112R | 0.97 | 0.42 | 0.50 | 0.72 | 0.71 | 0.60 |
| Ratio Cyno/Hu | 1.75 | 1.07 | 1.67 | 2.43 | 2.54 | 1.93 |

TABLE 7 assessment of binding of selected humanized anti-CD112R mAbs to cynomolgus CD8 T cells and to human NK cells which express endogenous CD112R of the relevant species.

| Clone name | H10K2 | H10K3 | H11K1 | H11K2 | H11K3 | Com |
|---|---|---|---|---|---|---|
| EC-50 nM Hu | 0.86 | 0.77 | 0.91 | 1.06 | 1.11 | 1.87 |
| EC-50 nM Cyno | 1.45 | 1.39 | 1.46 | 1.29 | 1.27 | 2.05 |
| Ratio Cyno/Hu | 1.69 | 1.81 | 1.61 | 1.22 | 1.14 | 1.09 |

TABLE 8 a summary of absolute and relative Max binding assessment. of selected humanized anti-CD112R mAbs to cynomolgus CD8 T cells and to human NK cells which express endogenous CD112R of the relevant species. Relative binding (ratio) was calculated as (human max binding − background)/(cyno max binding − background)

| Clone name | H10K2 | H10K3 | H11K1 | H11K2 | H11K3 | Com |
|---|---|---|---|---|---|---|
| Max binding Hu (MFI a.u − background) | 975 | 988 | 982 | 1018 | 1005 | 993 |
| Max binding Cyno (MFI a.u − background) | 914 | 933 | 820 | 839 | 833 | 1583 |
| Ratio Hu/Cyno | 1.07 | 1.06 | 1.20 | 1.21 | 1.21 | 0.63 |

Example 8. Humanized CD112R mAbs Effectively Block Binding of CD112R to CD112

The humanized anti-CD112R antibodies are potent blockers of CD112R—Nectin-2 interactions. 293T cells overexpressing CD112R, were incubated (75 k/well) with the fusion protein hNectin-2-mIgG2a at a set dose (125 nM) in the presence or absence of the humanized CD112R mAbs, on ice for 30 minutes. The antibodies were added in a range of concentrations of 40-0.018 nM in a series of three-fold dilutions. The amount of bound hNectin-2-mIgG2a was detected by anti-mouse antibodies fluorescently labeled with Dy-light 647 (115-606-071 Jackson immunoresearch) and analyzed by FACS. The EC-50 and EC-90 values were calculated from the resulting titration curves and are summarized in Table 9 below. The results show that the humanized CD112R antibodies are capable of blocking the CD112R-CD112 interactions at sub-nM concentrations.

TABLE 9 blocking of CD112R-Nectin-2 interactions by the humanized anti-CD112R antibodies

| Antibody Clone | H11K1 | H11K2 | H11K3 |
|---|---|---|---|
| EC-50 nM | 0.29 | 0.32 | 0.26 |
| EC-90 nM | 10.7 | 9.9 | 9.6 |

Figure 6:
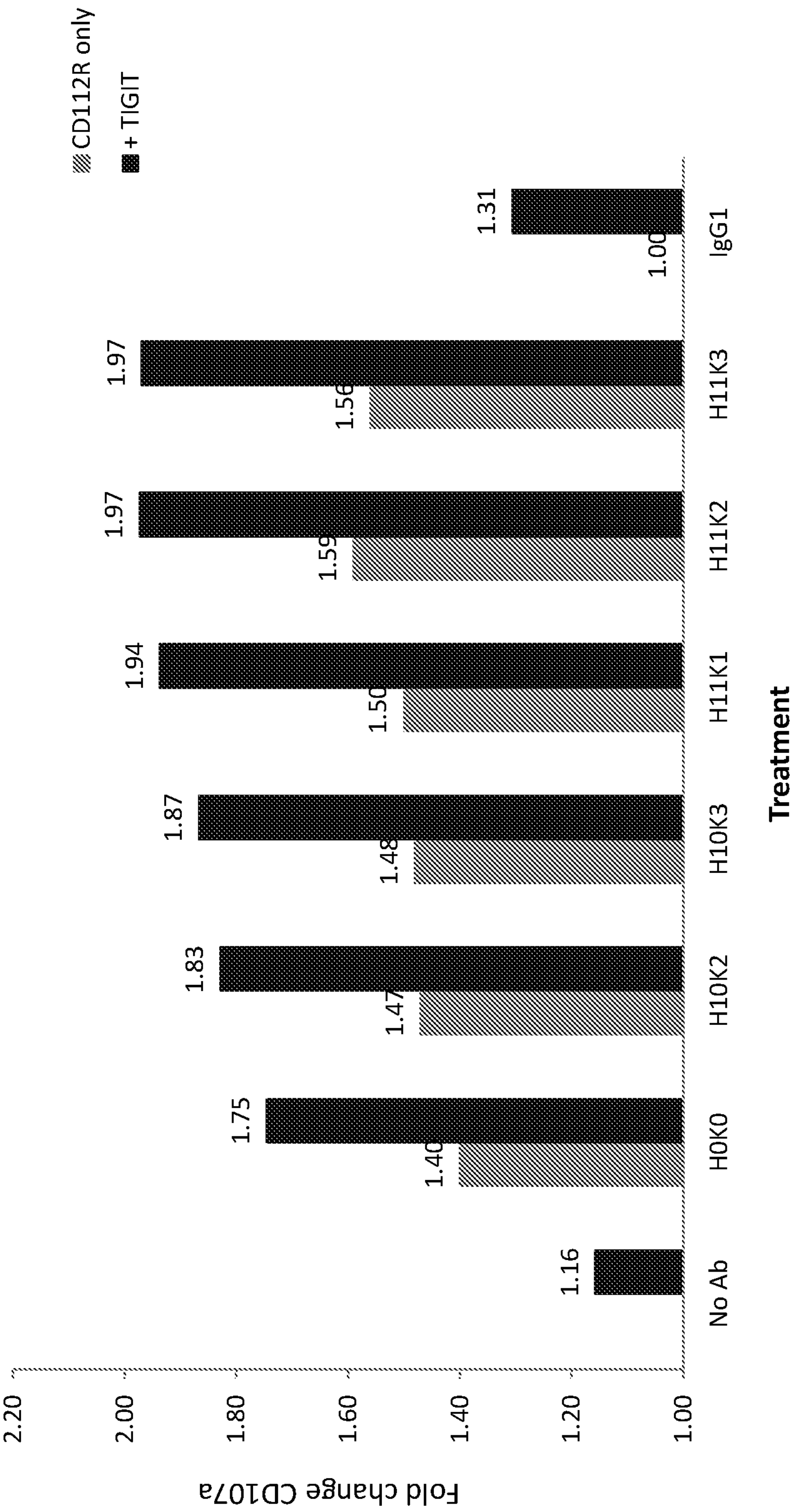
FIG. 6 shows activation effect of the humanized anti CD112R antibodies on NK cells. NK cell activation was assessed by the induction of surface expression of CD107a, as measured by FACS analysis, and was expressed as fold change over control IgG (Y axis). Results are shown for NK cells, isolated from a healthy human volunteer, that were co-incubated with the human cancer cell line A549 (lung adenocarcinoma). Incubation was done in the presence of various anti-CD112R humanized clones, or with an isotype IgG control, as depicted at the X axis, with or without additional anti-TIGIT mAbs. All Abs were added at 3 μg/ml.

Example 9. Blocking of CD112R by the Humanized Anti-CD112R mAbs Enhances NK Cell Activation Over the Parental mAb and Synergizes with Blocking of TIGIT To examine the blocking effect of the humanized anti-CD112R mAbs, NK cells from a healthy donor were incubated in presence of different mAbs with A549 cells (lung adenocarcinoma) at 2:1 E:T ratio for 2 hours at 37° C. NK cell activation was measured by the induction of surface expression of CD107a and is depicted in FIG. 6 as fold change over control IgG (Y axis). All mAbs were used at 3 μg/ml (3+3 for the combos). All the anti-CD112R mAbs (grey bars) significantly increased NK cell activation ($p<0.0005$). Moreover, the humanized anti-CD112R antibodies were superior to the parental, non-humanized (HOKO) chimeric variants ($p<0.05$). Additionally, all the humanized variants synergized with anti-TIGIT mAb (black bars), leading to significant increase of activity over each individual treatment ($p<0.015$).

Overall, the data suggest that humanized anti-CD112R mAbs are potent inducers of NK cell activation, superior to the parental anti-CD112R and maintain the synergistic effect when combined with anti-TIGIT mAb.

Figure 7A:
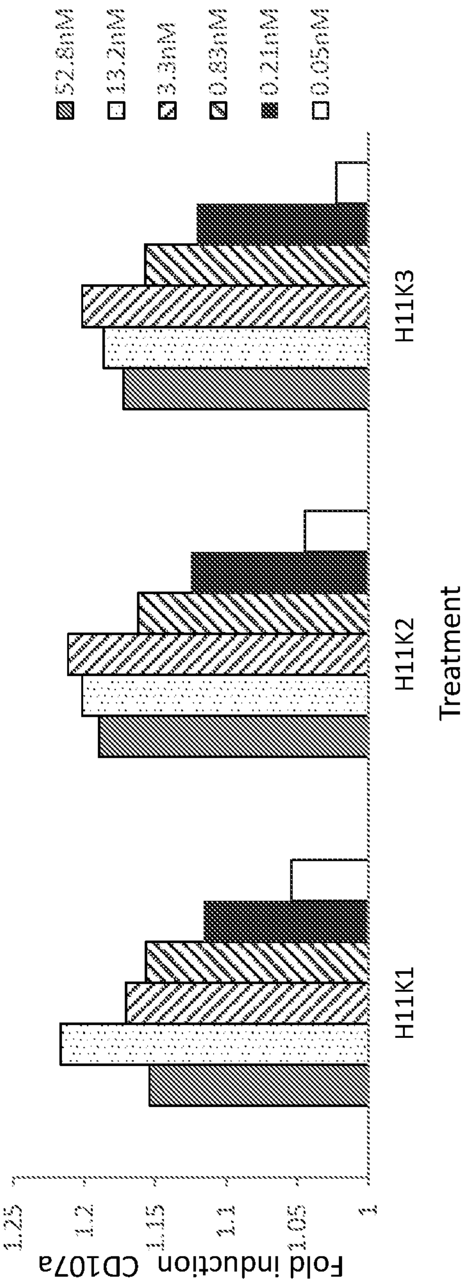
FIGS. 7A-7B show the effect of the selected humanized anti-CD112R, alone and in combination with anti-PVR, on NK cell activation. NK cell activation was measured by the induction of surface CD107a and was expressed as fold-change over no Ab (Y axis).
Figure 7B:
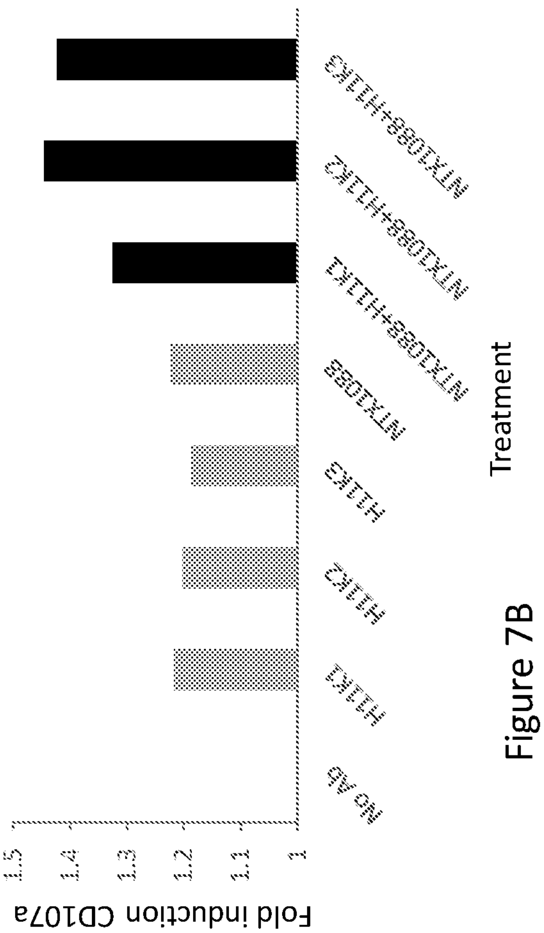

Example 10. Blocking of CD112R by Humanized Anti-CD112R mAbs Enhances NK Cell Activation in a Dose Dependent Manner and Synergizes with Blocking of PVR NK cells from a healthy donor were incubated in presence of different mAbs with MDA-MB-231 cells (breast adenocarcinoma) at 2:1 E:T ratio for 1.5 hours at 37° C. NK cell activation was measured by the induction of surface expression of CD107a as analyzed by FACS and is depicted as fold change over control IgG (Y axis). The humanized mAbs (H11K1, H11K2, and H11K3, having HC variable region sequence set forth in SEQ ID NO: 39, and LC variable region sequence set forth in SEQ ID NO: 40, SEQ ID NO: 41, SEQ ID NO: 42, respectively) were used at a range of concentrations from 53-0.05 nM in 4-fold dilutions (FIG. 7A). Additionally (FIG. 7B), a set dose of 13 nM of each mAb was tested in combination with 13 nM of anti-PVR Ab (NTX-1088). FIG. 7A shows that the lead humanized anti-CD112R mAbs are potent inducers of NK activation. All the anti-CD112R mAbs tested significantly ($p<0.0172$) increased NK cells activation, up to a concentration of 0.05 nM, which is roughly 10-folds below EC-50. All the leading humanized variants (grey bars) synergized with the anti-PVR NTX-1088 Ab (black bars), leading to significant ($p<0.03$) increase of activity over each individual treatment. Overall, the data suggest that humanized anti-CD112R mAbs are potent activators of NK cells and that the selected variants synergize with anti-PVR mAb in NK cells activation.

Figure 8A:
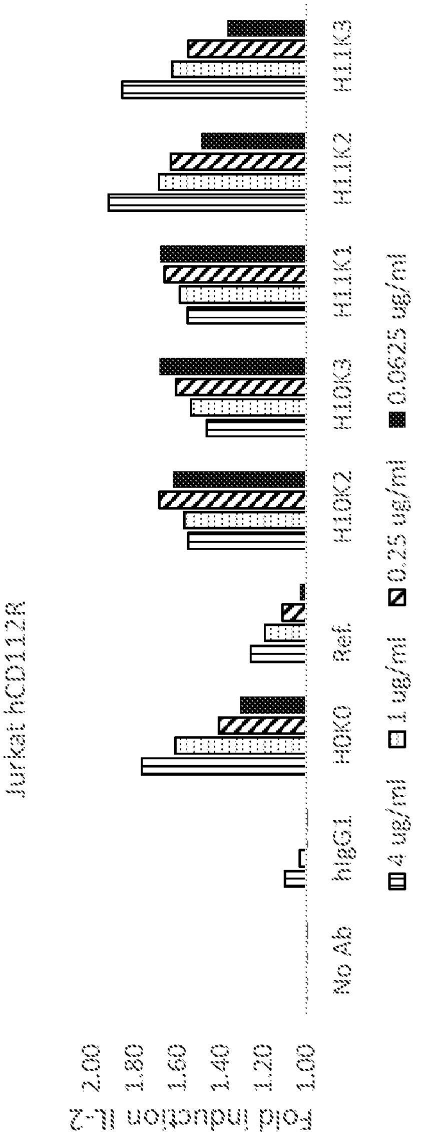
FIGS. 8A-8B illustrate the effect of the selected humanized anti-CD112R antibodies on activation of T cells (IL-2 secretion). Jurkat cells overexpressing the human CD112R were incubated with A549 cells in the presence of anti-CD3, with or without the indicated anti-CD112R mAbs. After 24 hours the supernatants were collected, and IL-2 content was quantify using Human IL-2 ELISA MAX™ Deluxe by Biolegend.
Figure 8B:
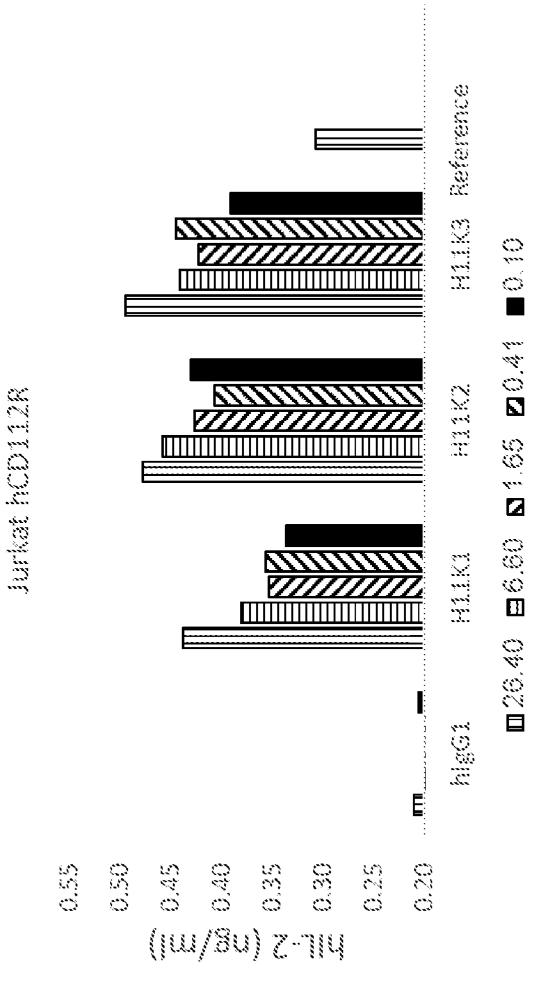

Example 11. Humanized Anti-CD112R mAbs are Superior to the Non-Humanized Ones and to a Reference CD112R mAb in Activation of T Cells To test the effect of the humanized anti-hCD112R antibodies on activation of T cells, Jurkat cells overexpressing the human CD112R (Jurkat hCD112R) were incubated with A549 cells (high Nectin-2 expression) in the presence of anti-CD3, with or without the indicated anti-CD112R mAbs. After 24 hours plates were centrifuged, and supernatants were collected. IL-2 quantification was done using Human IL-2 ELISA (MAX™ Deluxe by Biolegend), according to the manufacturer's protocol. FIG. 8A shows dose response assay of all the humanized variants and a reference anti-CD112R antibody (disclosed in WO2016134333), at concentration range of 4-0.0625 μg/ml. Most humanized clones were superior to the parental, non-humanized clone (HOKO), and all the anti-CD112R variants were superior to a reference Ab at all concentrations tested in inducing IL-2 secretion. FIG. 8B illustrates selected humanized variants tested as in FIG. 7A, in a range of concentrations from 26.4-0.1 nM. The reference Ab was only added at the highest concentration of 24.6 nM. All selected variants led to significant induction ($p<0.0003$) of IL-2 secretion. Comparison was done to the highest concentration of hIgG1. Moreover, antibodies H11K2 and H11K3 were significantly ($p<0.004$) more potent than the reference even at the lowest concentration tested, H11K1 was significantly superior to the reference starting from 0.41 nM ($p<0.02$).

These results indicate that the anti-CD112R mAbs are potent inducers of T cell activation, with significant advantage over the existing reference.

Example 12. Blocking of CD112R by the Anti-CD112R mAbs Enhances T Cell Activation PBMCs from healthy donors were used for T cell activation assay using human cancer cell line A549 (lung adenocarcinoma). The PBMCs were incubated for 48 hours with the target cells at 2:1 E:T ratio in the presence of 1 μg/ml of anti CD3 mAb (OKT3).

Figure 9B:
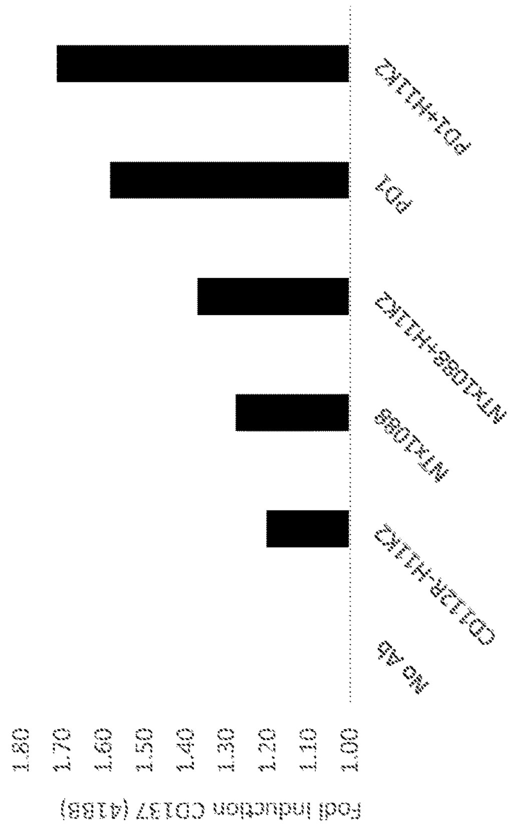
FIGS. 9A-9B illustrate the effect of the humanized anti-CD112R mAb variant H11K2 (having HC variable region sequence set forth in SEQ ID NO:39, and LC variable region sequence set forth in SEQ ID NO: 41) on T cell activation. The blockade of CD112R effect was measured with blocking of additional ICIs, such as PVR (NTX-1088) and PD-1 (Keytruda), as indicated. Surface expression (MFI) of CD69 (FIG. 9A) or CD137 (4-1BB) (FIG. 9B) was normalized to that observed when no Ab was added (Y axis). Results are shown for the human cancer cell line A549 (lung adenocarcinoma). All changes are statistically significant ($p<0.05$).
Figure 9A:
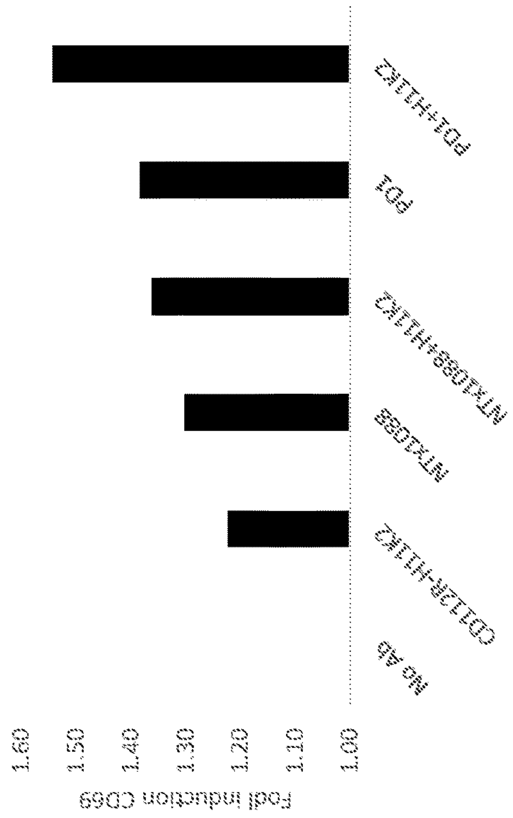

The effector cells were harvested and stained for the surface expression of (FIG. 9A) CD69 (BLG-310906) and (FIG. 9B) CD137 (BLG-309804, both from Biolegend). The surface expression (MFI) of the markers was normalized to the No mAb group.

As shown in FIG. 9. blocking of CD112R by the humanized anti-CD112R mAb H11K2 enhanced T cell activation. The blockade of CD112R had additive effect with blocking of additional ICIs, such as PVR (NTX-1088) and PD-1 (Keytruda). All changes are statistically significant ($p<0.05$).

Figure 10B:
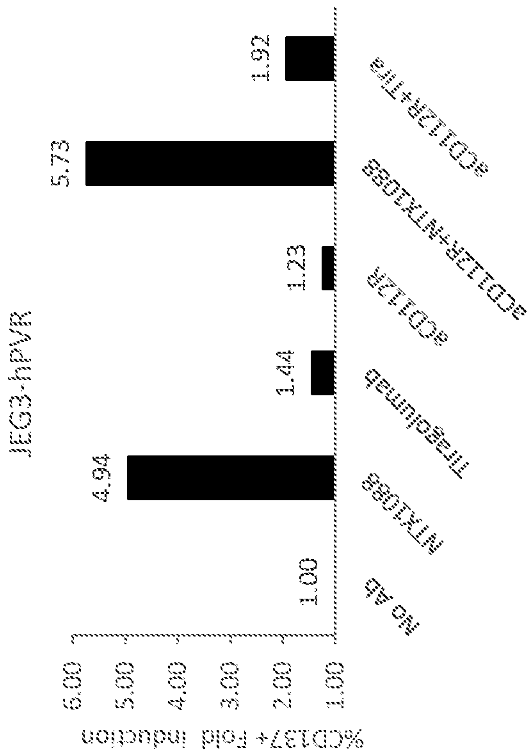
FIGS. 10A-10B show effect of CD112R blockade on NK cell activation when target cells express Nectin-2, but not PVR, and the effect of combining anti-CD112R with anti-PVR (NTX-1088) on NK activation, when target cells co-express Nectin-2 and PVR. NK cell activation was measured by surface expression of CD137, which is expressed as fold induction over no antibody treatment (no Ab. Y axis). Results are shown for the human cancer cell lines JEG-3 (choriocarcinoma) (FIG. 10A), which is PVR negative, and JEG-3-hPVR (FIG. 10B), which express human PVR. The anti-CD112R Ab with hIgG1 Fc was compared to the anti-PVR Ab NTX-1088, or to the anti-TIGIT Ab-Tiragolumab (KEGG DRUG entry D11482). Additionally, combinations of CD112R and the two mAbs were tested. * $p<0.005$,  $p<0.001$, * $p<0.0001$ by two tailed student t-test. Representative data of two out of five NK cell donors is shown. Tira=Tiragolumab.
Figure 10A:
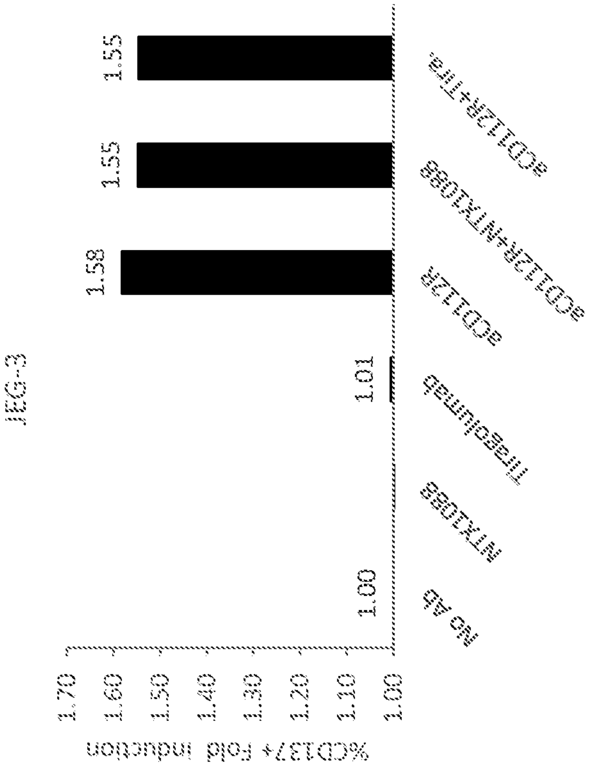

Example 13. Effect of Anti-CD112R on NK Cell Activation in the Presence of Target Cells Expressing Nectin-2, Lacking PVR, and the Impact of PVR Expression the Activity NK cells from healthy donors were incubated in the presence of different mAbs and target cell lines at 1:1 E:T ratio for 20 hours at 37° C. NK cell activation was measured by the induction of surface expression of CD137, and is depicted in FIG. 10 as fold induction over no antibody (Y axis). The humanized anti-CD112R mAb (H11K3 comprising hIgG1 Fc) was compared to NTX-1088 (anti-PVR) or to the anti-TIGIT mAb Tiragolumab (KEGG DRUG entry D11482) as standalone and in combinations. CD112R blockade by the lead humanized variant, was the most potent of all treatments when the target cells did not express membranal PVR (FIG. 10A). When PVR was expressed, CD112R synergized with other immune check point blockade, including blocking of TIGIT and blocking of PVR. The combination of NTX-1088 and anti-CD112R was significantly superior to all other interventions. All mAbs were used at 3 μg/ml (3+3 μg/ml for the combos). Results are shown for the human cancer cell lines JEG3 choriocarcinoma, lacking endogenous PVR (FIG. 10A), and JEG3-hPVR (human PVR overexpression, FIG. 10B). * $p<0.005$,  $p<0.001$, * $p<0.0001$ by two tailed student t-test. Representative data of two out of five donors is shown.

Figure 11C:
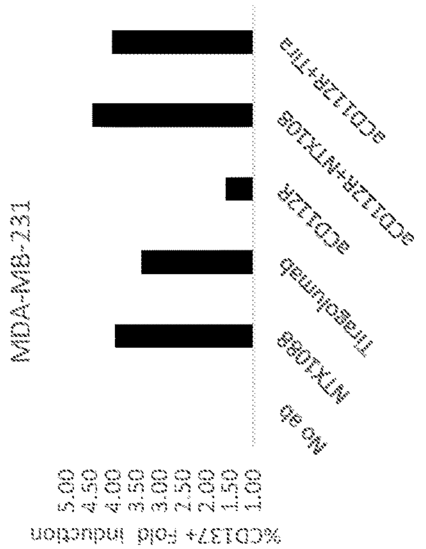
FIGS. 11A-11C demonstrate the effect of a combination of CD112R and other ICI blockade on NK cell activation when target cells express both Nectin-2 and PVR. Results are shown for the human non-small cell lung cancer cell line H1299 (FIG. 11A), the lung adenocarcinoma A549 cell line (FIG. 11B), and for the breast adenocarcinoma cell line MDA-MB-231 (FIG. 11C). The anti-CD112R mAbs activity was evaluated as a standalone or in combination with other ICI antibodies, as indicated. * $p<0.005$,  $p<0.001$, * $p<0.0001$ by two tailed student t-test. Representative data of two out of four NK cell donors is shown. Tira=Tiragolumab.
Figure 11B:
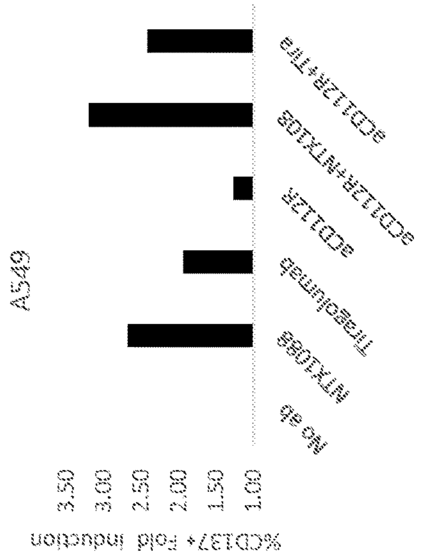
Figure 11A:
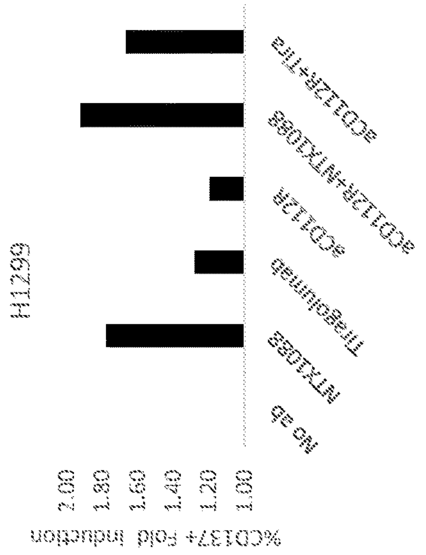

Example 14. Effect of Anti-CD112R on NK Cell Activation in the Presence of Cancer Target Cells NK cells from healthy donors were incubated in the presence of different mAbs and the target cell lines: H1299 (NSCLC, FIG. 11A), A549 (lung adenocarcinoma, FIG. 11B), or MDA-MB-231 (triple negative breast cancer, FIG. 11C) at 1:1 E:T ratio for 48 hours at 37° C. NK cell activation was measured by the induction of surface expression of CD137, and is depicted in FIG. 11 as fold induction over no antibody (Y axis). The humanized anti-CD112R mAb with hIgG1 Fc (H11K3) was evaluated as a standalone, or in combinations as in Example 1. In all settings, CD112R blockade as a standalone, had significant impact on activation of NK cells. Additionally, CD112R synergized with other immune check point blockades, including blocking of TIGIT (by Tirgaolumab KEGG DRUG entry D11482) and blocking of PVR (NTX-1088). Of note, the combination of NTX-1088 and anti-CD112R mAb was significantly superior to all other interventions, across all cell line tested. All mAbs were used at 3 μg/ml (3+3 μg/ml for the combos). * $p<0.005$,  $p<0.001$, * $p<0.0001$ by two tailed student t-test. Representative data of two out of four NK donors is shown.

Example 15. CD112R mAbs Inhibit Tumor Growth In Vivo

The efficacy of the mAbs is demonstrated in vivo using animal models. Immune compromised mice (NSG, NOG or equivalent) are used as a model. Target cell lines that naturally express Nectin-2 (e.g., A549, MDA-MB-231, RKO) are injected subcutaneously (sc) into mice, in amounts sufficient to allow robust tumor growth (e.g., $5*10^6$ cells per mouse). To provide immune cells, the tumor cells are mixed and injected with relevant human immune cells (e.g., whole PBMC, purified T cells, purified CD8+ T cells or NK cells).

The mice are then monitored for tumor growth until palpable tumors are formed. At this point, mice are randomized for different treatment groups that receive either control IgG, anti-CD112R mAbs, anti PD-1 mAb, or their combination. The effect of the individual and combined ICI treatments on tumor growth inhibition is evaluated over time against the control IgG group.

Additional approach is based on reconstitution of the immune cells after tumors are established. Here, same mice and tumor cells are used as above. However, the above mentioned human immune cells are injected intravenously (iv) and only after pulpable tumors are established. A day later mice are randomized to different treatment groups and tumor growth inhibition is evaluated as above.

A third strategy is taken where human hematopoietic stem cells, rather than mature leukocytes, are used to reconstitute the missing immune cells at the immune-deficient mice. Once the hematopoietic cells give rise to mature human immune cells at the periphery the resulting "humanized" mice, are used for tumor implantation and testing of the effects of the different ICI mAbs as described above for the iv-reconstitution approach.

Example 16. Effect of Anti-CD112R on Tumor Growth in Mice

Figure 12:
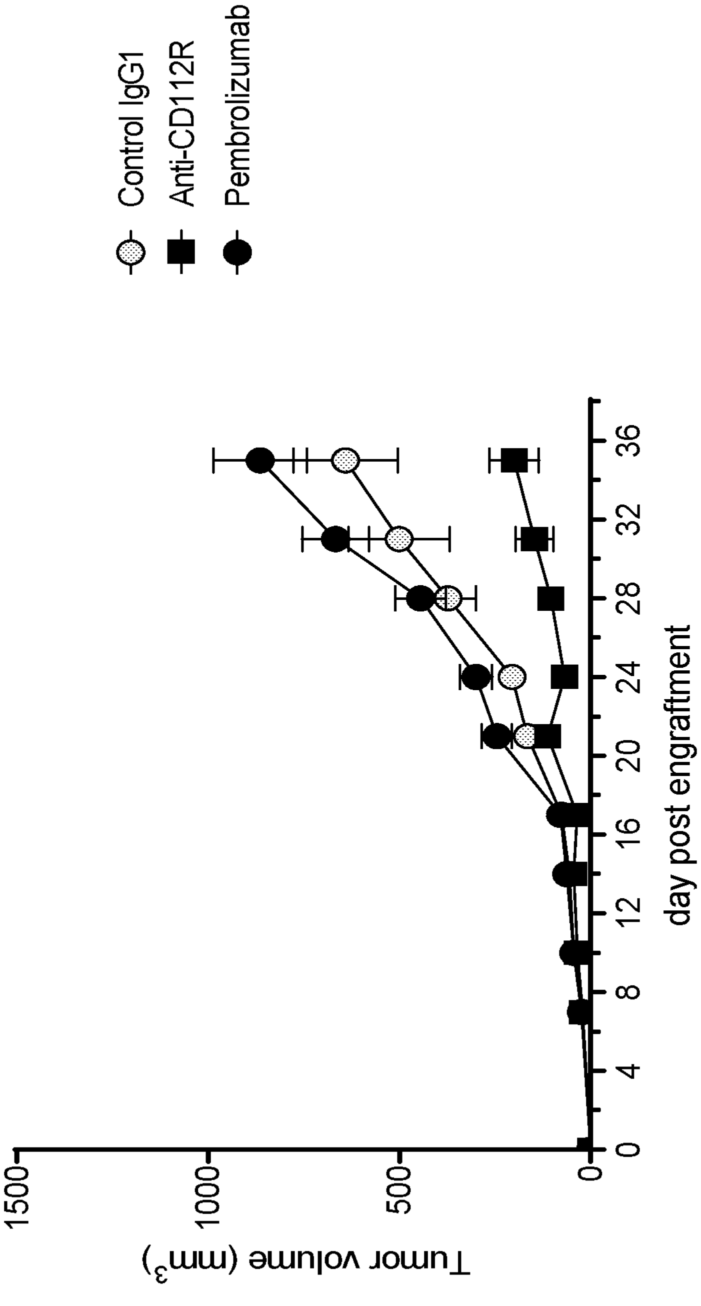
FIG. 12 demonstrates effect of in-vivo anti-CD112R mAb treatment on tumor growth in a mouse model. A549 cells were s.c. co-implanted with fresh human PBMCs at 1:5 E:T ratio to NSG-HLA-A2/HHD mice. Treatment started on day 3 post implantation. Mice were treated once weekly with either control IgG1, or with anti-CD112R mAb, or with anti PD-1 mAb (Pembrolizumab), all at 10 mg/kg for a total of 5 doses. $p=0.001$ by two-way ANOVA.

In vivo efficacy of anti-CD112R mAb treatment was evaluated in mice. A549 cells were co-implanted at 1:5 E:T ratio with PBMCs from a healthy male donor ($1*10^6$ PBMCs mixed with $5*10^6$ A549 cells). Cell mixture was s.c. implanted at the rear flank of NSG-HLA-A2/HHD male mice at a 1:1 volume ratio cells-in-PBS:Matrigel (Matrigel® Matrix, Corning REF 356234), in a final volume of 100 l/animal. On day 3 post implantation, treatment with either control IgG1 mAb (InVivoMAb human IgG1 isotype control BE0297 Bioxcell) or with anti-CD112R mAb, or with anti-PD-1 mAb (Pembrolizumab), once weekly at 10 mg/kg for a total of 5 doses. Tumor volume was measured once weekly by a caliper. On day 35 the average tumor volume of the control IgG treated group was 641 $mm^3$ and the tumor volume of the anti PD-1 treated group was 840 $mm^3$ (FIG. 12). These results were not significantly different by two-way-ANOVA. On the other hand, the average volume of the anti CD112R-treated tumors was 200 $mm^3$, representing 68% tumor growth inhibition, and significant tumor reduction compared to IgG treated animals (***p=0.001 by two-way ANOVA).

Example 17. Antibody Sequences

TABLE 10 details of CDR sequences, variable regions sequences of the different clones and variant thereof, and scFv sequences.

| | Amino acid SEQ ID Nos: | Nucleotide SEQ ID Nos: |
|---|---|---|
| Clone 13 and variants | | |
| HC CDR1 | 1, 7 | |
| HC CDR2 | 2, 8 | |
| HC CDR3 | 3 | |
| LC CDR1 | 4 | |
| LC CDR2 | 5 | |
| LC CDR3 | 6 | |
| HC variable region | 17 | 16, 24 |
| LC variable region | 19 | 18, 25 |
| LC wherein X = N (deamidation site) or S | 26 | |
| LC wherein N31S (deamidation removal) | 27 | |
| HC wherein N-Linked glycosylation site $X_1$ = N (parental), D, A, Q, S, or T; $X_2$ = T (parental) or A | 28 | |
| HC variant 1 (H1) | 29 | |
| HC variant 2 (H2) | 30 | |
| HC variant 3 (H3) | 31 | |
| HC variant 4 (H4) | 32 | |
| HC variant 5 (H5) | 33 | |
| HC variant 6 (H6) | 34 | |
| HC variant 7 (H7) | 35 | |
| HC variant 8 (H8) | 36 | |
| HC variant 9 (H9) | 37 | |
| HC variant 10 (H10) | 38 | |
| HC variant 11 (H11) | 39 | |
| LC variant 1 (K1) | 40 | |
| LC variant 2 (K2) | 41 | |
| LC variant 3 (K3) | 42 | |
| scFv variants connected to hIgG1 | | |
| Variant_0 | 43 | |
| Variant 1 N28T LC | 44 | |
| Variants_2-11 | 45-54 | |
| Clone 15 | | |
| HC CDR1 | 9, 7 | |
| HC CDR2 | 10, 12 | |
| HC CDR3 | 3 | |
| LC CDR1 | 11 | |
| LC CDR2 | 5 | |
| LC CDR3 | 6 | |
| HC variable region | 21 | 20 |
| LV variable region | 23 | 22 |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

The invention claimed is:

1. An antibody or antibody fragment thereof that binds to CD112R comprising a set of six CDRs wherein: heavy chain CDR1 sequence comprising the sequence GY$X_1$F$X_2$SY (SEQ ID NO: 1), wherein $X_1$ denotes N, D, A, Q, S, or T, and $X_2$ is T or A, or the sequence SYWIN (SEQ ID NO: 7), heavy chain CDR2 comprising the sequence YPGSYIP (SEQ ID NO: 2) or FPGSYS (SEQ ID NO: 10), heavy chain CDR3 comprising the sequence GYFDV (SEQ ID NO: 3), light chain CDR1 comprising the sequence KSSQSLLXSGNQKNYLA (SEQ ID NO: 4), wherein X denotes N or S, light chain CDR2 comprising the sequence GASTRES (SEQ ID NO: 5), and light chain CDR3 comprising the sequence QNDHSYPYT (SEQ ID NO: 6).

2. The antibody or antibody fragment according to claim 1, wherein the antibody is a humanized antibody.

3. The humanized antibody or the antibody fragment according to claim 2, comprising a set of six CDRs according to Kabat, wherein: heavy chain CDR1 sequence comprising the sequence SYWIN (SEQ ID NO: 7), heavy chain CDR2 comprising the sequence DIYPGSYIPNYNEKFKN (SEQ ID NO: 8), heavy chain CDR3 comprising the sequence GYFDV (SEQ ID NO: 3), light chain CDR1 comprising the sequence KSSQSLLSSGNQKNYLA (SEQ ID NO: 15), light chain CDR2 comprising the sequence GASTRES (SEQ ID NO: 5), and light chain CDR3 comprising the sequence QNDHSYPYT (SEQ ID NO: 6).

4. The humanized antibody or the antibody fragment according to claim 2, comprising a set of six CDRs according to Chothia, wherein: (i) heavy chain CDR1 sequence comprising the sequence GYTFTSY (SEQ ID NO: 13), heavy chain CDR2 comprising the sequence YPGSYIP (SEQ ID NO: 2), heavy chain CDR3 comprising the sequence GYFDV (SEQ ID NO: 3), light chain CDR1 comprising the sequence KSSQSLLSSGNQKNYLA (SEQ ID NO: 15), light chain CDR2 comprising the sequence GASTRES (SEQ ID NO: 5), and light chain CDR3 comprising the sequence QNDHSYPYT (SEQ ID NO: 6).

5. The humanized antibody or antibody fragment according to claim 2, wherein the humanized antibody or antibody fragment comprises a heavy chain comprising a variable region sequence selected from the group consisting of SEQ ID NOs: 29, 30, 31, 32, 33, 34, 35, 36, 37, 38, and 39; or an analog having at least 95% sequence similarity with said heavy chain variable region sequence; and a light chain comprising a variable region sequence selected from the group consisting of SEQ ID NOs: 40, 41, and 42; or an analog having at least 95% sequence similarity with said heavy chain variable region sequence.

6. The humanized antibody according to claim 2 comprising a combination of heavy and light chains selected from the group consisting of:

(i) heavy chain comprising SEQ ID NO: 39 and light chain comprising SEQ ID NO: 40;

(ii) heavy chain comprising SEQ ID NO: 39 and light chain comprising SEQ ID NO: 41; and (iii) heavy chain comprising SEQ ID NO: 39 and light chain comprising SEQ ID NO: 42.

7. An antibody fragment according to claim 1, wherein the antibody fragment is a single chain Fv (scFv).

8. A polypeptide comprising a scFv according to claim 7 and a human IgG1 Fc region sequence, wherein the polypeptide comprises a sequence set forth in any one of SEQ ID NOs: 43 to 54, or an analog or derivative thereof having at least 90% sequence identity to said polypeptide.

9. The antibody or antibody fragment according to claim 1, wherein the antibody binds to human CD112R with an affinity of at least $1\times10^{-9}$M.

10. A polynucleotide molecule or a pair of polynucleotide molecules encoding a heavy chain and a light chain variable region of the antibody or antibody fragment according to claim 5.

11. The polynucleotide molecule or the pair of polynucleotide molecules of claim 10, wherein the heavy chain variable region comprises a sequence selected from the group consisting of SEQ ID NO: 16, SEQ ID NO: 20, and SEQ ID NO: 24 or a variant thereof having at least 85% identity to said sequences.

12. The polynucleotide molecule or the pair of polynucleotide molecules of claim 11, wherein the light chain variable region is selected from the group consisting of: SEQ ID NO: 18, SEQ ID NO: 22 and SEQ ID NO: 25, or a variant thereof having at least 85% identity to said sequences.

13. A plasmid comprising the polynucleotide or the pair of polynucleotide molecules according to claim 10.

14. A pharmaceutical composition comprising as an active ingredient, at least one antibody or fragment thereof, according to claim 1, and a pharmaceutical acceptable excipient, diluent, salt or carrier.

15. A method of enhancing immune activity against cancer cells overexpressing Nectin-2, or for treating cancer, comprising administering to a subject in need thereof, a therapeutically effective amount of the pharmaceutical composition according to claim 14.

16. The method of claim 15, further comprising administering an additional anti-cancer therapy selected from surgery, chemotherapy, radiotherapy, and immunotherapy.

17. The method of claim 15, further comprising administering to said subject an additional immuno-modulator, activated lymphocyte cell, kinase inhibitor, chemotherapeutic agent, or any other anti-cancer agent.

18. The method of claim 17, wherein the additional immune-modulator is an antibody against an immune checkpoint molecule.

19. The method of claim 18, wherein the additional immune-modulator is an antibody selected from the group consisting of anti-PD-1, anti-TIGIT, anti-PVR and any combination thereof.

20. A method of diagnosing or prognosing cancer in a subject, the method comprises determining the expression level of CD112R in a biological sample of said subject using at least one antibody or antibody fragment is according to claim 1.

21. A pharmaceutical composition comprising as an active ingredient, at least one antibody or fragment thereof, comprising a combination of heavy and light chains selected from the group consisting of:

(i) heavy chain comprising SEQ ID NO: 39 and light chain comprising SEQ ID NO: 40;

(ii) heavy chain comprising SEQ ID NO: 39 and light chain comprising SEQ ID NO: 41; and (iii) heavy chain comprising SEQ ID NO: 39 and light chain comprising SEQ ID NO: 42, and a pharmaceutical acceptable excipient, diluent, salt or carrier.

22. A method of enhancing immune activity against cancer cells overexpressing Nectin-2, or for treating cancer, comprising administering to a subject in need thereof, a therapeutically effective amount of the pharmaceutical composition according to claim 21.

* * * * *

SEQUENCE LISTING

<160> NUMBER OF SEQ ID NOS: 54

<210> SEQ ID NO 1
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X=N, D, A, Q, S, or T
<220> FEATURE:
<221> NAME/KEY: MISC_FEATURE
<222> LOCATION: (5)..(5)
<223> OTHER INFORMATION: X=T or A

<400> SEQUENCE: 1

Gly Tyr Xaa Phe Xaa Ser Tyr
1               5

<210> SEQ ID NO 2
<211> LENGTH: 7
<212> TYPE: PRT
<213> ORGANISM: Mus musculus

<400> SEQUENCE: 2

Tyr Pro Gly Ser Tyr Ile Pro
1               5

<210> SEQ ID NO 3
<211> LENGTH: 5
<212> TYPE: PRT
<213> ORGANISM: Mus musculus

<400> SEQUENCE: 3

Gly Tyr Phe Asp Val
1               5

<210> SEQ ID NO 4
<211> LENGTH: 17
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (8)..(8)
<223> OTHER INFORMATION: X=N or S

<400> SEQUENCE: 4

Lys Ser Ser Gln Ser Leu Leu Xaa Ser Gly Asn Gln Lys Asn Tyr Leu
1               5                   10                  15

Ala

<210> SEQ ID NO 5
<211> LENGTH: 7
<212> TYPE: PRT
<213> ORGANISM: Mus musculus

<400> SEQUENCE: 5

Gly Ala Ser Thr Arg Glu Ser
1               5

<210> SEQ ID NO 6
<211> LENGTH: 9
<212> TYPE: PRT

<213> ORGANISM: Mus musculus

<400> SEQUENCE: 6

Gln Asn Asp His Ser Tyr Pro Tyr Thr
1 5

<210> SEQ ID NO 7
<211> LENGTH: 5
<212> TYPE: PRT
<213> ORGANISM: Mus musculus

<400> SEQUENCE: 7

Ser Tyr Trp Ile Asn
1 5

<210> SEQ ID NO 8
<211> LENGTH: 17
<212> TYPE: PRT
<213> ORGANISM: Mus musculus

<400> SEQUENCE: 8

Asp Ile Tyr Pro Gly Ser Tyr Ile Pro Asn Tyr Asn Glu Lys Phe Lys
1 5 10 15

Asn

<210> SEQ ID NO 9
<211> LENGTH: 7
<212> TYPE: PRT
<213> ORGANISM: Mus musculus

<400> SEQUENCE: 9

Gly Tyr Asn Phe Thr Ser Tyr
1 5

<210> SEQ ID NO 10
<211> LENGTH: 6
<212> TYPE: PRT
<213> ORGANISM: Mus musculus

<400> SEQUENCE: 10

Phe Pro Gly Ser Tyr Ser
1 5

<210> SEQ ID NO 11
<211> LENGTH: 17
<212> TYPE: PRT
<213> ORGANISM: Mus musculus

<400> SEQUENCE: 11

Lys Ser Ser Gln Ser Leu Leu Asn Ser Gly Ser Gln Lys Asn Tyr Leu
1 5 10 15

Ala

<210> SEQ ID NO 12
<211> LENGTH: 17
<212> TYPE: PRT
<213> ORGANISM: Mus musculus

<400> SEQUENCE: 12

Asp Ile Phe Pro Gly Ser Tyr Ser Pro Asn Tyr Asn Lys Lys Phe Lys
1 5 10 15

Arg

<210> SEQ ID NO 13
<211> LENGTH: 7
<212> TYPE: PRT
<213> ORGANISM: Artificial sequence
<220> FEATURE:
<223> OTHER INFORMATION: Synthetic sequence

<400> SEQUENCE: 13

Gly Tyr Thr Phe Thr Ser Tyr
1 5

<210> SEQ ID NO 14
<211> LENGTH: 7
<212> TYPE: PRT
<213> ORGANISM: Artificial sequence
<220> FEATURE:
<223> OTHER INFORMATION: Synthetic sequence

<400> SEQUENCE: 14

Gly Tyr Asn Phe Ala Ser Tyr
1 5

<210> SEQ ID NO 15
<211> LENGTH: 17
<212> TYPE: PRT
<213> ORGANISM: Artificial sequence
<220> FEATURE:
<223> OTHER INFORMATION: Synthetic sequence

<400> SEQUENCE: 15

Lys Ser Ser Gln Ser Leu Leu Ser Ser Gly Asn Gln Lys Asn Tyr Leu
1 5 10 15

Ala

<210> SEQ ID NO 16
<211> LENGTH: 342
<212> TYPE: DNA
<213> ORGANISM: Artificial sequence
<220> FEATURE:
<223> OTHER INFORMATION: Synthetic sequence

<400> SEQUENCE: 16
caggtccaac tgcagcagcc tggggctgag cttgtgaagc ctgggacttc agtgaagctg 60
tcctgcaagg cttctggcta caacttcacc agctactgga taaactgggt gaagctgagg 120
cctggacaag gccttgagtg gattggagat atttatcctg gtagttatat tcctaactac 180
aatgagaagt tcaagaacaa ggccacactg actgtagaca catcctccag cacagcctac 240
atgcaactca ccagcctggc atctgaggac tctgctctct attactgtgc aggagggtac 300
ttcgatgtct ggggcgcagg gaccacggtc accgtctcct ca 342

<210> SEQ ID NO 17
<211> LENGTH: 114
<212> TYPE: PRT
<213> ORGANISM: Artificial sequence
<220> FEATURE:
<223> OTHER INFORMATION: Synthetic sequence

<400> SEQUENCE: 17

Gln Val Gln Leu Gln Gln Pro Gly Ala Glu Leu Val Lys Pro Gly Thr
1 5 10 15

Ser Val Lys Leu Ser Cys Lys Ala Ser Gly Tyr Asn Phe Thr Ser Tyr
20 25 30

Trp Ile Asn Trp Val Lys Leu Arg Pro Gly Gln Gly Leu Glu Trp Ile
35 40 45

Gly Asp Ile Tyr Pro Gly Ser Tyr Ile Pro Asn Tyr Asn Glu Lys Phe
50 55 60

Lys Asn Lys Ala Thr Leu Thr Val Asp Thr Ser Ser Ser Thr Ala Tyr
65 70 75 80

Met Gln Leu Thr Ser Leu Ala Ser Glu Asp Ser Ala Leu Tyr Tyr Cys
85 90 95

Ala Gly Gly Tyr Phe Asp Val Trp Gly Ala Gly Thr Thr Val Thr Val
100 105 110

Ser Ser

<210> SEQ ID NO 18
<211> LENGTH: 339
<212> TYPE: DNA
<213> ORGANISM: Artificial sequence
<220> FEATURE:
<223> OTHER INFORMATION: Synthetic sequence

<400> SEQUENCE: 18
gacattgtga tgacacagtc tccatcctcc ctgagtgtgt cagcaggaga gaaggtcact 60
atgagttgca agtccagtca gagtctatta aacagtggaa atcaaaagaa ctacttggcc 120
tggtaccagc agaaaccagg acagcctcct aaactgttga tctacggggc ttccactagg 180
gaatctgggg tccctgatcg cttcacaggc agtggatctg gaaccgattt cactcttacc 240
atcagcagtg tgcaggctga agacctggca gtttattact gtcagaatga tcatagttat 300
ccgtacacgt tcggaggggg gaccaagctg gaaataaaa 339

<210> SEQ ID NO 19
<211> LENGTH: 113
<212> TYPE: PRT
<213> ORGANISM: Artificial sequence
<220> FEATURE:
<223> OTHER INFORMATION: Synthetic sequence

<400> SEQUENCE: 19

Asp Ile Val Met Thr Gln Ser Pro Ser Ser Leu Ser Val Ser Ala Gly
1 5 10 15

Glu Lys Val Thr Met Ser Cys Lys Ser Ser Gln Ser Leu Leu Asn Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp His Ser Tyr Pro Tyr Thr Phe Gly Gly Gly Thr Lys Leu Glu Ile
100 105 110

Lys

<210> SEQ ID NO 20
<211> LENGTH: 342
<212> TYPE: DNA
<213> ORGANISM: Artificial sequence
<220> FEATURE:
<223> OTHER INFORMATION: Synthetic sequence

<400> SEQUENCE: 20
caggtccaac tgcagcagcc tggggctgag cttgtgaagc ctgggacttc agtgaagctg 60
tcctgcaagg cttctggcta caacttcacc agctactgga taaactgggt gaagctgagg 120
cctggacaag gccttgagtg gattggagat atttttcctg gtagttatag tcctaactac 180
aataagaagt tcaagcgcaa ggccacactg actgtagaca catcctccag cacagcctac 240
atgcaactca gcagcctggc atctgaggac tctgctctct attactgtgc aggaggatac 300
ttcgatgtct ggggcgcagg gaccacggtc accgtctcct ca 342

<210> SEQ ID NO 21
<211> LENGTH: 114
<212> TYPE: PRT
<213> ORGANISM: Artificial sequence
<220> FEATURE:
<223> OTHER INFORMATION: Synthetic sequence

<400> SEQUENCE: 21

```
Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Asn Phe Thr Ser Tyr
            20                  25                  30

Trp Ile Asn Trp Val Lys Leu Arg Pro Gly Gln Gly Leu Glu Trp Ile
        35                  40                  45

Gly Asp Ile Phe Pro Gly Ser Tyr Ser Pro Asn Tyr Asn Lys Lys Phe
    50                  55                  60

Lys Arg Lys Ala Thr Leu Thr Val Asp Thr Ser Ser Ser Thr Ala Tyr
65                  70                  75                  80

Met Gln Leu Ser Ser Leu Ala Ser Glu Asp Ser Ala Leu Tyr Tyr Cys
                85                  90                  95

Ala Gly Gly Tyr Phe Asp Val Trp Gly Ala Gly Thr Thr Val Thr Val
            100                 105                 110

Ser Ser
```

<210> SEQ ID NO 22
<211> LENGTH: 339
<212> TYPE: DNA
<213> ORGANISM: Artificial sequence
<220> FEATURE:
<223> OTHER INFORMATION: Synthetic sequence

<400> SEQUENCE: 22
gacattgtga tgacacagtc tccatcctcc ctgagtgtgt cagcaggaga gaaggtcact 60
atgagctgca agtccagtca gagtctgtta aacagtggaa gtcaaaagaa ctacttggcc 120
tggtaccagc agaaaccagg gcagcctcct aaactgttga tctacggggc atccactagg 180
gaatctgggg tccctgatcg cttcacaggc agtggatctg gaaccgattt cactcttacc 240
atcagctttg tgcaggctga agacctggca gtttattact gtcagaatga tcatagttat 300
ccgtacacgt tcggaggggg gaccaagctg gaaataaaa 339

<210> SEQ ID NO 23
<211> LENGTH: 113
<212> TYPE: PRT
<213> ORGANISM: Artificial sequence
<220> FEATURE:
<223> OTHER INFORMATION: Synthetic sequence

<400> SEQUENCE: 23

```
Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Ser Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Phe Val Gln Ala Glu Asp Leu Ala Val Tyr Tyr Cys Gln Asn
                85                  90                  95

Asp His Ser Tyr Pro Tyr Thr Phe Gly Gly Gly Thr Lys Leu Glu Ile
            100                 105                 110

Lys


<210> SEQ ID NO 24
<211> LENGTH: 342
<212> TYPE: DNA
<213> ORGANISM: Artificial sequence
<220> FEATURE:
<223> OTHER INFORMATION: Synthetic sequence

<400> SEQUENCE: 24

caggtccaac tgcagcagcc tggggctgag cttgtgaagc ctgggacttc agtgaagctg     60

tcctgcaagg cttctggcta caacttcacc agctactgga taaactgggt gaagctgagg    120

cctggacaag gccttgagtg gattggagat atttatcctg gaagttatat tcctaactac    180

aatgagaagt tcaagaacaa ggccacactg actgtagaca catcctccag cacagcctac    240

atgcaactca ccagcctggc atctgaggac tctgctctct attactgtgc aggaggttac    300

ttcgatgtct ggggcgcagg gaccacggtc accgtctcct ca                       342


<210> SEQ ID NO 25
<211> LENGTH: 339
<212> TYPE: DNA
<213> ORGANISM: Artificial sequence
<220> FEATURE:
<223> OTHER INFORMATION: Synthetic sequence

<400> SEQUENCE: 25

gacattgtga tgacacagtc tccatcctcc ctgagtgtgt cagcaggaga gaaggtcact     60

atgagctgca agtccagtca gagtctgtta aacagtggaa atcaaaagaa ctacttggcc    120

tggtaccagc agaaaccagg acagcctcct aaactgttga tctacggggc ttccactagg    180

gaatctgggg tccctgatcg cttcacaggc agtggatctg gaaccgattt cactcttacc    240

atcagcagtg tgcaggctga agacctggca gtttattact gtcagaatga tcatagttat    300

ccgtacacgt tcggaggggg gaccaagctg gaaataaaa                           339


<210> SEQ ID NO 26
<211> LENGTH: 113
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (31)..(31)
<223> OTHER INFORMATION: X=N or S
```

<400> SEQUENCE: 26

Asp Ile Val Met Thr Gln Ser Pro Ser Ser Leu Ser Val Ser Ala Gly
1 5 10 15

Glu Lys Val Thr Met Ser Cys Lys Ser Ser Gln Ser Leu Leu Xaa Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp His Ser Tyr Pro Tyr Thr Phe Gly Gly Gly Thr Lys Leu Glu Ile
100 105 110

Lys

<210> SEQ ID NO 27
<211> LENGTH: 113
<212> TYPE: PRT
<213> ORGANISM: Artificial sequence
<220> FEATURE:
<223> OTHER INFORMATION: Synthetic sequence

<400> SEQUENCE: 27

Asp Ile Val Met Thr Gln Ser Pro Ser Ser Leu Ser Val Ser Ala Gly
1 5 10 15

Glu Lys Val Thr Met Ser Cys Lys Ser Ser Gln Ser Leu Leu Ser Ser
20 25 30

Gly Asn Gln Lys Asn Tyr Leu Ala Trp Tyr Gln Gln Lys Pro Gly Gln
35 40 45

Pro Pro Lys Leu Leu Ile Tyr Gly Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Gln Asn
85 90 95

Asp His Ser Tyr Pro Tyr Thr Phe Gly Gly Gly Thr Lys Leu Glu Ile
100 105 110

Lys

<210> SEQ ID NO 28
<211> LENGTH: 114
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (28)..(28)
<223> OTHER INFORMATION: X= N, D, A, Q, S, or T
<220> FEATURE:
<221> NAME/KEY: MISC_FEATURE
<222> LOCATION: (30)..(30)
<223> OTHER INFORMATION: X=T or A

<400> SEQUENCE: 28

Gln Val Gln Leu Gln Gln Pro Gly Ala Glu Leu Val Lys Pro Gly Thr
1 5 10 15

```
Ser Val Lys Leu Ser Cys Lys Ala Ser Gly Tyr Xaa Phe Xaa Ser Tyr
            20                  25                  30

Trp Ile Asn Trp Val Lys Leu Arg Pro Gly Gln Gly Leu Glu Trp Ile
        35                  40                  45

Gly Asp Ile Tyr Pro Gly Ser Tyr Ile Pro Asn Tyr Asn Glu Lys Phe
    50                  55                  60

Lys Asn Lys Ala Thr Leu Thr Val Asp Thr Ser Ser Ser Thr Ala Tyr
65                  70                  75                  80

Met Gln Leu Thr Ser Leu Ala Ser Glu Asp Ser Ala Leu Tyr Tyr Cys
                85                  90                  95

Ala Gly Gly Tyr Phe Asp Val Trp Gly Ala Gly Thr Thr Val Thr Val
            100                 105                 110

Ser Ser


<210> SEQ ID NO 29
<211> LENGTH: 114
<212> TYPE: PRT
<213> ORGANISM: Artificial sequence
<220> FEATURE:
<223> OTHER INFORMATION: Synthetic sequence

<400> SEQUENCE: 29

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Thr Ser Tyr
            20                  25                  30

Trp Ile Asn Trp Val Lys Leu Arg Pro Gly Gln Gly Leu Glu Trp Ile
        35                  40                  45

Gly Asp Ile Tyr Pro Gly Ser Tyr Ile Pro Asn Tyr Asn Glu Lys Phe
    50                  55                  60

Lys Asn Lys Ala Thr Leu Thr Val Asp Thr Ser Ser Ser Thr Ala Tyr
65                  70                  75                  80

Met Gln Leu Thr Ser Leu Ala Ser Glu Asp Ser Ala Leu Tyr Tyr Cys
                85                  90                  95

Ala Gly Gly Tyr Phe Asp Val Trp Gly Ala Gly Thr Thr Val Thr Val
            100                 105                 110

Ser Ser


<210> SEQ ID NO 30
<211> LENGTH: 114
<212> TYPE: PRT
<213> ORGANISM: Artificial sequence
<220> FEATURE:
<223> OTHER INFORMATION: Synthetic sequence

<400> SEQUENCE: 30

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Thr Ser Tyr
            20                  25                  30

Trp Ile Asn Trp Val Lys Leu Ala Pro Gly Gln Gly Leu Glu Trp Ile
        35                  40                  45

Gly Asp Ile Tyr Pro Gly Ser Tyr Ile Pro Asn Tyr Asn Glu Lys Phe
    50                  55                  60

Lys Asn Arg Ala Thr Leu Thr Val Asp Thr Ser Ala Ser Thr Ala Tyr
65                  70                  75                  80
```

```
Met Glu Leu Ser Ser Leu Ala Ser Glu Asp Ser Ala Leu Tyr Tyr Cys
                85                  90                  95

Ala Gly Gly Tyr Phe Asp Val Trp Gly Gln Gly Thr Thr Val Thr Val
            100                 105                 110

Ser Ser


<210> SEQ ID NO 31
<211> LENGTH: 114
<212> TYPE: PRT
<213> ORGANISM: Artificial sequence
<220> FEATURE:
<223> OTHER INFORMATION: Synthetic sequence

<400> SEQUENCE: 31

Gln Val Gln Leu Val Gln Ser Gly Ala Glu Leu Lys Lys Pro Gly Ser
1               5                   10                  15

Ser Val Lys Leu Ser Cys Lys Ala Ser Gly Tyr Thr Phe Thr Ser Tyr
            20                  25                  30

Trp Ile Asn Trp Val Lys Leu Arg Pro Gly Gln Gly Leu Glu Trp Ile
        35                  40                  45

Gly Asp Ile Tyr Pro Gly Ser Tyr Ile Pro Asn Tyr Asn Glu Lys Phe
    50                  55                  60

Lys Asn Arg Ala Thr Leu Thr Val Asp Thr Ser Ala Ser Thr Ala Tyr
65                  70                  75                  80

Met Glu Leu Ser Ser Leu Ala Ser Glu Asp Ser Ala Leu Tyr Tyr Cys
                85                  90                  95

Ala Gly Gly Tyr Phe Asp Val Trp Gly Gln Gly Thr Thr Val Thr Val
            100                 105                 110

Ser Ser


<210> SEQ ID NO 32
<211> LENGTH: 114
<212> TYPE: PRT
<213> ORGANISM: Artificial sequence
<220> FEATURE:
<223> OTHER INFORMATION: Synthetic sequence

<400> SEQUENCE: 32

Gln Val Gln Leu Val Gln Ser Gly Ala Glu Leu Lys Lys Pro Gly Ser
1               5                   10                  15

Ser Val Lys Leu Ser Cys Lys Ala Ser Gly Tyr Thr Phe Thr Ser Tyr
            20                  25                  30

Trp Ile Asn Trp Val Lys Leu Ala Pro Gly Gln Gly Leu Glu Trp Ile
        35                  40                  45

Gly Asp Ile Tyr Pro Gly Ser Tyr Ile Pro Asn Tyr Asn Glu Lys Phe
    50                  55                  60

Lys Asn Lys Ala Thr Leu Thr Val Asp Thr Ser Ser Ser Thr Ala Tyr
65                  70                  75                  80

Met Gln Leu Thr Ser Leu Ala Ser Glu Asp Ser Ala Leu Tyr Tyr Cys
                85                  90                  95

Ala Gly Gly Tyr Phe Asp Val Trp Gly Gln Gly Thr Thr Val Thr Val
            100                 105                 110

Ser Ser


<210> SEQ ID NO 33
<211> LENGTH: 114
<212> TYPE: PRT
<213> ORGANISM: Artificial sequence
```

<220> FEATURE:
<223> OTHER INFORMATION: Synthetic sequence

<400> SEQUENCE: 33

Gln Val Gln Leu Val Gln Ser Gly Ala Glu Leu Lys Lys Pro Gly Ser
1 5 10 15

Ser Val Lys Leu Ser Cys Lys Ala Ser Gly Tyr Thr Phe Thr Ser Tyr
20 25 30

Trp Ile Asn Trp Val Lys Leu Ala Pro Gly Gln Gly Leu Glu Trp Ile
35 40 45

Gly Asp Ile Tyr Pro Gly Ser Tyr Ile Pro Asn Tyr Asn Glu Lys Phe
50 55 60

Lys Asn Lys Ala Thr Leu Thr Val Asp Thr Ser Ala Ser Thr Ala Tyr
65 70 75 80

Met Gln Leu Thr Ser Leu Ala Ser Glu Asp Ser Ala Leu Tyr Tyr Cys
85 90 95

Ala Gly Gly Tyr Phe Asp Val Trp Gly Gln Gly Thr Thr Val Thr Val
100 105 110

Ser Ser

<210> SEQ ID NO 34
<211> LENGTH: 114
<212> TYPE: PRT
<213> ORGANISM: Artificial sequence
<220> FEATURE:
<223> OTHER INFORMATION: Synthetic sequence

<400> SEQUENCE: 34

Gln Val Gln Leu Val Gln Ser Gly Ala Glu Leu Lys Lys Pro Gly Ser
1 5 10 15

Ser Val Lys Leu Ser Cys Lys Ala Ser Gly Tyr Thr Phe Thr Ser Tyr
20 25 30

Trp Ile Asn Trp Val Lys Leu Ala Pro Gly Gln Gly Leu Glu Trp Ile
35 40 45

Gly Asp Ile Tyr Pro Gly Ser Tyr Ile Pro Asn Tyr Asn Glu Lys Phe
50 55 60

Lys Asn Arg Ala Thr Leu Thr Val Asp Thr Ser Ala Ser Thr Ala Tyr
65 70 75 80

Met Glu Leu Ser Ser Leu Ala Ser Glu Asp Ser Ala Leu Tyr Tyr Cys
85 90 95

Ala Gly Gly Tyr Phe Asp Val Trp Gly Gln Gly Thr Thr Val Thr Val
100 105 110

Ser Ser

<210> SEQ ID NO 35
<211> LENGTH: 114
<212> TYPE: PRT
<213> ORGANISM: Artificial sequence
<220> FEATURE:
<223> OTHER INFORMATION: Synthetic sequence

<400> SEQUENCE: 35

Gln Val Gln Leu Val Gln Ser Gly Ala Glu Val Lys Lys Pro Gly Ser
1 5 10 15

Ser Val Lys Leu Ser Cys Lys Ala Ser Gly Tyr Thr Phe Thr Ser Tyr
20 25 30

Trp Ile Asn Trp Val Lys Leu Ala Pro Gly Gln Gly Leu Glu Trp Ile
35 40 45

Gly Asp Ile Tyr Pro Gly Ser Tyr Ile Pro Asn Tyr Asn Glu Lys Phe
50 55 60

Lys Asn Arg Ala Thr Leu Thr Val Asp Thr Ser Ala Ser Thr Ala Tyr
65 70 75 80

Met Glu Leu Ser Ser Leu Ala Ser Glu Asp Thr Ala Leu Tyr Tyr Cys
85 90 95

Ala Gly Gly Tyr Phe Asp Val Trp Gly Gln Gly Thr Thr Val Thr Val
100 105 110

Ser Ser

<210> SEQ ID NO 36
<211> LENGTH: 114
<212> TYPE: PRT
<213> ORGANISM: Artificial sequence
<220> FEATURE:
<223> OTHER INFORMATION: Synthetic sequence

<400> SEQUENCE: 36

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile Asn Trp Val Lys Leu Ala Pro Gly Gln Gly Leu Glu Trp Ile
35 40 45

Gly Asp Ile Tyr Pro Gly Ser Tyr Ile Pro Asn Tyr Asn Glu Lys Phe
50 55 60

Lys Asn Arg Ala Thr Leu Thr Val Asp Thr Ser Ala Ser Thr Ala Tyr
65 70 75 80

Met Glu Leu Ser Ser Leu Ala Ser Glu Asp Thr Ala Leu Tyr Tyr Cys
85 90 95

Ala Gly Gly Tyr Phe Asp Val Trp Gly Gln Gly Thr Thr Val Thr Val
100 105 110

Ser Ser

<210> SEQ ID NO 37
<211> LENGTH: 114
<212> TYPE: PRT
<213> ORGANISM: Artificial sequence
<220> FEATURE:
<223> OTHER INFORMATION: Synthetic sequence

<400> SEQUENCE: 37

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Trp Ile Asn Trp Val Lys Leu Ala Pro Gly Gln Gly Leu Glu Trp Ile
35 40 45

Gly Asp Ile Tyr Pro Gly Ser Tyr Ile Pro Asn Tyr Asn Glu Lys Phe
50 55 60

Lys Asn Arg Ala Thr Leu Thr Val Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Gly Gly Tyr Phe Asp Val Trp Gly Gln Gly Thr Thr Val Thr Val
100 105 110

Ser Ser

<210> SEQ ID NO 38
<211> LENGTH: 114
<212> TYPE: PRT
<213> ORGANISM: Artificial sequence
<220> FEATURE:
<223> OTHER INFORMATION: Synthetic sequence

<400> SEQUENCE: 38

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly Asp Ile Tyr Pro Gly Ser Tyr Ile Pro Asn Tyr Asn Glu Lys Phe
    50                  55                  60

Lys Asn Arg Ala Thr Leu Thr Val Asp Thr Ser Ala Ser Thr Ala Tyr
65                  70                  75                  80

Met Glu Leu Ser Ser Leu Ala Ser Glu Asp Thr Ala Leu Tyr Tyr Cys
                85                  90                  95

Ala Gly Gly Tyr Phe Asp Val Trp Gly Gln Gly Thr Thr Val Thr Val
            100                 105                 110

Ser Ser
```

<210> SEQ ID NO 39
<211> LENGTH: 114
<212> TYPE: PRT
<213> ORGANISM: Artificial sequence
<220> FEATURE:
<223> OTHER INFORMATION: Synthetic sequence

<400> SEQUENCE: 39

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly Asp Ile Tyr Pro Gly Ser Tyr Ile Pro Asn Tyr Asn Glu Lys Phe
    50                  55                  60

Lys Asn Arg Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Tyr Phe Asp Val Trp Gly Gln Gly Thr Thr Val Thr Val
            100                 105                 110

Ser Ser
```

<210> SEQ ID NO 40
<211> LENGTH: 113
<212> TYPE: PRT
<213> ORGANISM: Artificial sequence
<220> FEATURE:
<223> OTHER INFORMATION: Synthetic sequence

<400> SEQUENCE: 40

```
Asp Ile Val Met Thr Gln Ser Pro Asp Ser Leu Ser Val Ser Leu Gly
```

```
1               5                   10                  15

Glu Arg Ala Thr Ile Asn Cys Lys Ser Ser Gln Ser Leu Leu Ser Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Ser Tyr Pro Tyr Thr Phe Gly Gln Gly Thr Lys Leu Glu Ile
            100                 105                 110

Lys


<210> SEQ ID NO 41
<211> LENGTH: 113
<212> TYPE: PRT
<213> ORGANISM: Artificial sequence
<220> FEATURE:
<223> OTHER INFORMATION: Synthetic sequence

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Ser Tyr Pro Tyr Thr Phe Gly Gln Gly Thr Lys Leu Glu Ile
            100                 105                 110

Lys


<210> SEQ ID NO 42
<211> LENGTH: 113
<212> TYPE: PRT
<213> ORGANISM: Artificial sequence
<220> FEATURE:
<223> OTHER INFORMATION: Synthetic sequence

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Asn
                85                  90                  95

Asp His Ser Tyr Pro Tyr Thr Phe Gly Gln Gly Thr Lys Leu Glu Ile
            100                 105                 110

Lys


<210> SEQ ID NO 43
<211> LENGTH: 488
<212> TYPE: PRT
<213> ORGANISM: Artificial sequence
<220> FEATURE:
<223> OTHER INFORMATION: Synthetic sequence

<400> SEQUENCE: 43

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Thr Ser Val Lys Leu Ser Cys Lys Ala Ser Gly Tyr Asn Phe
        35                  40                  45

Thr Ser Tyr Trp Ile Asn Trp Val Lys Leu Arg Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Lys Ala Thr Leu Thr Val Asp Thr Ser Ser Ser
                85                  90                  95

Thr Ala Tyr Met Gln Leu Thr Ser Leu Ala Ser Glu Asp Ser Ala Leu
            100                 105                 110

Tyr Tyr Cys Ala Gly Gly Tyr Phe Asp Val Trp Gly Ala Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320
```

```
Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485


<210> SEQ ID NO 44
<211> LENGTH: 488
<212> TYPE: PRT
<213> ORGANISM: Artificial sequence
<220> FEATURE:
<223> OTHER INFORMATION: Synthetic sequence

<400> SEQUENCE: 44

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Thr Ser Val Lys Leu Ser Cys Lys Ala Ser Gly Tyr Thr Phe
        35                  40                  45

Thr Ser Tyr Trp Ile Asn Trp Val Lys Leu Arg Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Lys Ala Thr Leu Thr Val Asp Thr Ser Ser Ser
                85                  90                  95

Thr Ala Tyr Met Gln Leu Thr Ser Leu Ala Ser Glu Asp Ser Ala Leu
            100                 105                 110

Tyr Tyr Cys Ala Gly Gly Tyr Phe Asp Val Trp Gly Ala Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190
```

```
Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485


<210> SEQ ID NO 45
<211> LENGTH: 488
<212> TYPE: PRT
<213> ORGANISM: Artificial sequence
<220> FEATURE:
<223> OTHER INFORMATION: Synthetic sequence

<400> SEQUENCE: 45

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Thr Ser Val Lys Leu Ser Cys Lys Ala Ser Gly Tyr Thr Phe
        35                  40                  45

Thr Ser Tyr Trp Ile Asn Trp Val Lys Leu Ala Pro Gly Gln Gly Leu
    50                  55                  60
```

-continued

```
Glu Trp Ile Gly Asp Ile Tyr Pro Gly Ser Tyr Ile Pro Asn Tyr Asn
65                  70                  75                  80

Glu Lys Phe Lys Asn Arg Ala Thr Leu Thr Val Asp Thr Ser Ala Ser
                85                  90                  95

Thr Ala Tyr Met Glu Leu Ser Ser Leu Ala Ser Glu Asp Ser Ala Leu
            100                 105                 110

Tyr Tyr Cys Ala Gly Gly Tyr Phe Asp Val Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
```

485

<210> SEQ ID NO 46
<211> LENGTH: 488
<212> TYPE: PRT
<213> ORGANISM: Artificial sequence
<220> FEATURE:
<223> OTHER INFORMATION: Synthetic sequence

<400> SEQUENCE: 46

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Leu Lys Lys
            20                  25                  30

Pro Gly Ser Ser Val Lys Leu Ser Cys Lys Ala Ser Gly Tyr Thr Phe
        35                  40                  45

Thr Ser Tyr Trp Ile Asn Trp Val Lys Leu Arg Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Arg Ala Thr Leu Thr Val Asp Thr Ser Ala Ser
                85                  90                  95

Thr Ala Tyr Met Glu Leu Ser Ser Leu Ala Ser Glu Asp Ser Ala Leu
            100                 105                 110

Tyr Tyr Cys Ala Gly Gly Tyr Phe Asp Val Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala

```
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485
```

<210> SEQ ID NO 47
<211> LENGTH: 488
<212> TYPE: PRT
<213> ORGANISM: Artificial sequence
<220> FEATURE:
<223> OTHER INFORMATION: Synthetic sequence

<400> SEQUENCE: 47

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Leu Lys Lys
            20                  25                  30

Pro Gly Ser Ser Val Lys Leu Ser Cys Lys Ala Ser Gly Tyr Thr Phe
        35                  40                  45

Thr Ser Tyr Trp Ile Asn Trp Val Lys Leu Ala Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Lys Ala Thr Leu Thr Val Asp Thr Ser Ser Ser
                85                  90                  95

Thr Ala Tyr Met Gln Leu Thr Ser Leu Ala Ser Glu Asp Ser Ala Leu
            100                 105                 110

Tyr Tyr Cys Ala Gly Gly Tyr Phe Asp Val Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
```

```
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485


<210> SEQ ID NO 48
<211> LENGTH: 488
<212> TYPE: PRT
<213> ORGANISM: Artificial sequence
<220> FEATURE:
<223> OTHER INFORMATION: Synthetic sequence

<400> SEQUENCE: 48

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Leu Lys Lys
            20                  25                  30

Pro Gly Ser Ser Val Lys Leu Ser Cys Lys Ala Ser Gly Tyr Thr Phe
        35                  40                  45

Thr Ser Tyr Trp Ile Asn Trp Val Lys Leu Ala Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Lys Ala Thr Leu Thr Val Asp Thr Ser Ala Ser
                85                  90                  95

Thr Ala Tyr Met Gln Leu Thr Ser Leu Ala Ser Glu Asp Ser Ala Leu
```

```
            100                 105                 110

Tyr Tyr Cys Ala Gly Gly Tyr Phe Asp Val Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485
```

<210> SEQ ID NO 49
<211> LENGTH: 488
<212> TYPE: PRT
<213> ORGANISM: Artificial sequence
<220> FEATURE:
<223> OTHER INFORMATION: Synthetic sequence

<400> SEQUENCE: 49

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Leu Lys Lys
            20                  25                  30

Pro Gly Ser Ser Val Lys Leu Ser Cys Lys Ala Ser Gly Tyr Thr Phe
        35                  40                  45

Thr Ser Tyr Trp Ile Asn Trp Val Lys Leu Ala Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Arg Ala Thr Leu Thr Val Asp Thr Ser Ala Ser
                85                  90                  95

Thr Ala Tyr Met Glu Leu Ser Ser Leu Ala Ser Glu Asp Ser Ala Leu
            100                 105                 110

Tyr Tyr Cys Ala Gly Gly Tyr Phe Asp Val Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400
```

```
Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485


<210> SEQ ID NO 50
<211> LENGTH: 488
<212> TYPE: PRT
<213> ORGANISM: Artificial sequence
<220> FEATURE:
<223> OTHER INFORMATION: Synthetic sequence

<400> SEQUENCE: 50

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Leu Ser Cys Lys Ala Ser Gly Tyr Thr Phe
        35                  40                  45

Thr Ser Tyr Trp Ile Asn Trp Val Lys Leu Ala Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Arg Ala Thr Leu Thr Val Asp Thr Ser Ala Ser
                85                  90                  95

Thr Ala Tyr Met Glu Leu Ser Ser Leu Ala Ser Glu Asp Thr Ala Leu
            100                 105                 110

Tyr Tyr Cys Ala Gly Gly Tyr Phe Asp Val Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270
```

```
Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485


<210> SEQ ID NO 51
<211> LENGTH: 488
<212> TYPE: PRT
<213> ORGANISM: Artificial sequence
<220> FEATURE:
<223> OTHER INFORMATION: Synthetic sequence

<400> SEQUENCE: 51

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Trp Ile Asn Trp Val Lys Leu Ala Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Arg Ala Thr Leu Thr Val Asp Thr Ser Ala Ser
                85                  90                  95

Thr Ala Tyr Met Glu Leu Ser Ser Leu Ala Ser Glu Asp Thr Ala Leu
            100                 105                 110

Tyr Tyr Cys Ala Gly Gly Tyr Phe Asp Val Trp Gly Gln Gly Thr Thr
        115                 120                 125

Val Thr Val Ser Ser Gly Gly Gly Gly Ser Gly Gly Gly Gly Ser Gly
    130                 135                 140
```

Gly Gly Gly Ser Asp Ile Val Met Thr Gln Ser Pro Ser Ser Leu Ser
145 150 155 160

Val Ser Ala Gly Glu Lys Val Thr Met Ser Cys Lys Ser Ser Gln Ser
165 170 175

Leu Leu Ser Ser Gly Asn Gln Lys Asn Tyr Leu Ala Trp Tyr Gln Gln
180 185 190

Lys Pro Gly Gln Pro Pro Lys Leu Leu Ile Tyr Gly Ala Ser Thr Arg
195 200 205

Glu Ser Gly Val Pro Asp Arg Phe Thr Gly Ser Gly Ser Gly Thr Asp
210 215 220

Phe Thr Leu Thr Ile Ser Ser Val Gln Ala Glu Asp Leu Ala Val Tyr
225 230 235 240

Tyr Cys Gln Asn Asp His Ser Tyr Pro Tyr Thr Phe Gly Gly Gly Thr
245 250 255

Lys Leu Glu Ile Lys Asp Lys Thr His Thr Cys Pro Pro Cys Pro Ala
260 265 270

Pro Glu Leu Leu Gly Gly Pro Ser Val Phe Leu Phe Pro Pro Lys Pro
275 280 285

Lys Asp Thr Leu Met Ile Ser Arg Thr Pro Glu Val Thr Cys Val Val
290 295 300

Val Asp Val Ser His Glu Asp Pro Glu Val Lys Phe Asn Trp Tyr Val
305 310 315 320

Asp Gly Val Glu Val His Asn Ala Lys Thr Lys Pro Arg Glu Glu Gln
325 330 335

Tyr Asn Ser Thr Tyr Arg Val Val Ser Val Leu Thr Val Leu His Gln
340 345 350

Asp Trp Leu Asn Gly Lys Glu Tyr Lys Cys Lys Val Ser Asn Lys Ala
355 360 365

Leu Pro Ala Pro Ile Glu Lys Thr Ile Ser Lys Ala Lys Gly Gln Pro
370 375 380

Arg Glu Pro Gln Val Tyr Thr Leu Pro Pro Ser Arg Asp Glu Leu Thr
385 390 395 400

Lys Asn Gln Val Ser Leu Thr Cys Leu Val Lys Gly Phe Tyr Pro Ser
405 410 415

Asp Ile Ala Val Glu Trp Glu Ser Asn Gly Gln Pro Glu Asn Asn Tyr
420 425 430

Lys Thr Thr Pro Pro Val Leu Asp Ser Asp Gly Ser Phe Phe Leu Tyr
435 440 445

Ser Lys Leu Thr Val Asp Lys Ser Arg Trp Gln Gln Gly Asn Val Phe
450 455 460

Ser Cys Ser Val Met His Glu Ala Leu His Asn His Tyr Thr Gln Lys
465 470 475 480

Ser Leu Ser Leu Ser Pro Gly Lys
485

<210> SEQ ID NO 52
<211> LENGTH: 488
<212> TYPE: PRT
<213> ORGANISM: Artificial sequence
<220> FEATURE:
<223> OTHER INFORMATION: Synthetic sequence

<400> SEQUENCE: 52

Met Gly Trp Ser Cys Ile Ile Leu Phe Leu Val Ala Thr Ala Thr Gly
1 5 10 15

```
Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Trp Ile Asn Trp Val Lys Leu Ala Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Arg Ala Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Gly Gly Tyr Phe Asp Val Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430
```

```
Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485


<210> SEQ ID NO 53
<211> LENGTH: 488
<212> TYPE: PRT
<213> ORGANISM: Artificial sequence
<220> FEATURE:
<223> OTHER INFORMATION: Synthetic sequence

<400> SEQUENCE: 53

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Trp Ile Asn Trp Val Arg Gln Ala Pro Gly Gln Gly Leu
    50                  55                  60

Glu Trp Ile Gly Asp Ile Tyr Pro Gly Ser Tyr Ile Pro Asn Tyr Asn
65                  70                  75                  80

Glu Lys Phe Lys Asn Arg Ala Thr Leu Thr Val Asp Thr Ser Ala Ser
                85                  90                  95

Thr Ala Tyr Met Glu Leu Ser Ser Leu Ala Ser Glu Asp Thr Ala Leu
            100                 105                 110

Tyr Tyr Cys Ala Gly Gly Tyr Phe Asp Val Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Asp Ile Val Met Thr Gln Ser Pro Ser Ser Leu Ser
145                 150                 155                 160

Val Ser Ala Gly Glu Lys Val Thr Met Ser Cys Lys Ser Ser Gln Ser
                165                 170                 175

Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300
```

Val Asp Val Ser His Glu Asp Pro Glu Val Lys Phe Asn Trp Tyr Val
305 310 315 320

Asp Gly Val Glu Val His Asn Ala Lys Thr Lys Pro Arg Glu Glu Gln
325 330 335

Tyr Asn Ser Thr Tyr Arg Val Val Ser Val Leu Thr Val Leu His Gln
340 345 350

Asp Trp Leu Asn Gly Lys Glu Tyr Lys Cys Lys Val Ser Asn Lys Ala
355 360 365

Leu Pro Ala Pro Ile Glu Lys Thr Ile Ser Lys Ala Lys Gly Gln Pro
370 375 380

Arg Glu Pro Gln Val Tyr Thr Leu Pro Pro Ser Arg Asp Glu Leu Thr
385 390 395 400

Lys Asn Gln Val Ser Leu Thr Cys Leu Val Lys Gly Phe Tyr Pro Ser
405 410 415

Asp Ile Ala Val Glu Trp Glu Ser Asn Gly Gln Pro Glu Asn Asn Tyr
420 425 430

Lys Thr Thr Pro Pro Val Leu Asp Ser Asp Gly Ser Phe Phe Leu Tyr
435 440 445

Ser Lys Leu Thr Val Asp Lys Ser Arg Trp Gln Gln Gly Asn Val Phe
450 455 460

Ser Cys Ser Val Met His Glu Ala Leu His Asn His Tyr Thr Gln Lys
465 470 475 480

Ser Leu Ser Leu Ser Pro Gly Lys
485

<210> SEQ ID NO 54
<211> LENGTH: 488
<212> TYPE: PRT
<213> ORGANISM: Artificial sequence
<220> FEATURE:
<223> OTHER INFORMATION: Synthetic sequence

<400> SEQUENCE: 54

Met Gly Trp Ser Cys Ile Ile Leu Phe Leu Val Ala Thr Ala Thr Gly
1 5 10 15

Val His Ser Gln Val Gln Leu Val Gln Ser Gly Ala Glu Val Lys Lys
20 25 30

Pro Gly Ser Ser Val Lys Val Ser Cys Lys Ala Ser Gly Tyr Thr Phe
35 40 45

Thr Ser Tyr Trp Ile Asn Trp Val Arg Gln Ala Pro Gly Gln Gly Leu
50 55 60

Glu Trp Ile Gly Asp Ile Tyr Pro Gly Ser Tyr Ile Pro Asn Tyr Asn
65 70 75 80

Glu Lys Phe Lys Asn Arg Ala Thr Leu Thr Val Asp Thr Ser Ala Ser
85 90 95

Thr Ala Tyr Met Glu Leu Ser Ser Leu Arg Ser Glu Asp Thr Ala Val
100 105 110

Tyr Tyr Cys Ala Gly Gly Tyr Phe Asp Val Trp Gly Gln Gly Thr Thr
115 120 125

Val Thr Val Ser Ser Gly Gly Gly Gly Ser Gly Gly Gly Gly Ser Gly
130 135 140

Gly Gly Gly Ser Asp Ile Val Met Thr Gln Ser Pro Ser Ser Leu Ser
145 150 155 160

Val Ser Ala Gly Glu Lys Val Thr Met Ser Cys Lys Ser Ser Gln Ser
165 170 175

-continued

```
Leu Leu Ser Ser Gly Asn Gln Lys Asn Tyr Leu Ala Trp Tyr Gln Gln
            180                 185                 190

Lys Pro Gly Gln Pro Pro Lys Leu Leu Ile Tyr Gly Ala Ser Thr Arg
        195                 200                 205

Glu Ser Gly Val Pro Asp Arg Phe Thr Gly Ser Gly Ser Gly Thr Asp
    210                 215                 220

Phe Thr Leu Thr Ile Ser Ser Val Gln Ala Glu Asp Leu Ala Val Tyr
225                 230                 235                 240

Tyr Cys Gln Asn Asp His Ser Tyr Pro Tyr Thr Phe Gly Gly Gly Thr
                245                 250                 255

Lys Leu Glu Ile Lys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485
```